United States Patent
Liu et al.

(10) Patent No.: US 10,391,199 B2
(45) Date of Patent: Aug. 27, 2019

(54) POROUS MATERIALS, METHODS OF MAKING AND USES

(71) Applicant: Allergan, Inc., Irvine, CA (US)

(72) Inventors: Futian Liu, Sunnyvale, CA (US); Nicholas J. Manesis, Escondido, CA (US); Alexei Goraltchouk, Rensselaer, NY (US); Dimitri Stroumpoulis, Goleta, CA (US)

(73) Assignee: ALLERGAN, INC., Irvine, CA (US)

( * ) Notice: Subject to any disclaimer, the term of this patent is extended or adjusted under 35 U.S.C. 154(b) by 822 days.

(21) Appl. No.: 14/842,569

(22) Filed: Sep. 1, 2015

(65) Prior Publication Data

US 2016/0022866 A1  Jan. 28, 2016

Related U.S. Application Data

(63) Continuation of application No. 13/625,159, filed on Sep. 24, 2012, now Pat. No. 9,138,309, which is a continuation-in-part of application No. 13/104,888, filed on May 10, 2011, now abandoned, and a continuation-in-part of application No. 13/021,615, filed on Feb. 4, 2011, now Pat. No. 9,072,821.

(60) Provisional application No. 61/333,613, filed on May 11, 2010, provisional application No. 61/301,864, filed on Feb. 5, 2010.

(51) Int. Cl.
| | | |
|---|---|---|
| *A61F 2/12* | (2006.01) | |
| *A61L 27/18* | (2006.01) | |
| *B29C 41/14* | (2006.01) | |
| *A61L 27/50* | (2006.01) | |
| *A61L 27/56* | (2006.01) | |
| *A61L 27/58* | (2006.01) | |

(52) U.S. Cl.
CPC ............... *A61L 27/18* (2013.01); *A61F 2/12* (2013.01); *A61L 27/50* (2013.01); *A61L 27/56* (2013.01); *A61L 27/58* (2013.01); *B29C 41/14* (2013.01); *B05D 2400/00* (2013.01); *B05D 2518/00* (2013.01)

(58) Field of Classification Search
None
See application file for complete search history.

(56) References Cited

U.S. PATENT DOCUMENTS

| | | |
|---|---|---|
| 2,762,476 A | 9/1956 | Barnett |
| 2,805,208 A | 9/1957 | Roche |

(Continued)

FOREIGN PATENT DOCUMENTS

| | | |
|---|---|---|
| CA | 2049377 A1 | 3/1992 |
| EP | 0230672 A1 | 8/1987 |

(Continued)

OTHER PUBLICATIONS

Alvarez, Sonia et al, Synthesis of Macro/Mesoporous Silica and Carbon Monoliths by Using a Commercial Polyurethane Foam as Sacrificial Template, Material Letters, 2007, 2378-2381, 61.

(Continued)

*Primary Examiner* — Monica A Huson
*Assistant Examiner* — Kelsey C Grace
(74) *Attorney, Agent, or Firm* — Christopher J. Betti; Jennifer M. Dienes; Morgan, Lewis & Bockius LLP

(57) ABSTRACT

The present specification discloses porous materials, methods of forming such porous materials, biocompatible implantable devices comprising such porous materials, and methods of making such biocompatible implantable devices.

16 Claims, 8 Drawing Sheets

(56) References Cited

U.S. PATENT DOCUMENTS

| | | |
|---|---|---|
| 3,189,921 A | 6/1965 | Pangman |
| 3,293,663 A | 12/1966 | Cronin |
| 3,366,975 A | 2/1968 | Pangman |
| 3,558,768 A | 1/1971 | Klippel |
| 3,559,214 A | 2/1971 | Pangman |
| 3,600,718 A | 8/1971 | Boone |
| 3,665,520 A | 5/1972 | Perras |
| 3,700,380 A | 10/1972 | Kitrilakis |
| 3,852,832 A | 12/1974 | McGhan et al. |
| 3,934,274 A | 1/1976 | Hartley |
| 4,034,751 A | 7/1977 | Hung |
| 4,157,085 A | 6/1979 | Austad |
| 4,231,979 A | 11/1980 | White |
| 4,237,237 A | 12/1980 | Jarre |
| 4,264,990 A | 5/1981 | Hamas |
| 4,284,786 A | 8/1981 | Kammerer |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,568,559 A | 2/1986 | Nuwayser |
| 4,573,999 A | 3/1986 | Netto |
| 4,584,324 A | 4/1986 | Bauman et al. |
| 4,592,755 A | 6/1986 | Penton |
| 4,608,396 A | 8/1986 | Bauman et al. |
| 4,610,690 A | 9/1986 | Tiffany |
| 4,636,213 A | 1/1987 | Pakiam |
| 4,643,733 A | 2/1987 | Becker |
| 4,647,618 A | 3/1987 | Bauman et al. |
| 4,648,880 A | 3/1987 | Brauman |
| 4,650,487 A | 3/1987 | Chaglassian |
| 4,651,717 A | 3/1987 | Jakubczak |
| 4,652,441 A | 3/1987 | Okada |
| 4,681,587 A | 7/1987 | Eberl |
| 4,740,208 A | 4/1988 | Cavon |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,822,789 A | 4/1989 | Yamaguchi |
| 4,828,560 A | 5/1989 | Heyler |
| 4,832,686 A | 5/1989 | Anderson |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox |
| 4,950,292 A | 8/1990 | Audretsch |
| 4,955,907 A | 9/1990 | Ledergerber |
| 4,955,909 A | 9/1990 | Ersek et al. |
| 4,960,425 A | 10/1990 | Yan |
| 4,965,430 A | 10/1990 | Curtis |
| 4,969,899 A | 11/1990 | Cox |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan et al. |
| 5,026,394 A | 6/1991 | Baker |
| 5,034,422 A | 7/1991 | Triolo et al. |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,128,088 A | 7/1992 | Shimomura et al. |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,204,024 A | 4/1993 | Onaka et al. |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,279,826 A | 1/1994 | Inamura |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle et al. |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iversen |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| 5,575,987 A | 11/1996 | Kamei |
| RE35,391 E | 12/1996 | Brauman |
| 5,589,176 A | 12/1996 | Seare |
| 5,594,091 A | 1/1997 | Igari |
| 5,605,693 A | 2/1997 | Seare |
| 5,607,473 A | 3/1997 | Weber-Unger |
| 5,611,971 A | 3/1997 | Maedera |
| 5,624,674 A | 4/1997 | Seare |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare |
| 5,776,159 A | 7/1998 | Young |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,876,756 A | 3/1999 | Takada |
| 5,895,423 A | 4/1999 | Becker et al. |
| 5,935,164 A | 8/1999 | Iversen |
| 5,961,552 A | 10/1999 | Iversen et al. |
| 5,964,803 A | 10/1999 | Iversen et al. |
| 5,965,076 A | 10/1999 | Banks |
| 5,984,943 A | 11/1999 | Young |
| 5,993,716 A | 11/1999 | Draenert |
| 6,045,830 A | 4/2000 | Igari |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,113,941 A | 9/2000 | Takada |
| 6,113,943 A | 9/2000 | Okada |
| 6,117,455 A | 9/2000 | Takada |

(56) References Cited

U.S. PATENT DOCUMENTS

| | | |
|---|---|---|
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. et al. |
| 6,214,926 B1 | 4/2001 | Winn |
| 6,291,456 B1 | 9/2001 | Stein |
| 6,315,796 B1 | 11/2001 | Eaton |
| 6,331,562 B1 | 12/2001 | Bhagwat |
| 6,340,648 B1 | 1/2002 | Imura et al. |
| 6,387,133 B1 | 5/2002 | Perouse |
| 6,419,961 B1 | 7/2002 | Igari |
| 6,432,138 B1 | 8/2002 | Offray |
| 6,436,923 B1 | 8/2002 | Bhagwat |
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson et al. |
| 6,593,322 B1 | 7/2003 | Bhagwat |
| 6,602,452 B2 | 8/2003 | Schuessler |
| 6,605,116 B2 | 8/2003 | Falcon et al. |
| 6,620,838 B1 | 9/2003 | McKie |
| 6,638,308 B2 | 10/2003 | Corbitt |
| 6,673,285 B2 | 1/2004 | Ma |
| 6,692,527 B1 | 2/2004 | Bellin et al. |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt |
| 6,900,055 B1 | 5/2005 | Fuller |
| 6,913,626 B2 | 7/2005 | McGhan |
| 6,916,339 B1 | 7/2005 | Missana |
| 6,921,418 B2 | 7/2005 | Ledergerber |
| 6,932,840 B1 | 8/2005 | Bretz |
| 7,081,135 B2 | 7/2006 | Smith |
| 7,081,136 B1 | 7/2006 | Becker |
| 7,105,116 B2 | 9/2006 | Bellin et al. |
| 7,169,180 B2 | 1/2007 | Brennan |
| 7,192,450 B2 | 3/2007 | Brauker |
| 7,244,270 B2 | 7/2007 | Lesh |
| 7,309,232 B2 | 12/2007 | Rutherford et al. |
| 7,323,208 B2 | 1/2008 | Ma |
| 7,476,249 B2 | 1/2009 | Frank |
| 7,520,896 B2 | 4/2009 | Benslimane |
| 7,547,393 B2 | 6/2009 | Ramaswamy |
| 7,625,405 B2 | 12/2009 | Purkait |
| 7,632,228 B2 | 12/2009 | Brauker |
| 7,632,291 B2 | 12/2009 | Stephens |
| 7,641,688 B2 | 1/2010 | Lesh |
| 7,645,475 B2 | 1/2010 | Prewett |
| 7,758,788 B2 | 7/2010 | Job |
| 7,867,061 B2 | 1/2011 | Elshout |
| 8,202,317 B2 | 6/2012 | Becker |
| 8,313,527 B2 | 11/2012 | Powell et al. |
| 8,506,627 B2 | 8/2013 | Van Epps et al. |
| 8,546,458 B2 | 10/2013 | Thompson et al. |
| 8,728,159 B2 | 5/2014 | Kim |
| 8,765,039 B1 | 7/2014 | Ledergerber |
| 9,205,577 B2 | 12/2015 | Liu |
| 2001/0014339 A1 | 8/2001 | Shigeyuki |
| 2002/0005600 A1 | 1/2002 | Ma |
| 2002/0038147 A1 | 3/2002 | Miller |
| 2002/0103229 A1 | 8/2002 | Bhagwat |
| 2002/0132854 A1 | 9/2002 | Zelman |
| 2002/0193885 A1 | 12/2002 | Legeay |
| 2003/0036803 A1 | 2/2003 | McGhan |
| 2003/0093151 A1 | 5/2003 | Zhang |
| 2003/0105469 A1 | 6/2003 | Karmon |
| 2003/0129717 A1 | 7/2003 | Becker et al. |
| 2003/0203027 A1 | 10/2003 | Verreck |
| 2003/0203926 A1 | 10/2003 | Kios |
| 2003/0205846 A1 | 11/2003 | Bellin |
| 2003/0208269 A1 | 11/2003 | Eaton et al. |
| 2003/0220330 A1 | 11/2003 | Yoshitaka |
| 2003/0232082 A1 | 12/2003 | Li |
| 2004/0010225 A1 | 1/2004 | Schuessler |
| 2004/0106634 A1 | 6/2004 | Satoh |
| 2004/0115241 A1 | 6/2004 | Calhoun |
| 2004/0127536 A1 | 7/2004 | Bhagwat |
| 2004/0127985 A1 | 7/2004 | Bellin |
| 2004/0137032 A1 | 7/2004 | Wang |
| 2004/0143327 A1 | 7/2004 | Ku |
| 2004/0148024 A1 | 7/2004 | Williams |
| 2004/0153151 A1 | 8/2004 | Gonzales de Vicente |
| 2004/0176493 A1 | 9/2004 | Ferguson |
| 2004/0213986 A1 | 10/2004 | Kim |
| 2005/0009876 A1 | 1/2005 | Bhagwat |
| 2005/0055093 A1 | 3/2005 | Brennan |
| 2005/0070124 A1 | 3/2005 | Miller |
| 2005/0112169 A1 | 5/2005 | Brauker |
| 2005/0122169 A1 | 6/2005 | Watanabe |
| 2005/0137231 A1 | 6/2005 | McKie |
| 2005/0175702 A1 | 8/2005 | Muller-Schulte |
| 2005/0196452 A1 | 9/2005 | Boyan |
| 2005/0216094 A1 | 9/2005 | Prewett |
| 2005/0251083 A1 | 11/2005 | Carr-Brendel et al. |
| 2006/0002810 A1 | 1/2006 | Grohowski, Jr. |
| 2006/0018957 A1 | 1/2006 | Lerner |
| 2006/0036266 A1 | 2/2006 | Andreevich |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2006/0257377 A1 | 11/2006 | Atala et al. |
| 2006/0287344 A1 | 12/2006 | Albers |
| 2007/0004777 A1 | 1/2007 | Bhagwat |
| 2007/0015817 A1 | 1/2007 | McKie |
| 2007/0036844 A1 | 2/2007 | Ma |
| 2007/0037882 A1 | 2/2007 | Kita |
| 2007/0060598 A1 | 3/2007 | Albers |
| 2007/0093911 A1 | 4/2007 | Fricke |
| 2007/0104693 A1 | 5/2007 | Quijano |
| 2007/0104695 A1 | 5/2007 | Quijano |
| 2007/0116735 A1 | 5/2007 | Calhoun |
| 2007/0135916 A1 | 6/2007 | Maxwell et al. |
| 2007/0154525 A1 | 7/2007 | Calhoun |
| 2007/0190108 A1 | 8/2007 | Datta |
| 2007/0198085 A1 | 8/2007 | Benslimane |
| 2008/0009830 A1 | 1/2008 | Fujimoto |
| 2008/0071371 A1 | 3/2008 | Elshout |
| 2008/0075752 A1 | 3/2008 | Ratner et al. |
| 2008/0095823 A1 | 4/2008 | Williams et al. |
| 2008/0118545 A1 | 5/2008 | Futo |
| 2008/0138453 A1 | 6/2008 | Gu |
| 2008/0154366 A1 | 6/2008 | Frank |
| 2008/0241212 A1 | 10/2008 | Moses |
| 2008/0242694 A1 | 10/2008 | D'Sidocky |
| 2008/0268019 A1 | 10/2008 | Badylak |
| 2008/0312739 A1 | 12/2008 | Agerup |
| 2009/0023724 A1 | 1/2009 | Mortensen |
| 2009/0028941 A1 | 1/2009 | Cowles |
| 2009/0042890 A1 | 2/2009 | Mortensen |
| 2009/0045166 A1 | 2/2009 | Li |
| 2009/0048275 A1 | 2/2009 | Beauchamps |
| 2009/0082864 A1 | 3/2009 | Chen |
| 2009/0087641 A1 | 4/2009 | Favis |
| 2009/0093878 A1 | 4/2009 | Glicksman |
| 2009/0118829 A1 | 5/2009 | Powell |
| 2009/0125107 A1 | 5/2009 | Maxwell |
| 2009/0148829 A1 | 6/2009 | Ecker |
| 2009/0162447 A1 | 6/2009 | Kaulty |
| 2009/0169716 A1 | 7/2009 | Linhardt |
| 2009/0198331 A1 | 8/2009 | Kesten |
| 2009/0198332 A1 | 8/2009 | Becker |
| 2009/0198333 A1 | 8/2009 | Becker |
| 2009/0270418 A1 | 10/2009 | Sloss |
| 2009/0326025 A1 | 12/2009 | Lu |
| 2010/0042211 A1 | 2/2010 | Van Epps et al. |
| 2010/0075056 A1 | 3/2010 | Axisa et al. |

(56) References Cited

U.S. PATENT DOCUMENTS

| | | |
|---|---|---|
| 2010/0093689 A1 | 4/2010 | Bahmanyar |
| 2010/0120727 A1 | 5/2010 | Xu |
| 2010/0190708 A1 | 7/2010 | Tsuno |
| 2010/0234288 A1 | 9/2010 | Jain |
| 2010/0292790 A1 | 11/2010 | Stroumpoulis et al. |
| 2011/0054605 A1 | 3/2011 | Becker |
| 2011/0082148 A1 | 4/2011 | Klopman |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0196488 A1 | 8/2011 | Goraltchouk et al. |
| 2011/0196489 A1 | 8/2011 | Van Epps et al. |
| 2011/0257623 A1 | 10/2011 | Marshall et al. |
| 2011/0276133 A1 | 11/2011 | Liu et al. |
| 2011/0276134 A1 | 11/2011 | Manesis et al. |
| 2011/0278755 A1 | 11/2011 | Liu et al. |
| 2011/0282444 A1 | 11/2011 | Liu et al. |
| 2011/0300214 A1 | 12/2011 | Rimkus |
| 2011/0309541 A1 | 12/2011 | Thompson et al. |
| 2011/0313073 A1 | 12/2011 | Goraltchouk et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077891 A1 | 3/2012 | Liu et al. |
| 2012/0101574 A1 | 4/2012 | Goraltchouk et al. |
| 2012/0245685 A1 | 9/2012 | Yu |
| 2012/0321777 A1 | 12/2012 | Stroumpoulis et al. |
| 2013/0013062 A1 | 1/2013 | Thompson et al. |
| 2013/0023987 A1 | 1/2013 | Liu et al. |
| 2013/0030025 A1 | 1/2013 | Wessel |
| 2013/0032962 A1 | 2/2013 | Liu et al. |
| 2013/0053956 A1 | 2/2013 | Powell et al. |
| 2013/0158657 A1 | 6/2013 | Nofrey et al. |
| 2013/0209661 A1 | 8/2013 | Goraltchouk et al. |
| 2013/0245148 A1 | 9/2013 | Thompson et al. |
| 2013/0302511 A1 | 11/2013 | Goraltchouk et al. |
| 2013/0310934 A1 | 11/2013 | Van Epps et al. |

FOREIGN PATENT DOCUMENTS

| | | |
|---|---|---|
| EP | 0315814 A2 | 5/1989 |
| EP | 0332371 A1 | 9/1989 |
| EP | 0522585 A1 | 1/1993 |
| EP | 0710468 B1 | 1/2002 |
| EP | 1532942 A1 | 5/2005 |
| EP | 1847369 B1 | 12/2008 |
| FR | 2840617 A1 | 12/2003 |
| GB | 1022736 A | 3/1966 |
| GB | 2225016 A | 5/1990 |
| JP | 2003-062062 | 4/2003 |
| JP | 2007-029717 | 8/2007 |
| MX | 2012012801 A | 5/2014 |
| RU | 2340308 C1 | 12/2008 |
| WO | 199715242 A1 | 5/1997 |
| WO | 1998010803 A1 | 3/1998 |
| WO | 199842318 A1 | 10/1998 |
| WO | 2000024437 A2 | 5/2000 |
| WO | 200056376 A1 | 9/2000 |
| WO | 2004037318 A2 | 5/2004 |
| WO | 2004062531 A1 | 7/2004 |
| WO | 2005020849 A2 | 3/2005 |
| WO | 2006133366 A1 | 12/2006 |
| WO | 2008001591 A1 | 1/2008 |
| WO | 2009061672 A1 | 5/2009 |
| WO | 2009110917 A1 | 9/2009 |
| WO | 2011066441 A1 | 6/2011 |
| WO | 2011094155 A2 | 8/2011 |
| WO | 2011097499 A1 | 8/2011 |

OTHER PUBLICATIONS

Barnsley, Philip et al., Textured Surface Breast Implants in the Prevention of Capsular Contracture Among Breast Augmentation Patients: A Meta-Analysis of Randomized Controlled Trials, Plastic and Reconstructive Surgery, 2006, 2182-2190, 117(7).

Barr, S., Current Implant Surface Technology: An Examination of Their Nanostructure and Their Influence on Fibroblast Alignment and Biocompatibility, J. of Plastic Surgery, 2009, 198-217, 9.

Brauker, James et al., Neovascularization of Synthetic Membranes Directed by Membrane Microarchitecture, Journal of Biomedical Materials Research, 1995, 1517-1524, 29, John Wiley & Sons, Inc.

Brohim, Robert et al., Early Tissue Reaction to Textured Breast Implant Surfaces, Anals of Plastic Surgery, 1992, 354-362, 28.

Capes et al., Fabrication of polymeric scaffolds with a controlled distribution of pores, J. of Materials Science: Materials in Medicine, Dec. 2005, 1069-1075, vol. 16, No. 12.

Inamed Aesthetics Brochure, Directions for Use Style 410 Silicone-Filled Breast Implants (2003).

Kim, et al., Modified release of coated sugar spheres using drug-containing polymeric dispersions, Archives Pharmacal Research, 2007, 124-130, vol. 30, No. 1.

Ma, Peter, Scaffolds for Tissue Fabriction, Materials Today, 2004, 30-40, 7.

Mikos, Antonios, Formation of Highly Porous Biodegradable Scaffolds for Tissue Engineering, Journal of Biotechnology, Aug. 15, 2000, 114-119, 3(2).

Minami, Eliza, The Composition and Behavior of Capsules Around Smooth and Textured Breast Implants in Pigs, Plast. Reconstr. Surg., 2006, 874-884, 118.

Murphy, William L. et al., Salt Fusion: An Approach to Improve Pore Interconnectivity Within Tissue Engineering Scaffolds, Tissue Engineering, 2002, 43-52, 8 (1), US.

Sharkawy, Adam et al., Engineering the Tissue Which Encapsulates Subcutaneous Implants. II. Plasma-Tissue Exchange Properties, Journal of Biomedical Materials Research, 1998, 586-597, 40, John Wiley & Sons, Inc.

Wei, Guobao et al., Macroporous and Nanofibrous Polymer Scaffolds and Polymer/Bone-Like Apatite Composite Scaffolds Generated by Sugar Spheres, Journal of Biomedical Materials Research, 2006, 306-315, 78A.

Zhang, et al., Macroporous Alumina Monoliths Prepared by Filling Polymer Foams with Alumina Hydrogels, Journal of Materials Science, 2009, 931-938, 44, Springer Science.

POROUS MATERIALS, METHODS OF MAKING AND USES

This is a continuation of U.S. patent application Ser. No. 13/625,159, filed on Sep. 24, 2012, now U.S. Pat. No. 9,138,308, issued Sep. 22, 2015, which is a continuation-in-part of U.S. patent application Ser. No. 13/104,888, filed May 10, 2011, which claims the benefit of U.S. Provisional Patent Application 61/333,613, filed May 11, 2010, and application Ser. No. 13/625,159 is also a continuation-in-part of U.S. patent application Ser. No. 13/021,615, filed Feb. 4, 2011, now U.S. Pat. No. 9,072,821, issued Jul. 7, 2015, which claims the benefit of U.S. Provisional Patent Application 61/301,864, filed Feb. 5, 2010, each of these documents hereby being incorporated by reference in its entirety.

Porous materials are widely used in biomedical, industrial, and household applications. In the biomedical field, porous materials have been used as scaffolds (templates) for tissue engineering/regeneration, wound dressings, drug release matrices, membranes for separations and filtration, sterile filters, artificial kidneys, absorbents, hemostatic devices, and the like. In various industrial and household applications, porous materials have been used as insulating materials, packaging materials, impact absorbers, liquid or gas absorbents, membranes, filters and so forth.

Implantable medical devices frequently induce a foreign body response that results in the formation of an avascular, fibrous capsule around the implant, which limits the performance of the device. For example, formation of these fibrous capsules can result in capsular contracture, the tightening and hardening of the capsule that surrounding implanted device. Capsular contractions not only distort the aesthetic appearance of the surrounding area where the implant is placed, but also cause pain to the individual. Problems with capsular formation and contracture occur in many types of implantable medical devices, such as, e.g., pacemakers, orthopedic joint prosthetics, dura matter substitutes, implantable cardiac defibrillators, tissue expanders, and tissue implants used for prosthetic, reconstructive, or aesthetic purposes, like breast implants, muscle implants, or implants that reduce or prevent scarring. Correction of capsular contracture may require surgical removal or release of the capsule, or removal and possible replacement of the device itself.

Scar tissue formation in the healing of a wound or surgical incision is also a process involving the formation of fibrous tissue. A visible scar results from this healing process because the fibrous tissue is aligned in one direction. However, it is often aesthetically desirable to prevent scar formation, especially in certain types of plastic surgery.

The biological response to implantable medical devices and wound healing appears dependent on the microarchitecture of the surface of the implants. Implants with smooth surfaces in particular are most susceptible to capsular formation and contracture. One means of reducing capsular formation and contracture has been to texture the surface of an implantable medical device. In these methods, a textured surface is imprinted onto the surface of a device forming "hills" and "valleys" architecture. See, e.g., U.S. Pat. No. 4,960,425, Textured Surface Prosthesis Implants; U.S. Pat. No. 5,022,942, Method of Making Textured Surface Prosthesis Implants. However, capsular contracture can still occur in implantable medical devices textured in the manner.

As such, there is a continuing need for implantable medical devices manufactured in such a way that the formation of fibrous capsules is reduced or prevented.

SUMMARY

The present application discloses porous materials, methods of making these porous materials, implantable medical devices comprising such porous materials, and methods of making such implantable medical devices. The porous materials promote cellular ingrowth in and around an implantable medical device and reduce or prevent a foreign body response, such as, e.g., capsular contracture as well as to reduce or prevent scars resulting from wound healing.

Thus, aspects of the present specification disclose a porous material comprising a substantially non-degradable, biocompatible, elastomer matrix defining an array of interconnected pores.

Other aspects of the present specification disclose a method of forming a porous material, the method comprising the steps of: a) coating porogens with an elastomer base to form an elastomer coated porogen mixture; b) treating the elastomer coated porogen mixture to form a porogen scaffold comprising fused porogens and cure the elastomer; and c) removing the porogen scaffold, wherein porogen scaffold removal results in a porous material, the porous material comprising a substantially non-degradable, biocompatible, elastomer matrix defining an array of interconnected pores.

Yet other aspects of the present specification disclose a method of forming a porous material, the method comprising the steps of: a) fusing porogens disclosed herein to form a porogen scaffold; b) coating the porogen scaffold with an elastomer base to form an elastomer coated porogen scaffold; c) treating the elastomer coated porogen scaffold to cure the elastomer; and d) removing the porogen scaffold, wherein porogen scaffold removal results in a porous material, the porous material comprising a matrix defining an array of interconnected pores.

Still other aspects of the present specification disclose a method of forming a porous material, the method comprising the steps of: a) coating porogens disclosed herein with an elastomer base to form an elastomer coated porogen mixture; b) packing material coated porogen mixture into a mold; c) treating the elastomer coated porogen mixture to form a porogen scaffold comprising fused porogens and cure the elastomer; and d) removing the porogen scaffold, wherein porogen scaffold removal results in a porous material, the porous material comprising a matrix defining an array of interconnected pores.

Still other aspects of the present specification disclose a method of forming a porous material, the method comprising the steps of: a) packing porogens disclosed herein into a mold; b) fusing the porogens to form a porogen scaffold comprising fused porogens; c) coating the porogen scaffold with an elastomer base to form an elastomer coated porogen scaffold; d) treating the elastomer coated porogen scaffold to cure the elastomer; and e) removing the porogen scaffold, wherein porogen scaffold removal results in a porous material, the porous material comprising a matrix defining an array of interconnected pores.

Further aspects of the present specification disclose a porous material comprising a substantially non-degradable, biocompatible, elastomer matrix defining an array of interconnected pores, wherein the porous material is made by the method comprising the steps of: a) coating porogens with an elastomer base to form an elastomer coated porogen mixture; b) treating the elastomer coated porogen mixture to form a porogen scaffold comprising fused porogens and cure the elastomer; and c) removing the porogen scaffold, wherein porogen scaffold removal results in a porous material, the porous material comprising a substantially non-degradable, biocompatible, elastomer matrix defining an array of interconnected pores.

Further aspects of the present specification disclose a method for making biocompatible implantable device comprising a layer of porous material disclosed herein. In some aspects the method comprises the steps of: a) coating a mandrel with an elastomer base; b) curing the elastomer base to form a base layer; c) coating the cured base layer with an elastomer base; d) coating the elastomer base with porogens to form an elastomer coated porogen mixture; e) treating the elastomer coated porogen mixture to form a porogen scaffold comprising fused porogens and cure the elastomer base; and, f) removing the porogen scaffold, wherein porogen scaffold removal results in a porous material, the porous material comprising a non-degradable, biocompatible, elastomer matrix defining an array of interconnected pores. In this method steps (c) and (d) can be repeated multiple times until the desired thickness of the material layer is achieved.

Further aspects of the present specification disclose a method of making a biocompatible implantable device, the method comprising the steps of: a) preparing the surface of a biocompatible implantable device to receive a porous material; and, b) attaching a porous material disclosed herein to the prepared surface of the biocompatible implantable device.

Further aspects of the present invention disclose a method for forming a textured implant shell, the method comprising the steps of: (a) coating a base shell, for example, a smooth breast implant shell positioned on a mandrel, with a first layer of an elastomer, the elastomer comprising a silicone base and a solvent; (b) applying porogens to the first layer of elastomer to form a first porogen-coated elastomer layer; (c) applying a second layer of the elastomer to the first porogen-coated elastomer layer; (d) applying porogens to the second layer of elastomer to form a second porogen-coated elastomer layer; (f) applying a third layer of the elastomer to the second porogen-coated elastomer layer to thereby form a multilayered porogen/elastomer coating on the base shell; (g) treating the multilayered porogen/elastomer coating on the base shell such that during the treatment the porogens become fused to one another while the uncured elastomer layers become cured, thereby forming a fused porogen scaffold surrounded by cured elastomer; and (n) removing the porogen scaffold from the cured elastomer, wherein the removing the porogen scaffold results in an interconnected open-cell textured implant shell.

In some aspects of the present specification the biocompatible implantable device is a breast implant.

BRIEF DESCRIPTION OF THE DRAWINGS

FIG. 1A is scanning electron micrograph image at 50× magnification. FIG. 1B is scanning electron micrograph image at 50× magnification.

FIG. 2A is a top view of an implantable device covered with a porous material. FIG. 2B is a side view of an implantable device covered with a porous material. FIGS. 2C and 2D illustrate the cross-sectional view of the biocompatible implantable device covered with a porous material.

FIG. 3A is a top view of a material shell. FIG. 2B is a side view of a material shell. FIG. 3C is a bottom view of a material shell. FIG. 3D illustrate the cross-sectional view of the material shell.

FIG. 4A is a top view of an implantable device covered with a porous material. FIG. 4B is a side view of an implantable device covered with a porous material. FIG. 4C is a bottom view of a biocompatible implantable device covered with a porous material. FIG. 4D illustrates the cross-sectional view of the biocompatible implantable device covered with a porous material.

FIG. 5A shows a bar graph of thickness data as normalized mean±normalized standard deviation. FIG. 5B shows a bar graph of disorganization normalized with a standard deviation with upper and lower bounds of confidence intervals.

DETAILED DESCRIPTION

Figure 1A:
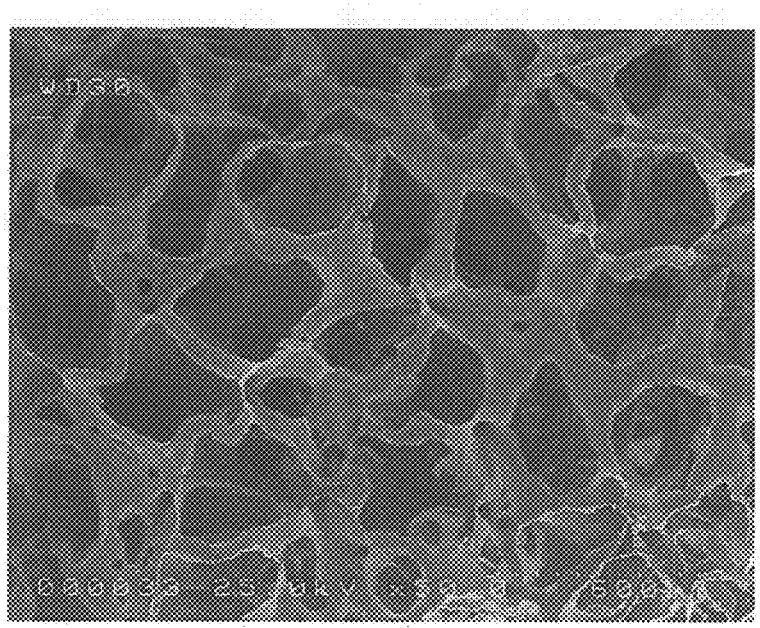
FIGS. 1A and 1B show an analysis of a porous material as disclosed in the present specification.

The present specification discloses, in part, a porous material. The disclosed porous material has high porosity and interconnected pore structures that favor tissue growth into the porous material, such as, e.g., by facilitating cell migration, cell proliferation, cell differentiation, nutrient exchange, and/or waste removal. The interconnected pore structure encourages cell infiltration and growth therein, which disrupt the planar arrangement of capsule formation. Interconnection of the pores is achieved without sacrificing mechanical strength of the porous material, that is, the material's hardness, tensile strength, elongation, tear strength, abrasion and resistance, are preserved. As such, the porous material, its application in creating biocompatible implantable devices, and other aspects disclosed herein are useful in preventing capsular contraction, and in reducing or preventing scar formation.

Even further, it is often important to anchor a biocompatible implantable device to the surrounding tissue in order to prevent slippage or unwanted movement. For example, it is important to anchor securely facial and breast implants into position to prevent slippage or any other unwanted movement. As such, the porous material, its application in creating biocompatible implantable devices, and other aspects disclosed herein are useful in anchoring biocompatible implantable devices.

A porous material disclosed herein can be implanted into the soft tissue of an animal. Such a porous material may be completely implanted into the soft tissue of an animal body (i.e., the entire material is within the body), or the device may be partially implanted into an animal body (i.e., only part of the material is implanted within an animal body, the remainder of the material being located outside of the animal body). A porous material disclosed herein can also be affixed to one or more soft tissues of an animal, typically to the skin of an animal body. For example, a strip of porous material can be placed subcutaneously underneath a healing wound or incision to prevent the fibrous tissue from aligning and thereby reducing or preventing scar formation.

The present specification discloses, in part, a porous material comprising a substantially non-degradable, biocompatible, elastomer matrix. As used herein, the term "non-degradable" refers to a material that is not prone to degrading, decomposing, or breaking down to any substantial or significant degree while implanted in the host. Non-limiting examples of substantial non-degradation include less than 10% degradation of a porous material over a time period measured, less than 5% degradation of a porous material over a time period measured, less than 3% degradation of a porous material over a time period measured, less than 1% degradation of a porous material over a time period measured. As used herein, the term "biocompatible" refers to a material's ability to perform its intended function, with a desired degree of incorporation in the host, without eliciting any undesirable local or systemic effects in that host.

In an embodiment, a porous material comprising an elastomer matrix defining an array of interconnected pores is substantially non-degradable. In aspects of this embodiment, a porous material comprising an elastomer matrix defining an array of interconnected pores is substantially non-degradable for, e.g., about five years, about ten years, about 15 years, about 20 years, about 25 years, about 30 years, about 35 years, about 40 years, about 45 years, or about 50 years. In other aspects of this embodiment, a porous material comprising an elastomer matrix defining an array of interconnected pores is substantially non-degradable for, e.g., at least five years, at least ten years, at least 15 years, at least 20 years, at least 25 years, at least 30 years, at least 35 years, at least 40 years, at least 45 years, or at least 50 years. In yet other aspects of this embodiment, a porous material comprising an elastomer matrix defining an array of interconnected pores exhibits less than 5% degradation, less than 3% degradation, or less than 1% degradation over for, e.g., about five years, about ten years, about 15 years, about 20 years, about 25 years, about 30 years, about 35 years, about 40 years, about 45 years, or about 50 years. In still other aspects of this embodiment, a porous material comprising an elastomer matrix defining an array of interconnected pores exhibits less than 5% degradation, less than 3% degradation, or less than 1% degradation over for, e.g., at least five years, at least ten years, at least 15 years, at least 20 years, at least 25 years, at least 30 years, at least 35 years, at least 40 years, at least 45 years, or at least 50 years.

In another embodiment, a porous material comprising an elastomer matrix defining an array of interconnected pores is substantially biocompatible. In aspects of this embodiment, a porous material comprising an elastomer matrix defining an array of interconnected pores is substantially biocompatible for, e.g., at least five years, at least ten years, at least 15 years, at least 20 years, at least 25 years, at least 30 years, at least 35 years, at least 40 years, at least 45 years, or at least 50 years.

As used herein, the term "elastomer" or "elastic polymer" refers to an amorphous polymer that exists above its glass transition temperature ($T_g$) at ambient temperatures, thereby conferring the property of viscoelasticity so that considerable segmental motion is possible, and includes, without limitation, carbon-based elastomers, silicon-based elastomers, thermoset elastomers, and thermoplastic elastomers. As used herein, the term "ambient temperature" refers to a temperature of about 18° C. to about 22° C. Elastomers, either naturally-occurring or synthetically-made, comprise monomers commonly made of carbon, hydrogen, oxygen, and/or silicon which are linked together to form long polymer chains. Elastomers are typically covalently cross-linked to one another, although non-covalently cross-linked elastomers are known. Elastomers may be homopolymers or copolymers, degradable, substantially non-degradable, or non-degradable. Copolymers may be random copolymers, blocked copolymers, graft copolymers, and/or mixtures thereof. Unlike other polymers classes, an elastomer can be stretched many times its original length without breaking by reconfiguring themselves to distribute an applied stress, and the cross-linkages ensure that the elastomers will return to their original configuration when the stress is removed. Elastomers can be a non-medical grade elastomer or a medical grade elastomer. Medical grade elastomers are typically divided into three categories: non implantable, short term implantable and long-term implantable. Exemplary substantially non-degradable and/or non-degradable, biocompatible, elastomers include, without limitation, bromo isobutylene isoprene (BIIR), polybutadiene (BR), chloro isobutylene isoprene (CIIR), polychloroprene (CR), chlorosulphonated polyethylene (CSM), ethylene propylene (EP), ethylene propylene diene monomer (EPDM), fluorinated hydrocarbon (FKM), fluoro silicone (FVQM), hydrogenated nitrile butadiene (HNBR), polyisoprene (IR), isobutylene isoprene butyl (IIR), methyl vinyl silicone (MVQ), acrylonitrile butadiene (NBR), polyurethane (PU), styrene butadiene (SBR), styrene ethylene/butylene styrene (SEBS), polydimethylsiloxane (PDMS), polysiloxane (SI), and acrylonitrile butadiene carboxy monomer (XNBR).

The present specification discloses, in part, an elastomer that is a silicon-based elastomer. As used herein, the tem "silicon-based elastomer" refers to any silicon containing elastomer, such as, e.g., methyl vinyl silicone, polydimethylsiloxane, or polysiloxane. A silicon-based elastomer can be a high temperature vulcanization (HTV) silicone or a room temperature vulcanization (RTV). A silicon-based elastomer can be a non-medical grade silicon-based elastomer or a medical grade silicon-based elastomer. As used herein, the term "medical grade silicon-based elastomer" refers to a silicon-based elastomer approved by the U.S. Pharmacopeia (USP) as at least Class V. Medical grade silicon-based elastomers are typically divided into three categories: non implantable, short term implantable and long-term implantable.

Thus, in an embodiment, an elastomer is a medical grade elastomer. In aspects of this embodiment, a medical grade elastomer is, e.g., a medical grade carbon-based elastomer, a medical grade silicon-based elastomer, a medical grade thermoset elastomer, or a medical grade thermoplastic elastomer. In other aspects of this embodiment, an elastomer is, e.g., a medical grade, long-term implantable, carbon-based elastomer, a medical grade, long-term implantable, silicon-based elastomer, a medical grade, long-term implantable, thermoset elastomer, or a medical grade, long-term implantable, thermoplastic elastomer. In still other aspects, a medical grade elastomer is, e.g., a medical grade bromo isobutylene isoprene, a medical grade polybutadiene, a medical grade chloro isobutylene isoprene, a medical grade polychloroprene, a medical grade chlorosulphonated polyethylene, a medical grade ethylene propylene, a medical grade ethylene propylene diene monomer, a medical grade fluorinated hydrocarbon, a medical grade fluoro silicone, a medical grade hydrogenated nitrile butadiene, a medical grade polyisoprene, a medical grade isobutylene isoprene butyl, a medical grade methyl vinyl silicone, a medical grade acrylonitrile butadiene, a medical grade polyurethane, a medical grade styrene butadiene, a medical grade styrene ethylene/butylene styrene, a medical grade polydimethylsiloxane, a medical grade polysiloxane, or a medical grade acrylonitrile butadiene carboxy monomer.

In another embodiment, an elastomer is a silicon-based elastomer. In an aspect of this embodiment, a silicon-based elastomer is a medical grade silicon-based elastomer. In aspects of this embodiment, a medical grade silicon-based elastomer is, e.g., at least a USP Class V silicon-based elastomer, at least a USP Class VI silicon-based elastomer, or USP Class VII silicon-based elastomer. In yet other aspects, a medical grade silicon-based elastomer is a long-term implantable silicon-based elastomer. In yet other aspects, a medical grade silicon-based elastomer is, e.g., a medical grade, long-term implantable, methyl vinyl silicone, a medical grade, long-term implantable, polydimethylsiloxane, or a medical grade, long-term implantable, polysiloxane.

Elastomers have the property of viscoelasticity. Viscoelasticity is the property of materials that exhibit both viscous and elastic characteristics when undergoing deformation. Viscous materials resist shear flow and strain linearly with time when a stress is applied. Elastic materials strain instantaneously when stretched and just as quickly return to their original state once the stress is removed. Viscoelastic materials have elements of both of these properties and, as such, exhibit time dependent strain. A viscoelastic material has the following properties: 1) hysteresis, or memory, is seen in the stress-strain curve; 2) stress relaxation occurs: step constant strain causes decreasing stress; and 3) creep occurs: step constant stress causes increasing strain. The viscoelasticity of elastomers confer a unique set of properties involving elongation, tensile strength, shear strength compressive modulus, and hardness that distinguish elastomers from other classes of polymers.

The present specification discloses, in part, a porous material comprising an elastomer matrix defining an array of interconnected pores. As used herein, the term "matrix" or "elastomer matrix" is synonymous with "cured elastomer" and refers to a three-dimensional structural framework composed of a substantially non-degradable, biocompatible elastomer in its cured state. As used herein, the term "silicon-based elastomer matrix" is synonymous with "cured silicon-based elastomer" and refers to a three-dimensional structural framework composed of a substantially non-degradable, biocompatible silicon-based elastomer in its cured state.

A porous material comprising an elastomer matrix defining an array of interconnected pores exhibits high resistance to deformation. Resistance to deformation is the ability of an elastomeric material to maintain its original form after being exposed to stress, and can be calculated as the original form of the elastomeric material ($L_O$), divided by the form of an elastomeric material after it is released from a stress ($L_R$), and then multiplied by 100.

In an embodiment, a porous material comprising an elastomer matrix defining an array of interconnected pores exhibits high resistance to deformation. In aspects of this embodiment, a porous material comprising an elastomer matrix defining an array of interconnected pores exhibits resistance to deformation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material comprising an elastomer matrix defining an array of interconnected pores exhibits resistance to deformation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material comprising an elastomer matrix defining an array of interconnected pores exhibits resistance to deformation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material comprising an elastomer matrix defining an array of interconnected pores exhibits resistance to deformation of, e.g., about 85% to about 100%, about 87% to about 100%, about 90% to about 100%, about 93% to about 100%, about 95% to about 100%, or about 97% to about 100%.

A porous material comprising an elastomer matrix defining an array of interconnected pores exhibits high elastic elongation. Elongation is a type of deformation caused when an elastomer stretches under a tensile stress. Deformation is simply a change in shape that anything undergoes under stress. The elongation property of an elastomeric material can be expressed as percent elongation, which is calculated as the length of an elastomer after it is stretched (L), divided by the original length of the elastomer ($L_O$), and then multiplied by 100. In addition, this elastic elongation is reversible. Reversible elongation is the ability of an elastomeric material to return to its original length after being release for a tensile stress, and can be calculated as the original length of the elastomeric material ($L_O$), divided by the length of an elastomeric material after it is released from a tensile stress ($L_R$), and then multiplied by 100.

In an embodiment, a porous material comprising an elastomer matrix defining an array of interconnected pores exhibits high elastic elongation. In aspects of this embodiment, a porous material comprising an elastomer matrix defining an array of interconnected pores exhibits an elastic elongation of, e.g., about 50%, about 80%, about 100%, about 200%, about 300%, about 400%, about 500%, about 600%, about 700%, about 800%, about 900%, about 1000%, about 1100%, about 1200%, about 1300%, about 1400%, about 1500%, about 1600%, about 1700%, about 1800%, about 1900%, or about 2000%. In other aspects of this embodiment, a porous material comprising an elastomer matrix defining an array of interconnected pores exhibits an elastic elongation of, e.g., at least 50%, at least 80%, at least 100%, at least 200%, at least 300%, at least 400%, at least 500%, at least 600%, at least 700%, at least 800%, at least 900%, at least 1000%, at least 1100%, at least 1200%, at least 1300%, at least 1400%, at least 1500%, at least 1600%, at least 1700%, at least 1800%, at least 1900%, or at least 2000%. In yet other aspects of this embodiment, a porous material comprising an elastomer matrix defining an array of interconnected pores exhibits an elastic elongation of, e.g., at most 50%, at most 80%, at most 100%, at most 200%, at most 300%, at most 400%, at most 500%, at most 600%, at most 700%, at most 800%, at most 900%, at most 1000%, at most 1100%, at most 1200%, at most 1300%, at most 1400%, at most 1500%, at most 1600%, at most 1700%, at most 1800%, at most 1900%, or at most 2000%. In still aspects of this embodiment, a porous material comprising an elastomer matrix defining an array of interconnected pores exhibits an elastic elongation of, e.g., about 50% to about 600%, about 50% to about 700%, about 50% to about 800%, about 50% to about 900%, about 50% to about 1000%, about 80% to about 600%, about 80% to about 700%, about 80% to about 800%, about 80% to about 900%, about 80% to about 1000%, about 100% to about 600%, about 100% to about 700%, about 100% to about 800%, about 100% to about 900%, about 100% to about 1000%, about 200% to about 600%, about 200% to about 700%, about 200% to about 800%, about 200% to about 900%, or about 200% to about 1000%.

In another embodiment, a porous material comprising an elastomer matrix defining an array of interconnected pores exhibits reversible elongation. In aspects of this embodiment, a porous material comprising an elastomer matrix defining an array of interconnected pores exhibits a reversible elastic elongation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material comprising an elastomer matrix defining an array of interconnected pores exhibits a reversible elastic elongation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material comprising an elastomer matrix defining an array of interconnected pores exhibits a reversible elastic elongation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material comprising an elastomer matrix defining an array of interconnected pores exhibits a reversible elastic elongation of, e.g., about 85% to about 100%, about 87% to about 100%, about 90% to about 100%, about 93% to about 100%, about 95% to about 100%, or about 97% to about 100%.

A porous material comprising an elastomer matrix defining an array of interconnected pores exhibits low elastic modulus. Elastic modulus, or modulus of elasticity, refers to the ability of an elastomeric material to resists deformation, or, conversely, an object's tendency to be non-permanently deformed when a force is applied to it. The elastic modulus of an object is defined as the slope of its stress-strain curve in the elastic deformation region: $\lambda$=stress/strain, where $\lambda$ is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an objects response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a porous material comprising an elastomer matrix defining an array of interconnected pores exhibits low tensile modulus. In aspects of this embodiment, a porous material comprising an elastomer matrix defining an array of interconnected pores exhibits a tensile modulus of, e.g., about 0.01 MPa, about 0.02 MPa, about 0.03 MPa, about 0.04 MPa, about 0.05 MPa, about 0.06 MPa, about 0.07 MPa, about 0.08 MPa, about 0.09 MPa, about 0.1 MPa, about 0.15 MPa, about 0.2 MPa, about 0.25 MPa, about 0.3 MPa, about 0.35 MPa, about 0.4 MPa, about 0.45 MPa, about 0.5 MPa, about 0.55 MPa, about 0.6 MPa, about 0.65 MPa, or about 0.7 MPa. In other aspects of this embodiment, a porous material comprising an elastomer matrix defining an array of interconnected pores exhibits a tensile modulus of, e.g., at most 0.01 MPa, at most 0.02 MPa, at most 0.03 MPa, at most 0.04 MPa, at most 0.05 MPa, at most 0.06 MPa, at most 0.07 MPa, at most 0.08 MPa, at most 0.09 MPa, at most 0.1 MPa, at most 0.15 MPa, at most 0.2 MPa, at most 0.25 MPa, at most 0.3 MPa, at most 0.35 MPa, at most 0.4 MPa, at most 0.45 MPa, at most 0.5 MPa, at most 0.55 MPa, at most 0.6 MPa, at most 0.65 MPa, or at most 0.7 MPa. In yet other aspects of this embodiment, a porous material comprising an elastomer matrix defining an array of interconnected pores exhibits a tensile modulus of, e.g., about 0.01 MPa to about 0.1 MPa, about 0.01 MPa to about 0.2 MPa, about 0.01 MPa to about 0.3 MPa, about 0.01 MPa to about 0.4 MPa, about 0.01 MPa to about 0.5 MPa, about 0.01 MPa to about 0.6 MPa, or about 0.01 MPa to about 0.7 MPa.

In another embodiment, a porous material comprising an elastomer matrix defining an array of interconnected pores exhibits low shear modulus. In aspects of this embodiment, a porous material comprising an elastomer matrix defining an array of interconnected pores exhibits a shear modulus of, e.g., about 0.1 MPa, about 0.2 MPa, about 0.3 MPa, about 0.4 MPa, about 0.5 MPa, about 0.6 MPa, about 0.7 MPa, about 0.8 MPa, about 0.9 MPa, about 1 MPa, about 1.5 MPa, about 2 MPa, about 2.5 MPa, or about 3 MPa. In other aspects of this embodiment, a porous material comprising an elastomer matrix defining an array of interconnected pores exhibits a shear modulus of, e.g., at most 0.1 MPa, at most 0.2 MPa, at most 0.3 MPa, at most 0.4 MPa, at most 0.5 MPa, at most 0.6 MPa, at most 0.7 MPa, at most 0.8 MPa, at most 0.9 MPa, at most 1 MPa, at most 1.5 MPa, at most 2 MPa, at most 2.5 MPa, or at most 3 MPa. In yet other aspects of this embodiment, a porous material comprising an elastomer matrix defining an array of interconnected pores exhibits a shear modulus of, e.g., about 0.1 MPa to about 1 MPa, about 0.1 MPa to about 1.5 MPa, about 0.1 MPa to about 2 MPa, about 0.1 MPa to about 2.5 MPa, or about 0.1 MPa to about 3 MPa.

In another embodiment, a porous material comprising an elastomer matrix defining an array of interconnected pores exhibits low bulk modulus. In aspects of this embodiment, a porous material comprising an elastomer matrix defining an array of interconnected pores exhibits a bulk modulus of, e.g., about 0.5 GPa, about 0.6 GPa, about 0.7 GPa, about 0.8 GPa, about 0.9 GPa, about 1 GPa, about 1.5 GPa, about 2 GPa, about 2.5 GPa, about 3 GPa, about 3.5 GPa, about 4 GPa, about 4.5 GPa, or about 5 GPa. In other aspects of this embodiment, a porous material comprising an elastomer matrix defining an array of interconnected pores exhibits a bulk modulus of, e.g., at most 0.5 GPa, at most 0.6 GPa, at most 0.7 GPa, at most 0.8 GPa, at most 0.9 GPa, at most 1

GPa, at most 1.5 GPa, at most 2 GPa, at most 2.5 GPa, at most 3 GPa, at most 3.5 GPa, at most 4 GPa, at most 4.5 GPa, or at most 5 GPa. In yet other aspects of this embodiment, a porous material comprising an elastomer matrix defining an array of interconnected pores exhibits a bulk modulus of, e.g., about 0.5 GPa to about 5 GPa, about 0.5 GPa to about 1 GPa, or about 1 GPa to about 5 GPa.

A porous material comprising an elastomer matrix defining an array of interconnected pores exhibits high tensile strength relative to other polymer classes. Other polymer classes include any other polymer not classified as an elastomer. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a porous material comprising an elastomer matrix defining an array of interconnected pores exhibits high yield strength relative to other polymer classes. In aspects of this embodiment, a porous material comprising an elastomer matrix defining an array of interconnected pores exhibits a yield strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits a yield strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits a yield strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits a yield strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprising an elastomer matrix defining an array of interconnected pores exhibits high ultimate strength relative to other polymer classes. In aspects of this embodiment, a porous material comprising an elastomer matrix defining an array of interconnected pores exhibits an ultimate strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits an ultimate strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits an ultimate strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits an ultimate strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprising an elastomer matrix defining an array of interconnected pores exhibits high breaking strength relative to other polymer classes. In aspects of this embodiment, a porous material comprising an elastomer matrix defining an array of interconnected pores exhibits a breaking strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits a breaking strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits a breaking strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits a breaking strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

A porous material comprising an elastomer matrix defining an array of interconnected pores exhibits low flexural strength relative to other polymer classes. Flexural strength, also known as bend strength or modulus of rupture, refers to an object's ability to resist deformation under load and represents the highest stress experienced within the object at its moment of rupture. It is measured in terms of stress.

In an embodiment, a porous material comprising an elastomer matrix defining an array of interconnected pores exhibits low flexural strength relative to other polymer classes. In aspects of this embodiment, a porous material comprising an elastomer matrix defining an array of interconnected pores exhibits a flexural strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits a flexural strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits a flexural strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits a flexural strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

A porous material comprising an elastomer matrix defining an array of interconnected pores exhibits high compressibility. Compressibility refers to the relative volume change in response to a pressure (or mean stress) change, and is the reciprocal of the bulk modulus.

In an embodiment, a porous material comprising an elastomer matrix defining an array of interconnected pores exhibits high compressibility. In aspects of this embodiment, a porous material comprising an elastomer matrix defining an array of interconnected pores exhibits a compressibility of, e.g., about 0.1 kPa, about 0.5 kPa, about 1 kPa, about 5 kPa, about 10 kPa, about 15 kPa, about 20 kPa, about 30 kPa, about 40 kPa, about 50 kPa, about 60 kPa, about 70 kPa, about 80 kPa, about 90 kPa, or about 100 kPa. In other aspects of this embodiment, a porous material comprising an elastomer matrix defining an array of interconnected pores exhibits a compressibility of, e.g., at least 0.1 kPa, at least 0.5 kPa, at least 1 kPa, at least 5 kPa, at least 10 kPa, at least 15 kPa, at least 20 kPa, at least 30 kPa, at least 40 kPa, at least 50 kPa, at least 60 kPa, at least 70 kPa, at least 80 kPa, at least 90 kPa, or at least 100 kPa. In yet other aspects of this embodiment, a porous material comprising an elastomer matrix defining an array of interconnected pores exhibits a compressibility of, e.g., at most 0.1 kPa, at most 0.5 kPa, at most 1 kPa, at most 5 kPa, at most 10 kPa, at most 15 kPa, at most 20 kPa, at most 30 kPa, at most 40 kPa, at most 50 kPa, at most 60 kPa, at most 70 kPa, at most 80 kPa, at most 90 kPa, or at most 100 kPa. In still other aspects of this embodiment, a porous material comprising an elastomer matrix defining an array of interconnected pores exhibits a compressibility of, e.g., about 0.1 kPa to about 100 kPa, about 0.5 kPa to about 100 kPa, about 1 kPa to about 100 kPa, about 5 kPa to about 100 kPa, about 10 kPa to about 100 kPa, about 1 kPa to about 30 kPa, about 1 kPa to about 40 kPa, about 1 kPa to about 50 kPa, or about 1 kPa to about 60 kPa.

A porous material comprising an elastomer matrix defining an array of interconnected pores exhibits low hardness. Hardness refers to various properties of an object in the solid phase that gives it high resistance to various kinds of shape change when force is applied. Hardness is measured using a durometer and is a unitless value that ranges from zero to 100.

In an embodiment, a porous material comprising an elastomer matrix defining an array of interconnected pores exhibits low hardness. In aspects of this embodiment, a porous material comprising an elastomer matrix defining an array of interconnected pores exhibits a hardness of, e.g., about 5, about 10, about 15, about 20, about 25, about 30, about 35, about 40, about 45, about 50, about 55, or about 60. In other aspects of this embodiment, a porous material comprising an elastomer matrix defining an array of interconnected pores exhibits a hardness of, e.g., at least 5, at least 10, at least 15, at least 20, at least 25, at least 30, at least 35, at least 40, at least 45, at least 50, at least 55, or at least 60. In yet other aspects of this embodiment, a porous material comprising an elastomer matrix defining an array of interconnected pores exhibits a hardness of, e.g., at most 5, at most 10, at most 15, at most 20, at most 25, at most 30, at most 35, at most 40, at most 45, at most 50, at most 55, or at most 60. In still other aspects of this embodiment, a porous material comprising an elastomer matrix defining an array of interconnected pores exhibits a hardness of, e.g., about 5 to about 60, about 10 to about 50, about 15 to about 45, about 20 to about 40, or about 25 to about 35.

A porous material comprising an elastomer matrix includes pores having a shape sufficient to allow tissue growth into the array of interconnected pores. As such, the pore shape should support aspects of tissue growth such as, e.g., cell migration, cell proliferation, cell differentiation, nutrient exchange, and/or waste removal. Any pore shape is useful with the proviso that the pore shape is sufficient to allow tissue growth into the array of interconnected pores. Useful pore shapes include, without limitation, roughly spherical, perfectly spherical, dodecahedrons (such as pentagonal dodecahedrons), and ellipsoids.

A porous material comprising an elastomer matrix includes pores having a roundness sufficient to allow tissue growth into the array of interconnected pores. As such, the pore roundness should support aspects of tissue growth such as, e.g., cell migration, cell proliferation, cell differentiation, nutrient exchange, and/or waste removal. As used herein, "roundness" is defined as $(6 \times V)/(\pi \times D^3)$, where V is the volume and D is the diameter. Any pore roundness is useful with the proviso that the pore roundness is sufficient to allow tissue growth into the array of interconnected pores.

A porous material comprising an elastomer matrix is formed in such a manner that substantially all the pores in the elastomer matrix have a similar diameter. As used herein, the term "substantially," when used to describe pores, refers to at least 90% of the pores within the elastomer matrix such as, e.g., at least 95% or at least 97% of the pores. As used herein, the term "similar diameter," when used to describe pores, refers to a difference in the diameters of the two pores that is less than about 20% of the larger diameter. As used herein, the term "diameter," when used to describe pores, refers to the longest line segment that can be drawn that connects two points within the pore, regardless of whether the line passes outside the boundary of the pore. Any pore diameter is useful with the proviso that the pore diameter is sufficient to allow tissue growth into the porous material. As such, the pore diameter size should support aspects of tissue growth such as, e.g., cell migration, cell proliferation, cell differentiation, nutrient exchange, and/or waste removal.

A porous material comprising an elastomer matrix is formed in such a manner that the diameter of the connections between pores is sufficient to allow tissue growth into the array of interconnected pores. As such, the diameter of the connections between pores should support aspects of tissue growth such as, e.g., cell migration, cell proliferation, cell differentiation, nutrient exchange, and/or waste removal. As used herein, the term "diameter," when describing the connection between pores, refers to the diameter of the cross-section of the connection between two pores in the plane normal to the line connecting the centroids of the two pores, where the plane is chosen so that the area of the cross-section of the connection is at its minimum value. As used herein, the term "diameter of a cross-section of a connection" refers to the average length of a straight line segment that passes through the center, or centroid (in the case of a connection having a cross-section that lacks a center), of the cross-section of a connection and terminates at the periphery of the cross-section. As used herein, the term "substantially," when used to describe the connections between pores refers to at least 90% of the connections made between each pore comprising the elastomer matrix, such as, e.g., at least 95% or at least 97% of the connections.

Thus, in an embodiment, a porous material comprising an elastomer matrix includes pores having a roundness sufficient to allow tissue growth into the array of interconnected pores. In aspects of this embodiment, a porous material comprising an elastomer matrix includes pores having a roundness of, e.g., about 0.1, about 0.2, about 0.3, about 0.4, about 0.5, about 0.6, about 0.7, about 0.8, about 0.9, or about 1.0. In other aspects of this embodiment, a porous material comprising an elastomer matrix includes pores having a roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, a porous material comprising an elastomer matrix includes pores having a roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, a porous material comprising an elastomer matrix includes pores having a roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

In another embodiment, substantially all pores within a porous material comprising an elastomer matrix have a similar diameter. In aspects of this embodiment, at least 90% of all pores within a porous material comprising an elastomer matrix have a similar diameter, at least 95% of all pores within a porous material comprising an elastomer matrix have a similar diameter, or at least 97% of all pores within a porous material comprising an elastomer matrix have a similar diameter. In another aspect of this embodiment, difference in the diameters of two pores is, e.g., less than about 20% of the larger diameter, less than about 15% of the larger diameter, less than about 10% of the larger diameter, or less than about 5% of the larger diameter.

In another embodiment, a porous material comprising an elastomer matrix includes pores having a mean diameter sufficient to allow tissue growth into the array of interconnected pores. In aspects of this embodiment, a porous material comprising an elastomer matrix includes pores having mean pore diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porous material comprising an elastomer matrix includes pores having mean pore diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porous material comprising an elastomer matrix includes pores having mean pore diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porous material comprising an elastomer matrix includes pores having mean pore diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porous material comprising an elastomer matrix includes pores having mean pore diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porous material comprising an elastomer matrix includes pores having mean pore diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porous material comprising an elastomer matrix includes pores having mean pore diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porous material comprising an elastomer matrix includes pores having a mean elastomer strut thickness sufficient to allow tissue growth into the array of interconnected pores. In aspects of this embodiment, a porous material comprising an elastomer matrix includes pores having a mean elastomer strut thickness of, e.g., about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, or about 200 µm. In other aspects of this embodiment, a porous material comprising an elastomer matrix includes pores having a mean elastomer strut thickness of, e.g., at least 10 µm, at least 20 µm, at least 30 µm, at least 40 µm, at least 50 µm, at least 60 µm, at least 70 µm, at least 80 µm, at least 90 µm, at least 100 µm, at least 110 µm, at least 120 µm, at least 130 µm, at least 140 µm, at least 150 µm, at least 160 µm, at least 170 µm, at least 180 µm, at least 190 µm, or at least 200 µm. In yet other aspects of this embodiment, a porous material comprising an elastomer matrix includes pores having a mean elastomer strut thickness of, e.g., at most 10 µm, at most 20 µm, at most 30 µm, at most 40 µm, at most 50 µm, at most 60 µm, at most 70 µm, at most 80 µm, at most 90 µm, at most 100 µm, at most 110 µm, at most 120 µm, at most 130 µm, at most 140 µm, at most 150 µm, at most 160 µm, at most 170 µm, at most 180 µm, at most 190 µm, or at most 200 µm. In still aspects of this embodiment, a porous material comprising an elastomer matrix includes pores having a mean elastomer strut thickness of, e.g., about 50 µm to about 110 µm, about 50 µm to about 120 µm, about 50 µm to about 130 µm, about 50 µm to about 140 µm, about 50 µm to about 150 µm, about 60 µm to about 110 µm, about 60 µm to about 120 µm, about 60 µm to about 130 µm, about 60 µm to about 140 µm, about 70 µm to about 110 µm, about 70 µm to about 120 µm, about 70 µm to about 130 µm, or about 70 µm to about 140 µm.

In another embodiment, a porous material comprising an elastomer matrix includes pores connected to a plurality of other pores. In aspects of this embodiment, a porous material comprising an elastomer matrix comprises a mean pore connectivity, e.g., about two other pores, about three other pores, about four other pores, about five other pores, about six other pores, about seven other pores, about eight other pores, about nine other pores, about ten other pores, about 11 other pores, or about 12 other pores. In other aspects of this embodiment, a porous material comprising an elastomer matrix comprises a mean pore connectivity, e.g., at least two other pores, at least three other pores, at least four other pores, at least five other pores, at least six other pores, at least seven other pores, at least eight other pores, at least nine other pores, at least ten other pores, at least 11 other pores, or at least 12 other pores. In yet other aspects of this embodiment, a porous material comprising an elastomer matrix comprises a mean pore connectivity, e.g., at most two other pores, at least most other pores, at least most other pores, at least most other pores, at most six other pores, at most seven other pores, at most eight other pores, at most nine other pores, at most ten other pores, at most 11 other pores, or at most 12 other pores.

In still other aspects of this embodiment, a porous material comprising an elastomer matrix includes pores connected to, e.g., about two other pores to about 12 other pores, about two other pores to about 11 other pores, about two other pores to about ten other pores, about two other pores to about nine other pores, about two other pores to about eight other pores, about two other pores to about seven other pores, about two other pores to about six other pores, about two other pores to about five other pores, about three other pores to about 12 other pores, about three other pores to about 11 other pores, about three other pores to about ten other pores, about three other pores to about nine other pores, about three other pores to about eight other pores, about three other pores to about seven other pores, about three other pores to about six other pores, about three other pores to about five other pores, about four other pores to about 12 other pores, about four other pores to about 11 other pores, about four other pores to about ten other pores, about four other pores to about nine other pores, about four other pores to about eight other pores, about four other pores to about seven other pores, about four other pores to about six other pores, about four other pores to about five other pores, about five other pores to about 12 other pores, about five other pores to about 11 other pores, about five other pores to about ten other pores, about five other pores to about nine other pores, about five other pores to about eight other pores, about five other pores to about seven other pores, or about five other pores to about six other pores.

In another embodiment, a porous material comprising an elastomer matrix includes a surface openness sufficient to allow tissue growth into the array of interconnected pores. Surface openness, or first level openness, refers to the percentage area that the pores at the surface of a porous material are exposed to the surroundings. Surface openness may be determined by examining a top view image of a porous material. In aspects of this embodiment, a porous material comprising an elastomer matrix includes a surface openness of, e.g., about 45%, about 50%, about 55%, about 60%, about 65%, about 70%, about 75%, about 80%, about 85%, about 90%, about 93%, about 95%, about 97%, or about 100%. In other aspects of this embodiment, a porous material comprising an elastomer matrix includes a surface openness of, e.g., at least 45%, at least 50%, at least 55%, at least 60%, at least 65%, at least 70%, at least 75%, at least 80%, at least 85%, at least 90%, at least 93%, at least 95%, at least 97%, or at least 100%. In yet other aspects of this embodiment, a porous material comprising an elastomer matrix includes a surface openness of, e.g., about 45% to about 100%, about 50% to about 100%, about 55% to about 100%, about 60% to about 100%, about 65% to about 100%, about 70% to about 100%, about 75% to about 100%, about 80% to about 100%, or about 85% to about 100%.

In another embodiment, a porous material comprising an elastomer matrix includes an interconnectivity between pores sufficient to allow tissue growth into the array of interconnected pores. Interconnectivity, or second level openness, may be determined by measuring the area of visible openings or interconnections within each pore or surface opening from a top view image of a porous material and relating that area to the total area of the analyzed image. In aspects of this embodiment, a porous material comprising an elastomer matrix includes an interconnectivity between pores of, e.g., about 8%, about 9%, about 10%, about 11%, about 12%, about 13%, about 14%, about 15%, about 16%, about 17%, about 18%, about 19%, or about 20%. In other aspects of this embodiment, a porous material comprising an elastomer matrix includes an interconnectivity between pores of, e.g., at least 8%, at least 9%, at least 10%, at least 11%, at least 12%, at least 13%, at least 14%, at least 15%, at least 16%, at least 17%, at least 18%, at least 19%, or at least 20%. In yet other aspects of this embodiment, a porous material comprising an elastomer matrix includes an inter-connectivity between pores of, e.g., about 8% to about 20%, about 9% to about 20%, about 10% to about 20%, about 11% to about 20%, about 12% to about 20%, about 13% to about 20%, about 14% to about 20%, or about 15% to about 20%. In yet other aspects of this embodiment, a porous material comprising a substance matrix includes an interconnectivity between pores of, e.g., about 6% to about 22%, about 7% to about 21%, about 8% to about 20%, about 9% to about 19%, about 10% to about 18%, about 11% to about 17%, about 12% to about 16%, or about 13% to about 15%.

In another embodiment, a porous material comprising an elastomer matrix includes pores where the diameter of the connections between pores is sufficient to allow tissue growth into the array of interconnected pores. In aspects of this embodiment, a porous material comprising an elastomer matrix includes pores where the diameter of the connections between pores is, e.g., about 10% the mean pore diameter, about 20% the mean pore diameter, about 30% the mean pore diameter, about 40% the mean pore diameter, about 50% the mean pore diameter, about 60% the mean pore diameter, about 70% the mean pore diameter, about 80% the mean pore diameter, or about 90% the mean pore diameter. In other aspects of this embodiment, a porous material comprising an elastomer matrix includes pores where the diameter of the connections between pores is, e.g., at least 10% the mean pore diameter, at least 20% the mean pore diameter, at least 30% the mean pore diameter, at least 40% the mean pore diameter, at least 50% the mean pore diameter, at least 60% the mean pore diameter, at least 70% the mean pore diameter, at least 80% the mean pore diameter, or at least 90% the mean pore diameter. In yet other aspects of this embodiment, a porous material comprising an elastomer matrix includes pores where the diameter of the connections between pores is, e.g., at most 10% the mean pore diameter, at most 20% the mean pore diameter, at most 30% the mean pore diameter, at most 40% the mean pore diameter, at most 50% the mean pore diameter, at most 60% the mean pore diameter, at most 70% the mean pore diameter, at most 80% the mean pore diameter, or at most 90% the mean pore diameter.

In still other aspects of this embodiment, a porous material comprising an elastomer matrix includes pores where the diameter of the connections between pores is, e.g., about 10% to about 90% the mean pore diameter, about 15% to about 90% the mean pore diameter, about 20% to about 90% the mean pore diameter, about 25% to about 90% the mean pore diameter, about 30% to about 90% the mean pore diameter, about 35% to about 90% the mean pore diameter, about 40% to about 90% the mean pore diameter, about 10% to about 80% the mean pore diameter, about 15% to about 80% the mean pore diameter, about 20% to about 80% the mean pore diameter, about 25% to about 80% the mean pore diameter, about 30% to about 80% the mean pore diameter, about 35% to about 80% the mean pore diameter, about 40% to about 80% the mean pore diameter, about 10% to about 70% the mean pore diameter, about 15% to about 70% the mean pore diameter, about 20% to about 70% the mean pore diameter, about 25% to about 70% the mean pore diameter, about 30% to about 70% the mean pore diameter, about 35% to about 70% the mean pore diameter, about 40% to about 70% the mean pore diameter, about 10% to about 60% the mean pore diameter, about 15% to about 60% the mean pore diameter, about 20% to about 60% the mean pore diameter, about 25% to about 60% the mean pore diameter, about 30% to about 60% the mean pore diameter, about 35% to about 60% the mean pore diameter, about 40% to about 60% the mean pore diameter, about 10% to about 50% the mean pore diameter, about 15% to about 50% the mean pore diameter, about 20% to about 50% the mean pore diameter, about 25% to about 50% the mean pore diameter, about 30% to about 50% the mean pore diameter, about 10% to about 40% the mean pore diameter, about 15% to about 40% the mean pore diameter, about 20% to about 40% the mean pore diameter, about 25% to about 40% the mean pore diameter, or about 30% to about 40% the mean pore diameter.

The present specification discloses, in part, a porous material comprising an elastomer matrix defining an array of interconnected pores having a porosity that is sufficient to allow tissue growth into the array of interconnected pores as disclosed herein. As such, the porosity should support aspects of tissue growth such as, e.g., cell migration, cell proliferation, cell differentiation, nutrient exchange, and/or waste removal. As used herein, the term "porosity" refers to the amount of void space in a porous material comprising an elastomer matrix. As such, the total volume of a porous material comprising an elastomer matrix disclosed herein is based upon the elastomer space and the void space.

Thus, in an embodiment, a porous material comprising an elastomer matrix defining an array of interconnected pores has a porosity sufficient to allow tissue growth into the array of interconnected pores. In aspects of this embodiment, a porous material comprising an elastomer matrix comprises a porosity of, e.g., about 40% of the total volume of an elastomer matrix, about 50% of the total volume of an elastomer matrix, about 60% of the total volume of an elastomer matrix, about 70% of the total volume of an elastomer matrix, about 80% of the total volume of an elastomer matrix, about 90% of the total volume of an elastomer matrix, about 95% of the total volume of an elastomer matrix, or about 97% of the total volume of an elastomer matrix. In other aspects of this embodiment, a porous material comprising an elastomer matrix comprises a porosity of, e.g., at least 40% of the total volume of an elastomer matrix, at least 50% of the total volume of an elastomer matrix, at least 60% of the total volume of an elastomer matrix, at least 70% of the total volume of an elastomer matrix, at least 80% of the total volume of an elastomer matrix, at least 90% of the total volume of an elastomer matrix, at least 95% of the total volume of an elastomer matrix, or at least 97% of the total volume of an elastomer matrix. In yet other aspects of this embodiment, a porous material comprising an elastomer matrix comprises a porosity of, e.g., at most 40% of the total volume of an elastomer matrix, at most 50% of the total volume of an elastomer matrix, at most 60% of the total volume of an elastomer matrix, at most 70% of the total volume of an elastomer matrix, at most 80% of the total volume of an elastomer matrix, at most 90% of the total volume of an elastomer matrix, at most 95% of the total volume of an elastomer matrix, or at most 97% of the total volume of an elastomer matrix. In yet other aspects of this embodiment, a porous material comprising an elastomer matrix comprises a porosity of, e.g., about 40% to about 97% of the total volume of an elastomer matrix, about 50% to about 97% of the total volume of an elastomer matrix, about 60% to about 97% of the total volume of an elastomer matrix, about 70% to about 97% of the total volume of an elastomer matrix, about 80% to about 97% of the total volume of an elastomer matrix, about 90% to about 97% of the total volume of an elastomer matrix, about 40% to about 95% of the total volume of an elastomer matrix, about 50% to about 95% of the total volume of an elastomer matrix, about 60% to about 95% of the total volume of an elastomer matrix, about 70% to about 95% of the total volume of an elastomer matrix, about 80% to about 95% of the total volume of an elastomer matrix, about 90% to about 95% of the total volume of an elastomer matrix, about 40% to about 90% of the total volume of an elastomer matrix, about 50% to about 90% of the total volume of an elastomer matrix, about 60% to about 90% of the total volume of an elastomer matrix, about 70% to about 90% of the total volume of an elastomer matrix, or about 80% to about 90% of the total volume of an elastomer matrix.

The present specification discloses, in part, a porous material comprising an elastomer matrix defining an array of interconnected pores having a mean open pore value and/or a mean closed pore value that is sufficient to allow tissue growth into the array of interconnected pores as disclosed herein. As used herein, the term "mean open pore value" or "mean open pore" refers to the average number of pores that are connected to at least one other pore present in the elastomer matrix. As used herein, the term "mean closed pore value" or "mean closed pore" refers to the average number of pores that are not connected to any other pores present in the elastomer matrix.

Thus, in an embodiment, a porous material comprising an elastomer matrix defining an array of interconnected pores has a mean open pore value sufficient to allow tissue growth into the array of interconnected pores. In aspects of this embodiment, a porous material comprising an elastomer matrix has a mean open pore value of, e.g., about 70%, about 75%, about 80%, about 85%, about 90%, about 95%, or about 97%. In other aspects of this embodiment, a porous material comprising an elastomer matrix comprises a mean open pore value of, e.g., at least 70%, at least 75%, at least 80%, at least 85%, at least 90%, at least 95%, or at least 97%. In yet other aspects of this embodiment, a porous material comprising an elastomer matrix has a mean open pore value of, e.g., at most 70%, at most 75%, at most 80%, at most 85%, at most 90%, at most 95%, or at most 97%. In still aspects of this embodiment, a porous material comprising an elastomer matrix has a mean open pore value of, e.g., about 70% to about 90%, about 75% to about 90%, about 80% to about 90%, about 85% to about 90%, about 70% to about 95%, about 75% to about 95%, about 80% to about 95%, about 85% to about 95%, about 90% to about 95%, about 70% to about 97%, about 75% to about 97%, about 80% to about 97%, about 85% to about 97%, or about 90% to about 97%.

In another embodiment, a porous material comprising an elastomer matrix defining an array of interconnected pores has a mean closed pore value sufficient to allow tissue growth into the array of interconnected pores. In aspects of this embodiment, a porous material comprising an elastomer matrix has a mean closed pore value of, e.g., about 5%, about 10%, about 15%, or about 20%. In other aspects of this embodiment, a porous material comprising an elastomer matrix has a mean closed pore value of, e.g., about 5% or less, about 10% or less, about 15% or less, or about 20% or less. In yet other aspects of this embodiment, a porous material comprising an elastomer matrix has a mean closed pore value of, e.g., about 5% to about 10%, about 5% to about 15%, or about 5% to about 20%.

The present specification discloses, in part, a porous material comprising an elastomer matrix defining an array of interconnected pores having a void space that is sufficient to allow tissue growth into the array of interconnected pores. As such, the void space should support aspects of tissue growth such as, e.g., cell migration, cell proliferation, cell differentiation, nutrient exchange, and/or waste removal. As used herein, the term "void space" refers to actual or physical space in a porous material comprising an elastomer matrix. As such, the total volume of a porous material comprising an elastomer matrix disclosed herein is based upon the elastomer space and the void space.

Thus, in an embodiment, an elastomer matrix defining an array of interconnected pores has a void volume sufficient to allow tissue growth into the array of interconnected pores. In aspects of this embodiment, a porous material comprising an elastomer matrix comprises a void space of, e.g., about 50% of the total volume of an elastomer matrix, about 60% of the total volume of an elastomer matrix, about 70% of the total volume of an elastomer matrix, about 80% of the total volume of an elastomer matrix, about 90% of the total volume of an elastomer matrix, about 95% of the total volume of an elastomer matrix, or about 97% of the total volume of an elastomer matrix. In other aspects of this embodiment, a porous material comprising an elastomer matrix comprises a void space of, e.g., at least 50% of the total volume of an elastomer matrix, at least 60% of the total volume of an elastomer matrix, at least 70% of the total volume of an elastomer matrix, at least 80% of the total volume of an elastomer matrix, at least 90% of the total volume of an elastomer matrix, at least 95% of the total volume of an elastomer matrix, or at least 97% of the total volume of an elastomer matrix. In yet other aspects of this embodiment, a porous material comprising an elastomer matrix comprises a void space of, e.g., at most 50% of the total volume of an elastomer matrix, at most 60% of the total volume of an elastomer matrix, at most 70% of the total volume of an elastomer matrix, at most 80% of the total volume of an elastomer matrix, at most 90% of the total volume of an elastomer matrix, at most 95% of the total volume of an elastomer matrix, or at most 97% of the total volume of an elastomer matrix. In yet other aspects of this embodiment, a porous material comprising an elastomer matrix comprises a void space of, e.g., about 50% to about 97% of the total volume of an elastomer matrix, about 60% to about 97% of the total volume of an elastomer matrix, about 70% to about 97% of the total volume of an elastomer matrix, about 80% to about 97% of the total volume of an elastomer matrix, about 90% to about 97% of the total volume of an elastomer matrix, about 50% to about 95% of the total volume of an elastomer matrix, about 60% to about 95% of the total volume of an elastomer matrix, about 70% to about 95% of the total volume of an elastomer matrix, about 80% to about 95% of the total volume of an elastomer matrix, about 90% to about 95% of the total volume of an elastomer matrix, about 50% to about 90% of the total volume of an elastomer matrix, about 60% to about 90% of the total volume of an elastomer matrix, about 70% to about 90% of the total volume of an elastomer matrix, or about 80% to about 90% of the total volume of an elastomer matrix.

In another embodiment, a porous material comprising an elastomer matrix includes substantially no trapped porogens within the cured elastomer matrix. Porogens may become trapped within the cured elastomer matrix in situations where there is no interconnection with other pores. In aspects of this embodiment, a porous material comprising an elastomer matrix comprises, e.g., about 1 porogens/mg of porous material, about 2 porogens/mg of porous material, about 4 porogens/mg of porous material, about 5 porogens/mg of porous material, about 6 porogens/mg of porous material, about 8 porogens/mg of porous material, about 10 porogens/mg of porous material, about 15 porogens/mg of porous material, or about 20 porogens/mg of porous material. In other aspects of this embodiment, a porous material comprising an elastomer matrix comprises, e.g., at most 1 porogens/mg of porous material, at most 2 porogens/mg of porous material, at most 4 porogens/mg of porous material, at most 5 porogens/mg of porous material, at most 6 porogens/mg of porous material, at most 8 porogens/mg of porous material, at most 10 porogens/mg of porous material, at most 15 porogens/mg of porous material, or at most 20 porogens/mg of porous material. In yet other aspects of this embodiment, a porous material comprising an elastomer matrix comprises, e.g., about 1 porogens/mg of porous material to about 5 porogens/mg of porous material, about 1 porogens/mg of porous material to about 10 porogens/mg of porous material, about 1 porogens/mg of porous material to about 15 porogens/mg of porous material, or about 1 porogens/mg of porous material to about 20 porogens/mg of porous material.

In aspects of this embodiment, a porous material comprising an elastomer matrix comprises, e.g., about 50 porogens, about 100 porogens, about 200 porogens, about 300 porogens, about 400 porogens, about 500 porogens, about 600 porogens, about 700 porogens, about 800 porogens, about 900 porogens, or about 1000 porogens. In other aspects of this embodiment, a porous material comprising an elastomer matrix comprises, e.g., at most 50 porogens, at most 100 porogens, at most 200 porogens, at most 300 porogens, at most 400 porogens, at most 500 porogens, at most 600 porogens, at most 700 porogens, at most 800 porogens, at most 900 porogens, or at most 1000 porogens. In yet other aspects of this embodiment, a porous material comprising an elastomer matrix comprises, e.g., about 50 porogens to about 100 porogens, about 50 porogens to about 200 porogens, about 50 porogens to about 300 porogens, about 50 porogens to about 400 porogens, about 50 porogens to about 500 porogens, about 50 porogens to about 600 porogens, about 50 porogens to about 700 porogens, about 50 porogens to about 800 porogens, about 50 porogens to about 900 porogens, about 50 porogens to about 1000 porogens, about 200 porogens to about 300 porogens, about 200 porogens to about 400 porogens, about 200 porogens to about 500 porogens, about 200 porogens to about 600 porogens, about 200 porogens to about 700 porogens, about 200 porogens to about 800 porogens, about 200 porogens to about 900 porogens, about 200 porogens to about 1000 porogens, about 500 porogens to about 600 porogens, about 500 porogens to about 700 porogens, about 500 porogens to about 800 porogens, about 500 porogens to about 900 porogens, or about 500 porogens to about 1000 porogens.

The thickness of a porous material may be of any thickness suitable for its application. In one embodiment, a porous material comprising thickness to allow tissue growth into the array of interconnected pores. For example, a porous material may be from about 0.1 mm to about 1 mm, about 0.25 mm to about 1.5 mm, about 0.25 mm to about 2.5 mm, or about 0.5 mm to about 5 mm in thickness. In aspects of this embodiment, a porous material comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a porous material comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a porous material comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a porous material comprises a thickness of, e.g., about 100 µm to about 500 µm, about 100 µm to about 1 mm, about 100 µm to about 5 mm, about 300 µm to about 1 mm, about 300 µm to about 2 mm, about 300 µm to about 3 mm, about 300 µm to about 4 mm, about 300 µm to about 5 mm, about 500 µm to about 1 mm, about 500 µm to about 2 mm, about 500 µm to about 3 mm, about 500 µm to about 4 mm, about 500 µm to about 5 mm, about 800 µm to about 1 mm, about 800 µm to about 2 mm, about 800 µm to about 3 mm, about 800 µm to about 4 mm, about 800 µm to about 5 mm, about 1 mm to about 2 mm, about 1 mm to about 3 mm, about 1 mm to about 4 mm, about 1 mm to about 5 mm, or about 1.5 mm to about 3.5 mm.

The present specification discloses, in part, a porous material comprising an elastomer matrix defining an array of interconnected pores allowing substantial tissue growth into the interconnected pores in a time sufficient to reduce or prevent formation of fibrous capsules that can result in capsular contracture or scarring.

Thus, in an embodiment, a porous material comprising an elastomer matrix defining an array of interconnected pores allows tissue growth into the interconnected pores in a time sufficient to reduce or prevent formation of fibrous capsules that can result in capsular contracture or scarring. In aspects of this embodiment, a porous material comprising an elastomer matrix defining an array of interconnected pores allows tissue growth into the interconnected pores sufficient to reduce or prevent formation of fibrous capsules in, e.g., about 2 days after implantation, about 3 days after implantation, about 4 days after implantation, about 5 days after implantation, about 6 days after implantation, about 7 days, about 2 weeks after implantation, about 3 weeks after implantation, or about 4 weeks after implantation. In other aspects of this embodiment, a porous material comprising an elastomer matrix defining an array of interconnected pores allows tissue growth into the interconnected pores sufficient to reduce or prevent formation of fibrous capsules in, e.g., at least 2 days after implantation, at least 3 days after implantation, at least 4 days after implantation, at least 5 days after implantation, at least 6 days after implantation, at least 7 days, at least 2 weeks after implantation, at least 3 weeks after implantation, or at least 4 weeks after implantation. In yet other aspects of this embodiment, a porous material comprising an elastomer matrix defining an array of interconnected pores allows tissue growth into the interconnected pores sufficient to reduce or prevent formation of fibrous capsules in, e.g., at most 2 days after implantation, at most 3 days after implantation, at most 4 days after implantation, at most 5 days after implantation, at most 6 days after implantation, at most 7 days, at most 2 weeks after implantation, at most 3 weeks after implantation, or at most 4 weeks after implantation. In still other aspects of this embodiment, a porous material comprising an elastomer matrix defining an array of interconnected pores allows tissue growth into the interconnected pores sufficient to reduce or prevent formation of fibrous capsules in, e.g., about 2 days to about 4 days after implantation, about 2 days to about 5 days after implantation, about 2 days to about 6 days after implantation, about 2 days to about 7 days after implantation, about 1 week to about 2 weeks after implantation, about 1 week to about 3 weeks after implantation, or about 1 week to about 4 weeks after implantation.

In other aspects of this embodiment, a porous material comprising an elastomer matrix defining an array of interconnected pores reduces or prevents formation of fibrous capsules for, e.g., about 1 month after implantation, about 2 months after implantation, about 3 months after implantation, about 6 months after implantation, about 9 months after implantation, about 12 months after implantation, about 15 months after implantation, about 18 months after implantation, about 21 months after implantation, about 24 months after implantation, about 27 months after implantation, about 30 months after implantation, about 33 months after implantation, or about 36 months after implantation. In other aspects of this embodiment, a porous material comprising an elastomer matrix defining an array of interconnected pores reduces or prevents formation of fibrous capsules for, e.g., at least 1 month after implantation, at least 2 months after implantation, at least 3 months after implantation, at least 6 months after implantation, at least 9 months after implantation, at least 12 months after implantation, at least 15 months after implantation, at least 18 months after implantation, at least 21 months after implantation, about 24 months after implantation, at least 27 months after implantation, at least 30 months after implantation, at least 33 months after implantation, or at least 36 months after implantation. In yet other aspects of this embodiment, a porous material comprising an elastomer matrix defining an array of interconnected pores reduces or prevents formation of fibrous capsules for, e.g., about 2 months to about 6 months after implantation, about 2 months to about 9 months after implantation, about 2 months to about 12 months after implantation, about 2 months to about 18 months after implantation, about 6 months to about 12 months after implantation, about 6 months to about 15 months after implantation, about 6 months to about 18 months after implantation, about 6 months to about 21 months after implantation, about 12 months to about 18 months after implantation, about 12 months to about 24 months after implantation, about 12 months to about 30 months after implantation, or about 12 months to about 36 months after implantation.

A porous material comprising an elastomer matrix generally has a low level of microporosity. As used herein, the term "microporosity" refers to a measure of the presence of small micropores within a porous material comprising an elastomer matrix itself (as opposed to the pores defined by an elastomer matrix). In some embodiments, all or substantially all of the micropores in a porous material comprising an elastomer matrix are between about 0.1 µm and about 5 µm, such as between about 0.1 µm and about 3 µm or between about 0.1 µm and about 2 µm. The term "low level of microporosity" means that micropores represent less than 2% of the volume of a porous material comprising an elastomer matrix, as measured by measuring the percentage void space in a cross-section through an elastomer matrix.

Figure 1B:
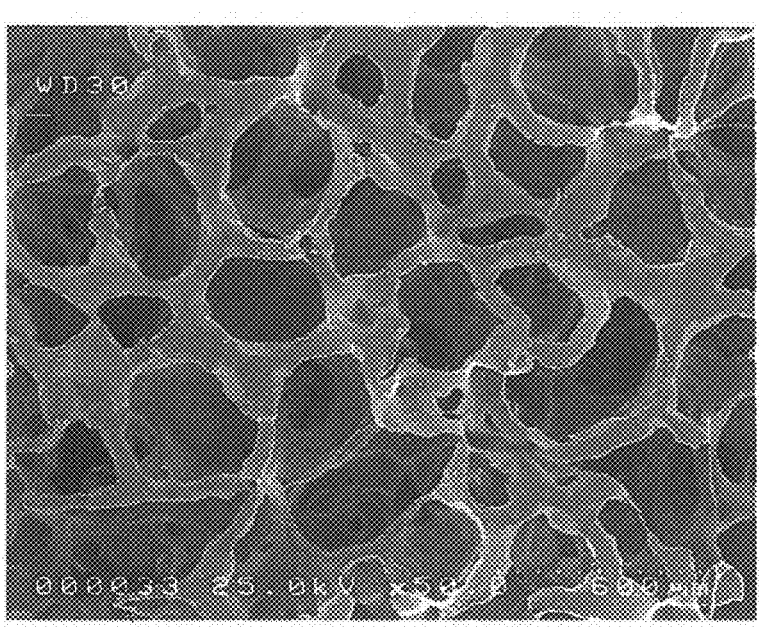

The shape, roundness, and diameter of pores, the connections between pores, the total volume of the porous material, the void volume, and the elastomer matrix volume can all be assessed using scanning electron microscopy. See, e.g., FIGS. 1A and 1B.

The present specification discloses in part, methods of making a porous material disclosed herein.

In one aspect, a method of making a porous material comprises the steps of: a) coating porogens with an elastomer base to form an elastomer coated porogen mixture; b) treating the elastomer coated porogen mixture to allow fusing of the porogens to form a porogen scaffold and curing of the non-degradable biocompatible elastomer; c) removing the porogen scaffold, wherein porogen scaffold removal results in a porous material, the porous material comprising a non-degradable, biocompatible, an elastomer matrix defining an array of interconnected pores.

In another aspect, a method of making a porous material comprises the steps of a) coating porogens with an elastomer base to form an elastomer coated porogen mixture; b) packing porogens into a mold; c) treating the elastomer coated porogen mixture to allow fusing of the porogens to form a porogen scaffold and curing of the non-degradable biocompatible elastomer; d) removing the porogen scaffold, wherein porogen scaffold removal results in a porous material, the porous material comprising a non-degradable, biocompatible, an elastomer matrix defining an array of interconnected pores.

As used herein, the term "elastomer base" is synonymous with "uncured elastomer" and refers to an elastomer disclosed herein that is in its uncured state. As used herein, the term "silicon-based elastomer base" is synonymous with "uncured silicon-based elastomer" and refers to a silicon-based elastomer disclosed herein that is in its uncured state.

As used herein, the term "porogen" refers to any structure that can be used to create a porogen scaffold that is removable after an elastomer matrix is formed under conditions that do not destroy the elastomer matrix. Porogens can be made of any material having a glass transition temperature ($T_g$) or melting temperature ($T_m$) from about 30° C. to about 100° C. In addition, porogens useful to practice aspects of the present specification should be soluble in hydrophilic solvents such as, e.g., water, dimethyl sulfoxide (DMSO), methylene chloride, chloroform, and acetone. However, porogens useful to practice aspects of the present specification should not be soluble in aromatic solvents like xylene, chlorinated solvents like dichloromethane, or any other solvent used to disperse uncured elastomer base. Exemplary porogens suitable for use in the methods disclosed herein, include, without limitation, salts, such as, e.g., sodium chloride, potassium chloride, sodium fluoride, potassium fluoride, sodium iodide, sodium nitrate, sodium sulfate, sodium iodate, and/or mixtures thereof); sugars and/or its derivatives, such as, e.g., glucose, fructose, sucrose, lactose, maltose, saccharin, and/or mixtures thereof; polysaccharides and their derivatives, such as, e.g., cellulose and hydroxyethylcellulose; waxes, such as, e.g., paraffin, beeswax, and/or mixtures thereof; other water soluble chemicals, such as, e.g., sodium hydroxide; naphthalene; polymers, such as, e.g., poly(alkylene oxide), poly(acrylamide), poly(acrylic acid), poly(acrylamide-co-acrylic acid), poly(acrylamide-co-diallyldimethylammonium chloride), polyacrylonitrile, poly(allylamine), poly(amide), poly(anhydride), poly(butylene), poly(ε-caprolactone), poly(carbonate), poly(ester), poly(etheretherketone), poly(ethersulphone), poly(ethylene), poly(ethylene alcohol), poly(ethylenimine), poly(ethylene glycol), poly(ethylene oxide), poly(glycolide) ((like poly(glycolic acid)), poly(hydroxy butyrate), poly(hydroxyethylmethacrylate), poly(hydroxypropylmethacrylate), poly(hydroxystyrene), poly(imide), poly(lactide)((like poly(L-lactic acid) and poly(D,L-lactic acid)), poly(lactide-co-glycolide), poly(lysine), poly(methacrylate), poly(methylmethacrylate), poly(orthoester), poly(phenylene oxide), poly(phosphazene), poly(phosphoester), poly(propylene fumarate), poly(propylene), poly(propylene glycol), poly(propylene oxide), poly(styrene), poly(sulfone), poly(tetrafluoroethylene), poly(vinylacetate), poly(vinyl alcohol), poly(vinylchloride), poly(vinylidene fluoride), poly(vinyl pyrrolidone), poly(urethane), any copolymer thereof (like poly(ethylene oxide) poly(propylene oxide) copolymers (poloxamers), poly(vinyl alcohol-co-ethylene), poly(styrene-co-allyl) alcohol, and poly(ethylene)-block-poly(ethylene glycol), and/or any mixtures thereof; as well as alginate, chitin, chitosan, collagen, dextran, gelatin, hyaluronic acid, pectin, and/or mixtures thereof. Methods for making porogens are well known in the art and non-limiting examples of such methods are described in, e.g., Peter X. Ma, Reverse Fabrication of Porous Materials, US 2002/00056000; P. X. Ma and G. Wei, Particle-Containing Complex Porous Materials, U.S. 2006/0246121; and F. Liu, et al., Porogen Compositions, Methods of Making and Uses, U.S. Provisional Patent Application No. 61/333,599, filed on May 11, 2010; each of which is hereby incorporated by reference in its entirety. Porogens are also commercially available from, e.g., Polyscience Inc. (Warrington, Pa.).

Porogens have a shape sufficient to allow formation of a porogen scaffold useful in making an elastomer matrix as disclosed herein. Any porogen shape is useful with the proviso that the porogen shape is sufficient to allow formation of a porogen scaffold useful in making an elastomer matrix as disclosed herein. Useful porogen shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

In an embodiment, porogens have a shape sufficient to allow formation of a porogen scaffold useful in making an elastomer matrix that allows tissue growth within its array of interconnected of pores. In aspects of this embodiment, porogens have a shape that is roughly spherical, perfectly spherical, ellipsoidal, polyhedronal, triangular, pyramidal, quadrilateral, or polygonal.

Porogens have a roundness sufficient to allow formation of a porogen scaffold useful in making an elastomer matrix as disclosed herein. As used herein, "roundness" is defined as $(6\times V)/(\pi \times D^3)$, where V is the volume and D is the diameter. Any porogen roundness is useful with the proviso that the porogen roundness is sufficient to allow formation of a porogen scaffold useful in making an elastomer matrix as disclosed herein.

In an embodiment, porogens has a roundness sufficient to allow formation of a porogen scaffold useful in making an elastomer matrix that allows tissue growth within its array of interconnected of pores. In aspects of this embodiment, porogens have a mean roundness of, e.g., about 0.1, about 0.2, about 0.3, about 0.4, about 0.5, about 0.6, about 0.7, about 0.8, about 0.9, or about 1.0. In other aspects of this embodiment, porogens have a mean roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, porogens have a mean roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, have a mean roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

The present specification discloses, in part, coating an elastomer base, for example, a base shell, for example, a smooth elastomer breast implant shell, with an elastomer coating and then applying to the elastomer coating, a coating of porogens to from an elastomer coated porogen mixture. Suitable elastomers and elastomer bases are as described above. Coating the porogens with an elastomer base can be accomplished by any suitable means, including, without limitation, mechanical application such as, e.g., dipping, spraying, knifing, curtaining, brushing, or vapor deposition, thermal application, adhering application, chemical bonding, self-assembling, molecular entrapment, and/or any combination thereof. The elastomer base is applied to the porogens in such a manner as to coat the porogens with the desired thickness of elastomer. Removal of excess elastomer can be accomplished by any suitable means, including, without limitation, gravity-based filtering or sieving, vacuum-based filtering or sieving, blowing, and/or any combination thereof.

Thus, in an embodiment, porogens are coated with an elastomer base to a thickness sufficient to allow formation of an elastomer matrix that allows tissue growth within its array of interconnected of pores. In aspects of this embodiment, porogens are coated with an elastomer base to a thickness of, e.g., about 1 μm, about 2 μm, about 3 μm, about 4 μm, about 5 μm, about 6 μm, about 7 μm, about 8 μm, about 9 μm, about 10 μm, about 20 μm, about 30 μm, about 40 μm, about 50 μm, about 60 μm, about 70 μm, about 80 μm, about 90 μm, or about 100 μm. In other aspects of this embodiment, porogens are coated with an elastomer base to a thickness of, e.g., at least 1 μm, at least 2 μm, at least 3 μm, at least 4 μm, at least 5 μm, at least 6 μm, at least 7 μm, at least 8 µm, at least 9 µm, at least 10 µm, at least 20 µm, at least 30 µm, at least 40 µm, at least 50 µm, at least 60 µm, at least 70 µm, at least 80 µm, at least 90 µm, or at least 100 µm. In yet other aspects of this embodiment, porogens are coated with an elastomer base to a thickness of, e.g., at most 1 µm, at most 2 µm, at most 3 µm, at most 4 µm, at most 5 µm, at most 6 µm, at most 7 µm, at most 8 µm, at most 9 µm, at most 10 µm, at most 20 µm, at most 30 µm, at most 40 µm, at most 50 µm, at most 60 µm, at most 70 µm, at most 80 µm, at most 90 µm, or at most 100 µm. In still other aspects of this embodiment, porogens are coated with an elastomer base to a thickness of, e.g., about 1 µm to about 5 µm, about 1 µm to about 10 µm, about 5 µm to about 10 µm, about 5 µm to about 25 µm, about 5 µm to about 50 µm, about 10 µm to about 50 µm, about 10 µm to about 75 µm, about 10 µm to about 100 µm, about 25 µm to about 100 µm, or about 50 µm to about 100 µm.

The present specification discloses, in part, devolatilizing an elastomer coated porogens. As used herein, the term "devolatilizing" or "devolatilization" refers to a process that removes volatile components from the elastomer coated porogens. Devolatilization of the elastomer coated porogens can be accomplished by any suitable means that substantially all the volatile components removed from the elastomer coated porogens. Non-limiting examples of devolatilizing procedures include evaporation, freeze-drying, sublimation, extraction, and/or any combination thereof.

In an embodiment, an elastomer base and/or elastomer coated porogen is devolatilized at a single temperature for a time sufficient to allow the evaporation of substantially all volatile components from the elastomer coated porogens. In aspects of this embodiment, an elastomer base and/or elastomer coated porogen is devolatilized at ambient temperature for e.g., about 1 minute to about 5 minutes, about 4 minutes to about 5 minutes, about 4.5 minutes to about 5.5 minutes, about 4 minutes to about 6 minutes, about 3 minutes to about 8 minutes, about 5 minutes to about 10 minutes, about 10 minutes to about 15 minutes, about 10 minutes to about 20 minutes, about 15 minutes to about 20 minutes, about 15 minutes to about 25 minutes, or about 19 minutes to about 21 minutes. In other aspects of this embodiment, an elastomer base and/or elastomer coated porogen is devolatilized at ambient temperature for e.g., about 20 minutes to about 45 minutes, about 25 minutes to about 35 minutes, about 30 minutes to about 45 minutes, about 30 minutes to about 60 minutes, about 25 minutes to about 35 minutes, about 29 minutes to about 31 minutes, or about 40 minutes to about 50 minutes. In another aspect of this embodiment, an elastomer base and/or elastomer coated porogen is devolatilized at ambient temperature for 45 minutes or more. In another aspect of this embodiment, an elastomer base and/or elastomer coated porogen is devolatilized at ambient temperature for about 45 minutes to about 75 minutes. In yet another aspect of this embodiment, an elastomer base and/or elastomer coated porogen is devolatilized at ambient temperature for about 90 minutes to about 150 minutes.

In another aspect of this embodiment, an elastomer base and/or elastomer coated porogen is devolatilized at about 18° C. to about 22° C. for about 1 minute to about 5 minutes. In yet another aspect of this embodiment, an elastomer base and/or elastomer coated porogen is devolatilized at about 18° C. to about 22° C. for about 4 minutes to about 6 minutes. In still another aspect of this embodiment, an elastomer base and/or elastomer coated porogen is devolatilized at about 18° C. to about 22° C. for about 4 minutes to about 5 minutes. In another aspect of this embodiment, an elastomer base and/or elastomer coated porogen is devolatilized at about 18° C. to about 22° C. for about 4.5 minutes to about 5.5 minutes. In another aspect of this embodiment, an elastomer base and/or elastomer coated porogen is devolatilized at about 18° C. to about 22° C. for about 45 minutes to about 75 minutes. In yet another aspect of this embodiment, an elastomer base and/or elastomer coated porogen is devolatilized at about 18° C. to about 22° C. for about 15 minutes to about 25 minutes. In still another aspect of this embodiment, an elastomer base and/or elastomer coated porogen is devolatilized at about 18° C. to about 22° C. for about 18 minutes to about 22 minutes. In another aspect of this embodiment, an elastomer base and/or elastomer coated porogen is devolatilized at about 18° C. to about 22° C. for about 21 minutes to about 23 minutes. In yet another aspect of this embodiment, an elastomer base and/or elastomer coated porogen is devolatilized at about 18° C. to about 22° C. for about 25 minutes to about 35 minutes. In still another aspect of this embodiment, an elastomer base and/or elastomer coated porogen is devolatilized at about 18° C. to about 22° C. for about 29 minutes to about 31 minutes. In still another aspect of this embodiment, an elastomer base and/or elastomer coated porogen is devolatilized at about 18° C. to about 22° C. for about 90 minutes to about 150 minutes.

In another aspect of this embodiment, an elastomer base and/or elastomer coated porogen is devolatilized at about 23° C. to about 27° C. for about 1 minute to about 5 minutes. In yet another aspect of this embodiment, an elastomer base and/or elastomer coated porogen is devolatilized at about 23° C. to about 27° C. for about 4 minutes to about 6 minutes. In still another aspect of this embodiment, an elastomer base and/or elastomer coated porogen is devolatilized at about 23° C. to about 27° C. for about 4 minutes to about 5 minutes. In another aspect of this embodiment, an elastomer base and/or elastomer coated porogen is devolatilized at about 23° C. to about 27° C. for about 4.5 minutes to about 5.5 minutes. In another aspect of this embodiment, an elastomer base and/or elastomer coated porogen is devolatilized at about 23° C. to about 27° C. for about 45 minutes to about 75 minutes. In yet another aspect of this embodiment, an elastomer base and/or elastomer coated porogen is devolatilized at about 23° C. to about 27° C. for about 15 minutes to about 25 minutes. In still another aspect of this embodiment, an elastomer base and/or elastomer coated porogen is devolatilized at about 23° C. to about 27° C. for about 18 minutes to about 22 minutes. In another aspect of this embodiment, an elastomer base and/or elastomer coated porogen is devolatilized at about 23° C. to about 27° C. for about 21 minutes to about 23 minutes. In yet another aspect of this embodiment, an elastomer base and/or elastomer coated porogen is devolatilized at about 23° C. to about 27° C. for about 25 minutes to about 35 minutes. In still another aspect of this embodiment, an elastomer base and/or elastomer coated porogen is devolatilized at about 23° C. to about 27° C. for about 29 minutes to about 31 minutes. In still another aspect of this embodiment, an elastomer base and/or elastomer coated porogen is devolatilized at about 23° C. to about 27° C. for about 90 minutes to about 150 minutes.

The present specification discloses, in part, packing porogens into a mold prior to fusion. Any mold shape may be used for packing the porogens. Porogens can be packed into the mold before coating of an uncured elastomer base, or can be first coated with an elastomer base before packing into a mold. If packed before coating, the porogens may be first treated to form a porogen scaffold before the addition of an uncured substance base. Alternatively, the porogens may be packed into the mold first, an uncured substance may then be added to the mold, and then the elastomer coated porogen mixture treated to form a porogen scaffold and cured substance. The elastomer coated porogen mixture may first have to be devolitilized before packing into a mold and/or before treating. The porogens and/or substance coated porogens may be packed into a mold using ultrasonic agitation, mechanical agitation, casting, or any other suitable method for obtaining a closely packed array of porogens.

A mold shape can be a shell that outlines the contours an implantable device, such as, e.g., a shell for a breast implant, a shell for a muscle implant, a tissue expander, a pacemaker, a defibrillator, any other tissue implant used for prosthetic, reconstructive, or aesthetic purposes, or any other implantable medical device. A mold shape can also be a three-dimensional form of a component or part whose shape the porous material is to represent. For instance, a mold shape can be shaped into a body part or portion of a body part, such as, e.g., a breast or portion thereof, an facial feature or portion thereof like a check, an ear, a nose or portion thereof, a muscle or portion thereof, a cartilage or portion thereof, a bone or portion thereof, a finger, a toe, or portion thereof, dura matter or portion thereof, any other soft tissue part or portion thereof, or any other implant used for prosthetic, reconstructive, or aesthetic purposes.

A mold shape can also be one that forms a sheet. Such sheets can be made in a wide variety or proportions based on the needed application. A sheet can be of any dimension or geometrical shape, such as, e.g., spherical, ellipsoidal, polyhedronal, triangular, pyramidal, quadrilateral like squares, rectangles, parallelograms, trapezoids, rhombus and kites, and other types of polygonal shapes. The thickness of a sheet may be of any thickness suitable for its application. Sheets can be made in a size slightly bigger that an implantable device so that there is sufficient material to cover the device and allow for trimming of the excess. As another example, the sheets can be produced as a continuous roll that allows a person skilled in the art to take only the desired amount for an application, such as, e.g., creating strips having a textured surface for control of scar formation.

The thickness of a sheet may be of any thickness suitable for its application. For example, a sheet may be from about 0.1 mm to about 1 mm, about 0.25 mm to about 1.5 mm, about 0.25 mm to about 2.5 mm, or about 0.5 mm to about 5 mm in thickness. In aspects of this embodiment, a sheet comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a sheet comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a sheet comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a sheet comprises a thickness of, e.g., about 100 µm to about 500 µm, about 100 µm to about 1 mm, about 100 µm to about 5 mm, about 300 µm to about 1 mm, about 300 µm to about 2 mm, about 300 µm to about 3 mm, about 300 µm to about 4 mm, about 300 µm to about 5 mm, about 500 µm to about 1 mm, about 500 µm to about 2 mm, about 500 µm to about 3 mm, about 500 µm to about 4 mm, about 500 µm to about 5 mm, about 800 µm to about 1 mm, about 800 µm to about 2 mm, about 800 µm to about 3 mm, about 800 µm to about 4 mm, about 800 µm to about 5 mm, about 1 mm to about 2 mm, about 1 mm to about 3 mm, about 1 mm to about 4 mm, about 1 mm to about 5 mm, or about 1.5 mm to about 3.5 mm.

In an embodiment, an elastomer coated porogen mixture is packed into a mold. In an aspect of this embodiment, an elastomer coated porogen mixture is packed into a mold in a manner suitable obtaining a closely packed array of porogens. In other aspects of this embodiment, an elastomer coated porogen mixture is packed into a mold using sonic agitation or mechanical agitation.

The present specification discloses, in part, treating an elastomer coated porogen mixture to allow fusing of the porogens to form a porogen scaffold and curing of the elastomer base. As used herein, the term "treating" refers to a process that 1) fuses the porogens to form a porogen scaffold useful to make an elastomer matrix as disclosed herein and/or 2) cures the elastomer base to form an elastomer matrix sufficient to allow tissue growth within its array of interconnected of pores as disclosed herein. As used herein, the term "curing" is synonymous with "setting" or "vulcanizing" and refers to a process that exposes the chains of a polymer to a element which activates a phase change in the polymer to a more stable state, such as, e.g., by physically or chemically cross-linked polymer chains to one another. Non-limiting examples of treating include thermal treating, chemical treating, catalyst treating, radiation treating, and physical treating. Treating of an elastomer coated porogen scaffold can be done under any condition for any length of time with the proviso that the treating fuses the porogens to form a porogen scaffold useful to make an elastomer matrix as disclosed herein and cures an elastomer to form an elastomer matrix sufficient to allow tissue growth within its array of interconnected of pores as disclosed herein.

Thermal treating an elastomer coated porogen mixture can be at any temperature or temperatures for any length of time or times with the proviso that the thermal treatment fuses the porogens to form a porogen scaffold and cures the elastomer base to form an elastomer matrix as disclosed herein. A non-limiting example of temperatures useful in a thermal treatment are temperatures higher than the glass transition temperature or melting temperature of the porogens, such as between about 5° C. to about 50° C. higher than the glass transition temperature or melting temperature of the porogens. Any temperature can be used in a thermal treatment with the proviso that the temperature is sufficient to cause fusion of the porogens. As a non-limiting example, the thermal treatment can be from about 30° C. to about 250° C. Increasing the duration of the thermal treatment at a given temperature increases the connection size; increases the sintering temperature, and increases the growth rate of the connections. Any time can be used in a thermal treatment with the proviso that the time is sufficient to cause fusion of the porogens and cures the elastomer base. Suitable times are generally from about 0.5 hours to about 48 hours.

Thus, in an embodiment, elastomer coated porogens are treated by thermal treatment, chemical treatment, catalyst treatment, radiation treatment, or physical treatment. In another embodiment, elastomer coated porogens are treated at a single time, where the curing time is sufficient to form an elastomer matrix sufficient to allow tissue growth within its array of interconnected of pores.

In another embodiment, elastomer coated porogens are thermal treated at a single temperature for a single time, where the treating temperature and time is sufficient to fuse the porogens to form a porogen scaffold and cure the elastomer base to form an elastomer matrix sufficient to allow tissue growth within its array of interconnected of pores.

In other aspects of this embodiment, a thermal treatment comprises heating an elastomer coated porogens for a time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperature and time is sufficient to fuse the porogens to form a porogen scaffold and cure the elastomer base to form an elastomer matrix sufficient to allow tissue growth within its array of interconnected of pores. In yet other aspects of this embodiment, a thermal treatment comprises heating an elastomer coated porogens for a time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperature and time is sufficient to fuse the porogens to form a porogen scaffold and cure the elastomer base to form an elastomer matrix sufficient to allow tissue growth within its array of interconnected of pores. In still other aspects of this embodiment, a thermal treatment comprises heating an elastomer coated porogens for a time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperature and time is sufficient to fuse the porogens to form a porogen scaffold and cure the elastomer base to form an elastomer matrix sufficient to allow tissue growth within its array of interconnected of pores. In further aspects of this embodiment, a thermal treatment comprises heating an elastomer coated porogens for a time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperature and time is sufficient to fuse the porogens to form a porogen scaffold and cure the elastomer base to form an elastomer matrix sufficient to allow tissue growth within its array of interconnected of pores.

In another aspect of this embodiment, the thermal treatment comprises heating an elastomer coated porogen scaffold is treated at about 30° C. to about 140° C. for about 10 minutes to about 360 minutes, where the treating temperature and time is sufficient to fuse the porogens to form a porogen scaffold and cure the elastomer base to form an elastomer matrix sufficient to allow tissue growth within its array of interconnected of pores. In another aspect of this embodiment, the thermal treatment comprises heating an elastomer coated porogen scaffold is treated at about 110° C. to about 140° C. for about 65 minutes to about 105 minutes, where the treating temperature and time is sufficient to fuse the porogens to form a porogen scaffold and cure the elastomer base to form an elastomer matrix sufficient to allow tissue growth within its array of interconnected of pores. In another aspect of this embodiment, the thermal treatment comprises heating an elastomer coated porogen scaffold is treated at about 115° C. to about 135° C. for about 75 minutes to about 95 minutes, where the treating temperature and time is sufficient to fuse the porogens to form a porogen scaffold and cure the elastomer base to form an elastomer matrix sufficient to allow tissue growth within its array of interconnected of pores. In another aspect of this embodiment, the thermal treatment comprises heating an elastomer coated porogen scaffold is treated at about 120° C. to about 130° C. for about 80 minutes to about 90 minutes, where the treating temperature and time is sufficient to fuse the porogens to form a porogen scaffold and cure the elastomer base to form an elastomer matrix sufficient to allow tissue growth within its array of interconnected of pores. In another aspect of this embodiment, the thermal treatment comprises heating an elastomer coated porogen scaffold is treated at about 126° C. for about 85 minutes, where the treating temperature and time is sufficient to fuse the porogens to form a porogen scaffold and cure the elastomer base to form an elastomer matrix sufficient to allow tissue growth within its array of interconnected of pores. In another aspect of this embodiment, the thermal treatment comprises heating an elastomer coated porogen scaffold is treated at about 126° C. for about 75 minutes, where the treating temperature and time is sufficient to fuse the porogens to form a porogen scaffold and cure the elastomer base to form an elastomer matrix sufficient to allow tissue growth within its array of interconnected of pores.

In yet another embodiment, elastomer coated porogens are thermal treated at a plurality of temperatures for a plurality of times, where the treating temperatures and times are sufficient to fuse the porogens to form a porogen scaffold and cure the elastomer base to form an elastomer matrix sufficient to allow tissue growth within its array of interconnected of pores. In an aspect of this embodiment, elastomer coated porogens are treated at a first temperature for a first time, and then a second temperature for a second time, where the treating temperatures and times are sufficient to fuse the porogens to form a porogen scaffold and cure the elastomer base to form an elastomer matrix sufficient to allow tissue growth within its array of interconnected of pores, and where the first and second temperatures are different.

In aspects of this embodiment, thermal treatment comprises heating the elastomer coated porogens at a first temperature for a first time, and then heating the porogens at a second temperature for a second time, where the treating temperatures and times are sufficient to fuse the porogens to form a porogen scaffold and cure the elastomer base to form an elastomer matrix sufficient to allow tissue growth within its array of interconnected of pores, and where the first and second temperatures are different, and where the first and second temperatures are different. In other aspects of this embodiment, a thermal treatment comprises heating an elastomer coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the elastomer coated porogens, then heating for a second time the porogens at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first and second temperatures are different. In yet other aspects of this embodiment, a thermal treatment comprises heating an elastomer coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating the elastomer coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first and second temperatures are different. In still other aspects of this embodiment, a thermal treatment comprises heating an elastomer coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating the elastomer coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first and second temperatures are different.

In further aspects of this embodiment, a thermal treatment comprises heating an elastomer coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating the elastomer coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first and second temperatures are different.

In other aspects of this embodiment, thermal treatment comprises heating the elastomer coated porogens at a first temperature for a first time, heating the porogens at a second temperature for a second time, and then heating the porogens at a third temperature at a third time, where the treating temperatures and times are sufficient to fuse the porogens to form a porogen scaffold and cure the elastomer base to form an elastomer matrix sufficient to allow tissue growth within its array of interconnected of pores, and where the first temperature is different from the second temperature and the second temperature is different from the third temperature.

In other aspects of this embodiment, a thermal treatment comprises heating an elastomer coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating the elastomer coated porogens for a second time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating the elastomer coated porogens for a third time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first temperature is different from the second temperature and the second temperature is different from the third temperature. In yet other aspects of this embodiment, a thermal treatment comprises heating an elastomer coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating the elastomer coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating the elastomer coated porogens for a third time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first temperature is different from the second temperature and the second temperature is different from the third temperature. In still other aspects of this embodiment, a thermal treatment comprises heating an elastomer coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating the elastomer coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating the elastomer coated porogens for a third time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first temperature is different from the second temperature and the second temperature is different from the third temperature.

In further aspects of this embodiment, a thermal treatment comprises heating an elastomer coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating the elastomer coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating the elastomer coated porogens for a third time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure the elastomer base to form an elastomer matrix sufficient to allow tissue growth within its array of interconnected of pores, and where the first temperature is different from the second temperature and the second temperature is different from the third temperature.

In still other aspect of this embodiment, elastomer coated porogens are treated at about 60° C. to about 75° C. for about 15 minutes to about 45 minutes, and then at about 120° C. to about 130° C. for about 60 minutes to about 90 minutes, where the treating temperatures and times is sufficient to fuse the porogens to form a porogen scaffold and cure the elastomer base to form an elastomer matrix sufficient to allow tissue growth within its array of interconnected of pores. In a further aspect of this embodiment, elastomer coated porogen mixture is treated at about 60° to about 75° C. for about 15 minutes to about 45 minutes, then at about 135° C. to about 150° C. for about 90 minutes to about 150 minutes, and then at about 150° C. to about 165° C. for about 15 minutes to about 45 minutes.

The present specification discloses, in part, to form a porogen scaffold. As used herein, the term "porogen scaffold" refers to a three-dimensional structural framework composed of fused porogens that serves as the negative replica of the elastomer matrix defining an interconnected array or pores as disclosed herein.

The porogen scaffold is formed in such a manner that substantially all the fused porogens in the porogen scaffold have a similar diameter. As used herein, the term "substantially," when used to describe fused porogen, refers to at least 90% of the porogen comprising the porogen scaffold are fused, such as, e.g., at least 95% of the porogens are fused or at least 97% of the porogen are fused. As used herein, the term "similar diameter," when used to describe fused porogen, refers to a difference in the diameters of the two fused porogen that is less than about 20% of the larger diameter. As used herein, the term "diameter," when used to describe fused porogen, refers to the longest line segment that can be drawn that connects two points within the fused porogen, regardless of whether the line passes outside the boundary of the fused porogen. Any fused porogen diameter is useful with the proviso that the fused porogen diameter is sufficient to allow formation of a porogen scaffold useful in making an elastomer matrix as disclosed herein.

The porogen scaffold is formed in such a manner that the diameter of the connections between each fused porogen is sufficient to allow formation of a porogen scaffold useful in making an elastomer matrix as disclosed herein. As used herein, the term "diameter," when describing the connection between fused porogens, refers to the diameter of the cross-section of the connection between two fused porogens in the plane normal to the line connecting the centroids of the two fused porogens, where the plane is chosen so that the area of the cross-section of the connection is at its minimum value. As used herein, the term "diameter of a cross-section of a connection" refers to the average length of a straight-line segment that passes through the center, or centroid (in the case of a connection having a cross-section that lacks a center), of the cross-section of a connection and terminates at the periphery of the cross-section. As used herein, the term "substantially," when used to describe the connections between fused porogens refers to at least 90% of the fused porogens comprising the porogen scaffold make connections between each other, such as, e.g., at least 95% of the fused porogens make connections between each other or at least 97% of the fused porogens make connections between each other.

In an embodiment, a porogen scaffold comprises fused porogens where substantially all the fused porogens have a similar diameter. In aspects of this embodiment, at least 90% of all the fused porogens have a similar diameter, at least 95% of all the fused porogens have a similar diameter, or at least 97% of all the fused porogens have a similar diameter. In another aspect of this embodiment, difference in the diameters of two fused porogens is, e.g., less than about 20% of the larger diameter, less than about 15% of the larger diameter, less than about 10% of the larger diameter, or less than about 5% of the larger diameter.

In another embodiment, a porogen scaffold comprises fused porogens have a mean diameter sufficient to allow tissue growth into the array of interconnected porogens. In aspects of this embodiment, a porogen scaffold comprises fused porogens comprising mean fused porogen diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen scaffold comprises fused porogens comprising mean fused porogen diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen scaffold comprises fused porogens comprising mean fused porogen diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, an elastomer matrix comprises fused porogens comprising mean fused porogen diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen scaffold comprises fused porogens comprising mean fused porogen diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, an elastomer matrix comprises fused porogens comprising mean fused porogen diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen scaffold comprises fused porogens comprising mean fused porogen diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 400 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porogen scaffold comprises fused porogens connected to a plurality of other porogens. In aspects of this embodiment, a porogen scaffold comprises a mean fused porogen connectivity, e.g., about two other fused porogens, about three other fused porogens, about four other fused porogens, about five other fused porogens, about six other fused porogens, about seven other fused porogens, about eight other fused porogens, about nine other fused porogens, about ten other fused porogens, about 11 other fused porogens, or about 12 other fused porogens. In other aspects of this embodiment, a porogen scaffold comprises a mean fused porogen connectivity, e.g., at least two other fused porogens, at least three other fused porogens, at least four other fused porogens, at least five other fused porogens, at least six other fused porogens, at least seven other fused porogens, at least eight other fused porogens, at least nine other fused porogens, at least ten other fused porogens, at least 11 other fused porogens, or at least 12 other fused porogens. In yet other aspects of this embodiment, a porogen scaffold comprises a mean fused porogen connectivity, e.g., at most two other fused porogens, at most three other fused porogens, at most four other fused porogens, at most five other fused porogens, at most six other fused porogens, at most seven other fused porogens, at most eight other fused porogens, at most nine other fused porogens, at most ten other fused porogens, at most 11 other fused porogens, or at most 12 other fused porogens.

In still other aspects of this embodiment, a porogen scaffold comprises fused porogens connected to, e.g., about two other fused porogens to about 12 other fused porogens, about two other fused porogens to about 11 other fused porogens, about two other fused porogens to about ten other fused porogens, about two other fused porogens to about nine other fused porogens, about two other fused porogens to about eight other fused porogens, about two other fused porogens to about seven other fused porogens, about two other fused porogens to about six other fused porogens, about two other fused porogens to about five other fused porogens, about three other fused porogens to about 12 other fused porogens, about three other fused porogens to about 11 other fused porogens, about three other fused porogens to about ten other fused porogens, about three other fused porogens to about nine other fused porogens, about three other fused porogens to about eight other fused porogens, about three other fused porogens to about seven other fused porogens, about three other fused porogens to about six other fused porogens, about three other fused porogens to about five other fused porogens, about four other fused porogens to about 12 other fused porogens, about four other fused porogens to about 11 other fused porogens, about four other fused porogens to about ten other fused porogens, about four other fused porogens to about nine other fused porogens, about four other fused porogens to about eight other fused porogens, about four other fused porogens to about seven other fused porogens, about four other fused porogens to about six other fused porogens, about four other fused porogens to about five other fused porogens, about five other fused porogens to about 12 other fused porogens, about five other fused porogens to about 11 other fused porogens, about five other fused porogens to about ten other fused porogens, about five other fused porogens to about nine other fused porogens, about five other fused porogens to about eight other fused porogens, about five other fused porogens to about seven other fused porogens, or about five other fused porogens to about six other fused porogens.

In another embodiment, a porogen scaffold comprises fused porogens where the diameter of the connections between the fused porogens is sufficient to allow formation of a porogen scaffold useful in making an elastomer matrix that allows tissue growth within its array of interconnected of pores. In aspects of this embodiment, the porogen scaffold comprises fused porogens where the diameter of the connections between the fused porogens is, e.g., about 10% the mean fused porogen diameter, about 20% the mean fused porogen diameter, about 30% the mean fused porogen diameter, about 40% the mean fused porogen diameter, about 50% the mean fused porogen diameter, about 60% the mean fused porogen diameter, about 70% the mean fused porogen diameter, about 80% the mean fused porogen diameter, or about 90% the mean fused porogen diameter. In other aspects of this embodiment, the porogen scaffold comprises fused porogens where the diameter of the connections between the fused porogens is, e.g., at least 10% the mean fused porogen diameter, at least 20% the mean fused porogen diameter, at least 30% the mean fused porogen diameter, at least 40% the mean fused porogen diameter, at least 50% the mean fused porogen diameter, at least 60% the mean fused porogen diameter, at least 70% the mean fused porogen diameter, at least 80% the mean fused porogen diameter, or at least 90% the mean fused porogen diameter. In yet other aspects of this embodiment, the porogen scaffold comprises fused porogens where the diameter of the connections between the fused porogens is, e.g., at most 10% the mean fused porogen diameter, at most 20% the mean fused porogen diameter, at most 30% the mean fused porogen diameter, at most 40% the mean fused porogen diameter, at most 50% the mean fused porogen diameter, at most 60% the mean fused porogen diameter, at most 70% the mean fused porogen diameter, at most 80% the mean fused porogen diameter, or at most 90% the mean fused porogen diameter.

In still other aspects of this embodiment, a porogen scaffold comprises fused porogens where the diameter of the connections between the fused porogens is, e.g., about 10% to about 90% the mean fused porogen diameter, about 15% to about 90% the mean fused porogen diameter, about 20% to about 90% the mean fused porogen diameter, about 25% to about 90% the mean fused porogen diameter, about 30% to about 90% the mean fused porogen diameter, about 35% to about 90% the mean fused porogen diameter, about 40% to about 90% the mean fused porogen diameter, about 10% to about 90% the mean fused porogen diameter, about 15% to about 80% the mean fused porogen diameter, about 20% to about 80% the mean fused porogen diameter, about 25% to about 80% the mean fused porogen diameter, about 30% to about 80% the mean fused porogen diameter, about 35% to about 80% the mean fused porogen diameter, about 40% to about 80% the mean fused porogen diameter, about 10% to about 80% the mean fused porogen diameter, about 15% to about 70% the mean fused porogen diameter, about 20% to about 70% the mean fused porogen diameter, about 25% to about 70% the mean fused porogen diameter, about 30% to about 70% the mean fused porogen diameter, about 35% to about 70% the mean fused porogen diameter, about 40% to about 70% the mean fused porogen diameter, about 10% to about 70% the mean fused porogen diameter, about 15% to about 60% the mean fused porogen diameter, about 20% to about 60% the mean fused porogen diameter, about 25% to about 60% the mean fused porogen diameter, about 30% to about 60% the mean fused porogen diameter, about 35% to about 60% the mean fused porogen diameter, about 40% to about 60% the mean fused porogen diameter, about 10% to about 60% the mean fused porogen diameter, about 15% to about 50% the mean fused porogen diameter, about 20% to about 50% the mean fused porogen diameter, about 25% to about 50% the mean fused porogen diameter, about 30% to about 50% the mean fused porogen diameter, about 10% to about 50% the mean fused porogen diameter, about 15% to about 40% the mean fused porogen diameter, about 20% to about 40% the mean fused porogen diameter, about 25% to about 40% the mean fused porogen diameter, or about 30% to about 40% the mean fused porogen diameter.

The present specification discloses, in part, removing a porogen scaffold from a cured elastomer. Removal of the porogen scaffold can be accomplished by any suitable means, with the proviso that the resulting porous material comprises a substantially non-degradable, biocompatible, elastomer matrix defining an array of interconnected pores useful in allowing substantial tissue growth into the interconnected pores in a time sufficient to reduce or prevent formation of fibrous capsules that can result in capsular contracture or scarring. As such, the resulting elastomer matrix should support aspects of tissue growth such as, e.g., cell migration, cell proliferation, cell differentiation, nutrient exchange, and/or waste removal. Non-limiting examples of porogen removal include solvent extraction, thermal decomposition extraction, degradation extraction, mechanical extraction, and/or any combination thereof. The resulting porous material comprising a substantially non-degradable, biocompatible, an elastomer matrix defining an array of interconnected pores is as described above in the present specification. In extraction methods requiring exposure to another solution, such as, e.g., solvent extraction, the extraction can incorporate a plurality of solution changes over time to facilitate removal of the porogen scaffold. Non-limiting examples of solvents useful for solvent extraction include water, methylene chloride, acetic acid, formic acid, pyridine, tetrahydrofuran, dimethylsulfoxide, dioxane, benzene, and/or mixtures thereof. A mixed solvent can be in a ratio of higher than about 1:1, first solvent to second solvent or lower than about 1:1, first solvent to second solvent.

In an embodiment, a porogen scaffold is removed by extraction, where the extraction removes substantially all the porogen scaffold leaving an elastomer matrix defining an array of interconnected pores. In aspects of this embodiment, a porogen scaffold is removed by extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold. In an aspect, a porogen scaffold is removed by a solvent extraction, a thermal decomposition extraction, a degradation extraction, a mechanical extraction, and/or any combination thereof In another embodiment, a porogen scaffold is removed by solvent extraction, where the extraction removes substantially all the porogen scaffold leaving an elastomer matrix defining an array of interconnected pores. In aspects of this embodiment, a porogen scaffold is removed by solvent extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by solvent extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by solvent extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In yet another embodiment, a porogen scaffold is removed by thermal decomposition extraction, where the extraction removes substantially all the porogen scaffold leaving an elastomer matrix defining an array of interconnected pores. In aspects of this embodiment, a porogen scaffold is removed by thermal extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by thermal extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by thermal extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by degradation extraction, where the extraction removes substantially all the porogen scaffold leaving an elastomer matrix defining an array of interconnected pores. In aspects of this embodiment, a porogen scaffold is removed by degradation extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by degradation extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by degradation extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by mechanical extraction, where the extraction removes substantially all the porogen scaffold leaving an elastomer matrix defining an array of interconnected pores. In aspects of this embodiment, a porogen scaffold is removed by mechanical extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by mechanical extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by mechanical extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In another embodiment, a porogen scaffold is removed by soaking in water. Removal of a porogen scaffold by soaking in water can be accomplished by a single cycle of soaking or a plurality of soaking cycles. One or more rinsing cycle using water may be performed after one, one or more, or all soaking cycles. In an aspect of this embodiment, removing a porogen scaffold from a cured elastomer may be accomplished by soaking in water for about 5 to about 30 minutes and then rinsing the resulting porous material. In another aspect of this embodiment, removing a porogen scaffold from a cured elastomer may be accomplished by soaking in water for about 5 to about 30 minutes, rinsing the resulting porous material, soaking in water for about 5 to about 30 minutes, and then rinsing the resulting porous material. In yet another aspect of this embodiment, removing a porogen scaffold from a cured elastomer may be accomplished by soaking in water for about 5 to about 30 minutes, rinsing the resulting porous material, soaking in water for about 5 to about 30 minutes, rinsing the resulting porous material, soaking in water for about 5 to about 30 minutes, and then rinsing the resulting porous material.

In an aspect of this embodiment, removing a porogen scaffold from a cured elastomer may be accomplished by soaking in about 30° C. to about 60° C. water for about 5 to about 30 minutes and then rinsing the resulting porous material. In another aspect of this embodiment, removing a porogen scaffold from a cured elastomer may be accomplished by soaking in about 30° C. to about 60° C. water for about 5 to about 30 minutes, rinsing the resulting porous material, soaking in about 30° C. to about 60° C. water for about 5 to about 30 minutes, and then rinsing the resulting porous material. In yet another aspect of this embodiment, removing a porogen scaffold from a cured elastomer may be accomplished by soaking in about 30° C. to about 60° C. water for about 5 to about 30 minutes, rinsing the resulting porous material, soaking in about 30° C. to about 60° C. water for about 5 to about 30 minutes, rinsing the resulting porous material, soaking in about 30° C. to about 60° C. water for about 5 to about 30 minutes, and then rinsing the resulting porous material. In other aspects, the rinsing is done in water less than 45° C., less than 40° C., less than 35° C., less than 30° C., less than 25° C., less than 20° C., or less than 15° C. In other aspects, the rinsing is done in water less than 45° C., less than 40° C., less than 35° C., less than 30° C., less than 25° C., less than 20° C., or less than 15° C. for about 1 minute to about 5 minutes, about 3 minute to about 7 minutes, or about 5 minute to about 10 minutes.

In an aspect of this embodiment, removing a porogen scaffold from a cured elastomer may be accomplished by soaking in about 40° C. to about 50° C. water for about 5 to about 30 minutes and then rinsing the resulting porous material. In another aspect of this embodiment, removing a porogen scaffold from a cured elastomer may be accomplished by soaking in about 40° C. to about 50° C. water for about 5 to about 30 minutes, rinsing the resulting porous material, soaking in about 40° C. to about 50° C. water for about 5 to about 30 minutes, and then rinsing the resulting porous material. In yet another aspect of this embodiment, removing a porogen scaffold from a cured elastomer may be accomplished by soaking in about 40° C. to about 50° C. water for about 5 to about 30 minutes, rinsing the resulting porous material, soaking in about 40° C. to about 50° C. water for about 5 to about 30 minutes, rinsing the resulting porous material, soaking in about 40° C. to about 50° C. water for about 5 to about 30 minutes, and then rinsing the resulting porous material. In other aspects, the rinsing is done in water less than 45° C., less than 40° C., less than 35° C., less than 30° C., less than 25° C., less than 20° C., or less than 15° C. In other aspects, the rinsing is done in water less than 45° C., less than 40° C., less than 35° C., less than 30° C., less than 25° C., less than 20° C., or less than 15° C. for about 1 minute to about 5 minutes, about 3 minute to about 7 minutes, or about 5 minute to about 10 minutes.

In an aspect of this embodiment, removing a porogen scaffold from a cured elastomer may be accomplished by soaking in about 44° C. to about 46° C. water for about 5 to about 30 minutes and then rinsing the resulting porous material. In another aspect of this embodiment, removing a porogen scaffold from a cured elastomer may be accomplished by soaking in about 44° C. to about 46° C. water for about 5 to about 30 minutes, rinsing the resulting porous material, soaking in about 40° C. to about 50° C. water for about 5 to about 30 minutes, and then rinsing the resulting porous material. In yet another aspect of this embodiment, removing a porogen scaffold from a cured elastomer may be accomplished by soaking in about 44° C. to about 46° C. water for about 5 to about 30 minutes, rinsing the resulting porous material, soaking in about 44° C. to about 46° C. water for about 5 to about 30 minutes, rinsing the resulting porous material, soaking in about 44° C. to about 46° C. water for about 5 to about 30 minutes, and then rinsing the resulting porous material. In other aspects, the rinsing is done in water less than 45° C., less than 40° C., less than 35° C., less than 30° C., less than 25° C., less than 20° C., or less than 15° C. In other aspects, the rinsing is done in water less than 45° C., less than 40° C., less than 35° C., less than 30° C., less than 25° C., less than 20° C., or less than 15° C. for about 1 minute to about 5 minutes, about 3 minute to about 7 minutes, or about 5 minute to about 10 minutes.

The present specification discloses in part, biocompatible implantable device comprising a layer of porous material as disclosed herein, wherein the porous material covers a surface of the device. See, e.g., FIG. 2, FIGS. 4-8. As used herein, the term "implantable" refers to any material that can be embedded into, or attached to, tissue, muscle, organ or any other part of an animal body. As used herein, the term "animal" includes all mammals including a human. A biocompatible implantable device is synonymous with "medical device," "biomedical device," "implantable medical device" or "implantable biomedical device" and includes, without limitation, pacemakers, dura matter substitutes, implantable cardiac defibrillators, tissue expanders, and tissue implants used for prosthetic, reconstructive, or aesthetic purposes, like breast implants, muscle implants or implants that reduce or prevent scarring. Examples of biocompatible implantable devices that the porous material disclosed herein can be attached to are described in, e.g., Schuessler, Rotational Molding System for Medical Articles, U.S. Pat. No. 7,628,604; Smith, Mastopexy Stabilization Apparatus and Method, U.S. Pat. No. 7,081,135; Knisley, Inflatable Prosthetic Device, U.S. Pat. No. 6,936,068; Falcon, Reinforced Radius Mammary Prostheses and Soft Tissue Expanders, U.S. Pat. No. 6,605,116; Schuessler, Rotational Molding of Medical Articles, U.S. Pat. No. 6,602,452; Murphy, Seamless Breast Prosthesis, U.S. Pat. No. 6,074,421; Knowlton, Segmental Breast Expander For Use in Breast Reconstruction, U.S. Pat. No. 6,071,309; VanBeek, Mechanical Tissue Expander, U.S. Pat. No. 5,882,353; Hunter, Soft Tissue Implants and Anti-Scarring Agents, Schuessler, Self-Sealing Shell For Inflatable Prostheses, U.S. Patent Publication 2010/0049317; U.S. 2009/0214652; Schraga, Medical Implant Containing Detection Enhancing Agent and Method For Detecting Content Leakage, U.S. Patent Publication 2009/0157180; Schuessler, All-Barrier Elastomeric Gel-Filled Breast Prosthesis, U.S. Patent Publication 2009/0030515; Connell, Differential Tissue Expander Implant, U.S. Patent Publication 2007/0233273; and Hunter, Medical implants and Anti-Scarring Agents, U.S. Patent Publication 2006/0147492; Van Epps, Soft Filled Prosthesis Shell with Discrete Fixation Surfaces, International Patent Publication WO/2010/019761; Schuessler, Self Sealing Shell for Inflatable Prosthesis, International Patent Publication WO/2010/022130; Yacoub, Prosthesis Implant Shell, International Patent Publication WO/2010/045581, each of which is hereby incorporated by reference in its entirety.

A biocompatible implantable device disclosed herein can be implanted into the soft tissue of an animal during the normal operation of the device. Such implantable devices may be completely implanted into the soft tissue of an animal body (i.e., the entire device is implanted within the body), or the device may be partially implanted into an animal body (i.e., only part of the device is implanted within an animal body, the remainder of the device being located outside of the animal body). A biocompatible implantable device disclosed herein can also be affixed to soft tissue of an animal during the normal operation of the medical device. Such devices are typically affixed to the skin of an animal body.

The present specification discloses, in part, a porous material that covers a surface of the biocompatible implantable device. Any of the porous materials disclosed herein can be used as the porous material covering a surface of a biocompatible implantable device. In general, the surface of a biocompatible implantable device is one exposed to the surrounding tissue of an animal in a manner that promotes tissue growth, and/or reduces or prevents formation of fibrous capsules that can result in capsular contracture or scarring.

A biocompatible implantable device may be a base shell comprising a single layer or a plurality of layers. In an aspect of this embodiment, a base shell comprises one or more inner base layer of an elastomer, a barrier or reinforcement layer and one or more outer base layer of an elastomer, wherein the barrier or reinforcement layer lays in between the one or more inner base layers and one or more outer base layers. In another aspect of this embodiment, a base shell comprises one inner base layer of an elastomer, a barrier or reinforcement layer and two outer base layer of an elastomer. In yet another aspect of this embodiment, a base shell comprises two inner base layers of an elastomer, a barrier or reinforcement layer and two outer base layers of an elastomer. In still another aspect of this embodiment, a base shell comprises two inner base layers of an elastomer, a barrier or reinforcement layer and three outer base layers of an elastomer. The barrier or reinforcement layer may comprise a synthetic polymer mesh or fabric. Exemplary base shells include, without limitation, a breast implant shell or a tissue expander shell.

Thus, in an embodiment, a porous material covers the entire surface of a biocompatible implantable device. In another embodiment, a porous material covers a portion of a surface of a biocompatible implantable device. In aspects of this embodiment, a porous material covers to a front surface of a biocompatible implantable device or a back surface of a biocompatible implantable device. In other aspects, a porous material covers only to, e.g., about 20%, about 30%, about 40%, about 50%, about 60%, about 70% about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70% at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70% at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material covering a biocompatible implantable device can be of any thickness with the proviso that the material thickness allows tissue growth within the array of interconnected of pores of an elastomer matrix in a manner sufficient to reduce or prevent formation of fibrous capsules that can result in capsular contracture or scarring.

Thus, in an embodiment, a layer of porous material covering a biocompatible implantable device is of a thickness that allows tissue growth within the array of interconnected of pores of an elastomer matrix in a manner sufficient to reduce or prevent formation of fibrous capsules that can result in capsular contracture or scarring. In aspects of this embodiment, a layer porous material covering a biocompatible implantable device comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a layer porous material covering a biocompatible implantable device comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer porous material covering a biocompatible implantable device comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer porous material covering a biocompatible implantable device comprises a thickness of, e.g., about 100 µm to about 500 µm, about 100 µm to about 1 mm, about 100 µm to about 5 mm, about 300 µm to about 1 mm, about 300 µm to about 2 mm, about 300 µm to about 3 mm, about 300 µm to about 4 mm, about 300 µm to about 5 mm, about 500 µm to about 1 mm, about 500 µm to about 2 mm, about 500 µm to about 3 mm, about 500 µm to about 4 mm, about 500 µm to about 5 mm, about 800 µm to about 1 mm, about 800 µm to about 2 mm, about 800 µm to about 3 mm, about 800 µm to about 4 mm, about 800 µm to about 5 mm, about 1 mm to about 2 mm, about 1 mm to about 3 mm, about 1 mm to about 4 mm, about 1 mm to about 5 mm, or about 1.5 mm to about 3.5 mm.

The present specification discloses in part, a method for making biocompatible implantable device comprising a porous material. In an aspect, a method for making biocompatible implantable device comprises the step of attaching a porous material to the surface of a biocompatible implantable device. In another aspect, a method for making biocompatible implantable device comprises the steps of a) preparing a surface of a biocompatible implantable device to receive porous material; b) attaching a porous material to the prepared surface of the device. Any of the porous materials disclosed herein can be used as the porous material attached to a surface of a biocompatible implantable device.

In yet another aspect, a method for making biocompatible implantable device comprising the step of: a) coating a mandrel with an elastomer base; b) curing the elastomer base to form a base layer; c) coating the cured base layer with an elastomer base; d) coating the elastomer base with porogens to form an elastomer coated porogen mixture; e) treating the elastomer coated porogen mixture to form a porogen scaffold comprising fused porogens and cure the elastomer; and f) removing the porogen scaffold, wherein porogen scaffold removal results in a porous material, the porous material comprising a non-degradable, biocompatible, elastomer matrix defining an array of interconnected pores. In this method steps (c) and (d) can be repeated multiple times until the desired thickness of the material layer is achieved.

The present specification discloses, in part, preparing a surface of a biocompatible implantable device to receive porous material. Preparing a surface of a biocompatible implantable device to receive porous material can be accomplished by any technique that does not destroy the desired properties of the porous material or the biocompatible implantable device. As a non-limiting example, a surface of a biocompatible implantable device can be prepared by applying a bonding substance. Non-limiting examples of bonding substances include silicone adhesives, such as, e.g., RTV silicone and HTV silicone. The bonding substance is applied to the surface of a biocompatible implantable device, the porous material, or both, using any method known in the art, such as, e.g., cast coating, spray coating, dip coating, curtain coating, knife coating, brush coating, vapor deposition coating, and the like.

The present specification discloses, in part, attaching a porous material to a surface of a biocompatible implantable device. The porous material can be attached to the entire surface of the device, or only to portions of the surface of the device. As a non-limiting example, porous material is attached only to the front surface of the device or only the back surface of the device. Attachment of a porous material to a surface of a biocompatible implantable device can be accomplished by any technique that does not destroy the desired properties of the porous material or the biocompatible implantable device.

For example, attachment can occur by adhering an already formed porous material onto a surface of a biocompatible implantable device using methods known in the art, such as, e.g., gluing, bonding, melting. For instance, a dispersion of silicone is applied as an adhesive onto a surface of a biocompatible implantable device, a porous material sheet, or both, and then the two materials are placed together in a manner that allows the adhesive to attached the porous material to the surface of the device in such a way that there are no wrinkles on the surface of the device. The silicone adhesive is allowed to cure and then the excess material is cut off creating a uniform seam around the device. This process results in a biocompatible implantable device comprising a porous material disclosed herein. Examples 2 and 4 illustrate method of this type of attachment.

Alternatively, attachment can occur by forming the porous material directly onto a surface of a biocompatible implantable device using methods known in the art, such as, e.g., cast coating, spray coating, dip coating, curtain coating, knife coating, brush coating, vapor deposition coating, and the like. For instance, an elastomer base is applied to a mandrel and cured to form a base layer of cured elastomer. The base layer is then initially coated with an elastomer base and then subsequently with porogens to create a elastomer coated porogen mixture. This mixture is then treated as disclosed herein to form a porogen scaffold and cure the elastomer. The porogen scaffold is then removed, leaving a layer of porous material on the surface of the device. The thickness of the porous material layer can be increased by repeated coatings of additional elastomer base and porogens. Examples 5-8 illustrate method of this type of attachment.

Regardless of the method of attachment, the porous material can be applied to the entire surface of a biocompatible implantable device, or only to portions of the surface of a biocompatible implantable device. As a non-limiting example, porous material is applied only to the front surface of a biocompatible implantable device or only the back surface of a biocompatible implantable device.

Thus, in an embodiment, a porous material is attached to a surface of a biocompatible implantable device by bonding a porous material to a surface of a biocompatible implantable device. In aspects of this embodiment, a porous material is attached to a surface of a biocompatible implantable device by gluing, bonding, or melting the porous material to a surface of a biocompatible implantable device.

In another embodiment, a porous material is attached to a surface of a biocompatible implantable device by forming the porous material onto a surface of a biocompatible implantable device. In aspects of this embodiment, a porous material is attached to a surface of a biocompatible implantable device by cast coating, spray coating, dip coating, curtain coating, knife coating, brush coating, or vapor deposition coating.

In another aspect of this embodiment, forming a porous material on a surface of a biocompatible implantable device comprises coating a cured elastomer base layer with an elastomer base and then coating the uncured elastomer base with porogens to form an elastomer coated porogen mixture. In other aspects of this embodiment, coating a cured elastomer base layer with an uncured elastomer base and then coating the uncured elastomer base with porogens to form an elastomer coated porogen mixture can be repeated, e.g., at least once, at least twice, at least three times, at least four times, at least five times, at least six times, at least seven times, at least eight times, at least nine times, or at least ten times, before the mixture is treated.

In another embodiment, a porous material is applied to the entire surface of a biocompatible implantable device. In another embodiment, a porous material is applied to a portion of a surface of a biocompatible implantable device. In aspects of this embodiment, a porous material is applied to a front surface of a biocompatible implantable device or a back surface of a biocompatible implantable device. In other aspects, a porous material is applied only to, e.g., about 20%, about 30%, about 40%, about 50%, about 60%, about 70% about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70% at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70% at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material applied to a biocompatible implantable device can be of any thickness with the proviso that the material thickness allows tissue growth within the array of interconnected of pores of an elastomer matrix in a manner sufficient to reduce or prevent formation of fibrous capsules that can result in capsular contracture or scarring.

Thus, in an embodiment, a layer of porous material applied to a biocompatible implantable device is of a thickness that allows tissue growth within the array of interconnected of pores of an elastomer matrix in a manner sufficient to reduce or prevent formation of fibrous capsules that can result in capsular contracture or scarring. In aspects of this embodiment, a layer porous material applied to a biocompatible implantable device comprises a thickness of, e.g., about 100 μm, about 200 μm, about 300 μm, about 400 μm, about 500 μm, about 600 μm, about 700 μm, about 800 μm, about 900 μm, about 1 mm, about 2 mm, about 3 mm, about 4 mm, about 5 mm, about 6 mm, about 7 mm, about 8 mm, about 9 mm, or about 10 mm. In other aspects of this embodiment, a layer porous material applied to a biocompatible implantable device comprises a thickness of, e.g., at least 100 μm, at least 200 μm, at least 300 μm, at least 400 μm, at least 500 μm, at least 600 μm, at least 700 μm, at least 800 μm, at least 900 μm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer porous material applied to a biocompatible implantable device comprises a thickness of, e.g., at most 100 μm, at most 200 μm, at most 300 μm, at most 400 μm, at most 500 μm, at most 600 μm, at most 700 μm, at most 800 μm, at most 900 μm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer porous material applied to a biocompatible implantable device comprises a thickness of, e.g., about 100 μm to about 500 μm, about 100 μm to about 1 mm, about 100 μm to about 5 mm, about 300 μm to about 1 mm, about 300 μm to about 2 mm, about 300 μm to about 3 mm, about 300 μm to about 4 mm, about 300 μm to about 5 mm, about 500 μm to about 1 mm, about 500 μm to about 2 mm, about 500 μm to about 3 mm, about 500 μm to about 4 mm, about 500 μm to about 5 mm, about 800 μm to about 1 mm, about 800 μm to about 2 mm, about 800 μm to about 3 mm, about 800 μm to about 4 mm, about 800 μm to about 5 mm, about 1 mm to about 2 mm, about 1 mm to about 3 mm, about 1 mm to about 4 mm, about 1 mm to about 5 mm, or about 1.5 mm to about 3.5 mm.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 75 μm or less, has fiber disorganization comprising 50% or more of the fibers that are not parallel to the prosthesis surface, has tissue growth into the biomaterial of the prosthesis of 100 μm or more, has less than 40% collagen content, adheres to tissue with a peak force of at least 8 N and/or and has a stiffness of 20 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 50 μm or less, has fiber disorganization comprising 60% or more of the fibers that are parallel to the prosthesis surface, has tissue growth into the biomaterial of the prosthesis of 125 μm or more, has less than 30% collagen content, adheres to tissue with a peak force of at least 9 N and/or and has a stiffness of 15 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 25 μm or less, has fiber disorganization comprising 70% or more of the fibers that are not parallel to the prosthesis surface, has tissue growth into the biomaterial of the prosthesis of 150 μm or more, has less than 20% collagen content, adheres to tissue with a peak force of at least 10 N and/or and has a stiffness of 10 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of about 5 μm to about 75 μm, has fiber disorganization comprising about 50% to about 90% of the fibers that are not parallel to the prosthesis surface, has tissue growth into the biomaterial of the prosthesis of about 100 μm to about 300 μm, has about 5% to about 40% collagen content, adheres to tissue with a peak force of about 8 N to about 11 N, and/or and has a stiffness of about 5 mmHg/mL to about 20 mmHg/mL.

EXAMPLES

The following examples illustrate representative embodiments now contemplated, but should not be construed to limit the disclosed porous materials, methods of forming such porous materials, biocompatible implantable devices comprising such porous materials, and methods of making such biocompatible implantable devices.

Example 1

A Method of Making a Porous Material Sheet

This example illustrates how to make a sheet of porous material disclosed herein.

To coat porogens with an elastomer base, an appropriate amount of PLGA (50/50) porogens (500 μm diameter) is mixed with an appropriate amount of 35% (w/w) silicon in xylene (MED 6400; NuSil Technology LLC, Carpinteria, Calif.). The mixture is filtered through a 43 μm sieve to remove the excess silicone and is poured into about 20 cm×20 cm square mold coated with a non-stick surface.

To treat an elastomer coated porogen mixture to allow fusing of the porogens to form a porogen scaffold and curing of the non-degradable biocompatible elastomer, the PLGA/silicone mixture is placed into an oven and is heated at a temperature of 75° C. for 45 min, and then 126° C. for 75 minutes. After curing, the sheet of cured elastomer coated porogen scaffold is removed.

To remove a porogen scaffold from the cured elastomer, the cured elastomer/porogen scaffold is immersed in methylene chloride. After 30 minutes, the methylene chloride is removed and fresh methylene chloride is added. After 30 minutes, the methylene chloride is removed and the resulting 30 cm×30 cm×1.5 mm sheet of porous material is air dried at ambient temperature. This process results in a porous material sheet as disclosed herein.

A sample from the sheet of porous material can be characterized by microCT analysis and/or scanning electron microscopy (SEM).

Example 2

A Method of Making a Biocompatible Implantable Device Comprising a Porous Material This example illustrates how to make a biocompatible implantable device comprising a porous material disclosed herein.

Sheets of porous material comprising an elastomer matrix defining an interconnected array of pores is obtained as described in Example 1.

Figure 2A:
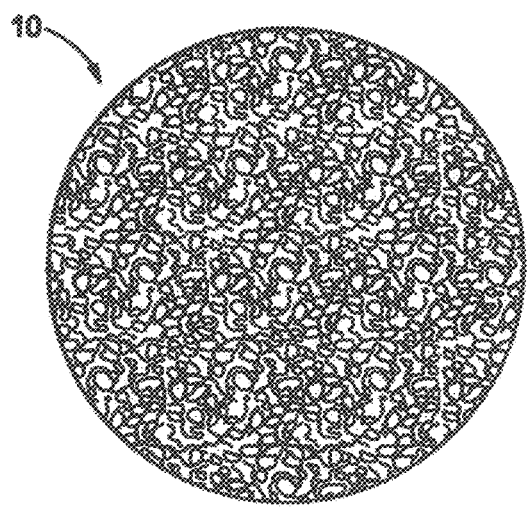
FIGS. 2A-2D illustrate a representative biocompatible implantable device covered with a porous material of the present specification.
Figure 2B:
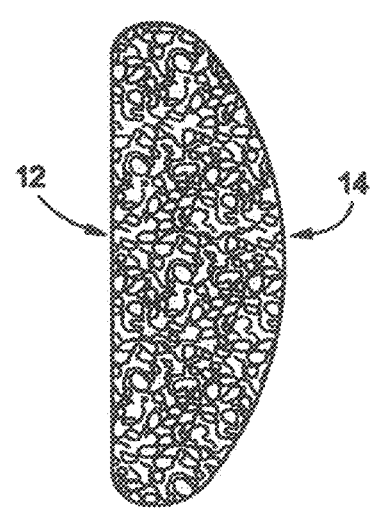
Figure 2C:
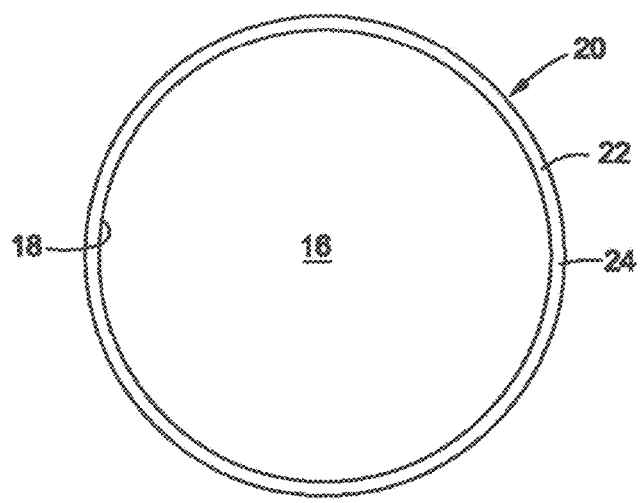
Figure 2D:
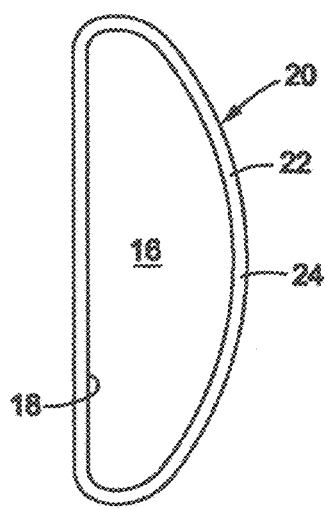

To attach a porous material to a biocompatible implantable device, a first porous material sheet is coated with a thin layer of silicone and then placed in the bottom cavity of a mold, adhesive side up. A biocompatible implantable device is then placed on top of the material surface coated with the adhesive. A second porous material sheet is then coated with a thin layer of silicone and applied to the uncovered surface of the biocompatible implantable device. The top piece of the mold cavity is then fixed in place pressing the two material sheets together creating a uniform interface. The silicone adhesive is allowed to cure by placing the covered device into an oven and heated at a temperature of 126° C. for 75 minutes. After curing, excess material is trimmed off creating a uniform seam around the biocompatible implantable device. This process results in a biocompatible implantable device 10 as disclosed herein (FIG. 2). FIG. 2A is a top view of an implantable device covered with a porous material 10. FIG. 2B is a side view of an implantable device covered with a porous material 10 to show a bottom 12 of the implantable device 10 and a top 14 of the implantable device 10. FIGS. 2C and 2D illustrate the cross-sectional view of the biocompatible implantable device covered with a porous material 10 to show an implantable device 16, a porous material layer 20 including an internal surface 22 and an external surface 24, where the internal surface 22 is attached to an implantable device surface 18. Due to the presence of the porous material on the device surface of the biocompatible implantable device there will be a reduction or prevention of the formation of fibrous capsules that can result in capsular contracture or scarring.

Alternatively, the porous material can be laminated onto a biocompatible implantable device while the device is still on a mandrel. In this process, a first porous material sheet is coated with a thin layer of silicone and then draped over the device on the mandrel in such a way that there are no wrinkles on the surface. After curing the silicone adhesive, as as described above, another coating of silicone is applied to the uncovered surface of the biocompatible implantable device and a second porous material is stretched up to cover the back of the device. After curing the silicone adhesive, as described above, the biocompatible implantable device is then taken off the mandrel and the excess porous material is trimmed to create a uniform seam around the device. This process results in a biocompatible implantable device comprising a porous material as disclosed herein. See, e.g., FIG. 2.

Example 3

A Method of Making a Porous Material Shell

This example illustrates how to make a porous material shell disclosed herein.

To coat porogens with a non-degradable biocompatible elastomer, an appropriate amount of PLGA (50/50) porogens (500 μm diameter) is mixed with an appropriate amount of 35% (w/w) silicon in xylene (MED 6400; NuSil Technology LLC, Carpinteria, Calif.). The mixture is filtered through a 43 μm sieve to remove the excess silicone.

The filtered elastomer coated porogen mixture is poured into a mold in the shape of a breast implant shell and the mold is mechanically agitated to pack firmly the mixture. The thickness of the shell is controlled based upon the design of the shell mold.

To treat an elastomer coated porogen mixture to allow fusing of the porogens to form a porogen scaffold and curing of the non-degradable biocompatible elastomer, the PLGA/silicone mixture is placed into an oven and is heated at a temperature of 75° C. for 45 min, and then 126° C. for 75 minutes. After curing, the shell mold is dismantled and the cured elastomer coated porogen scaffold is removed.

Figure 3A:
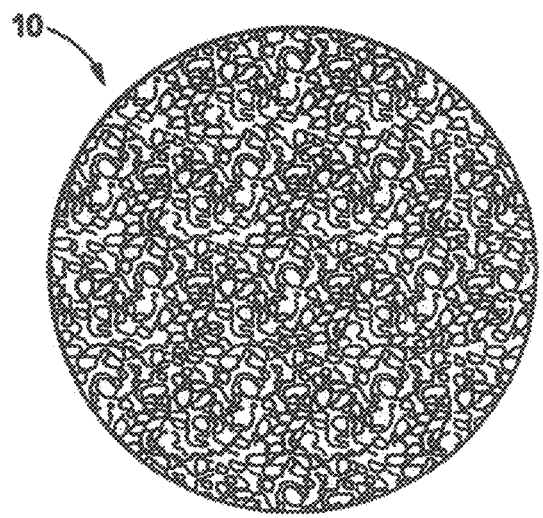
FIGS. 3A-3D illustrate a representative porous material shell of the present specification.
Figure 3B:
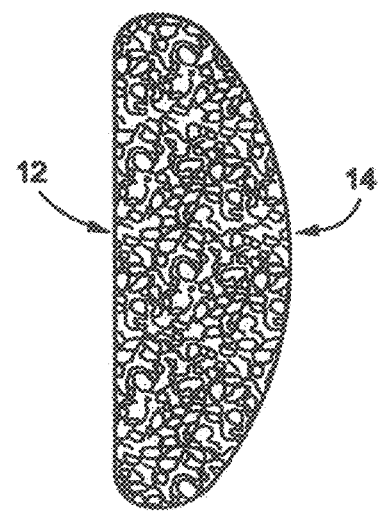
Figure 3C:
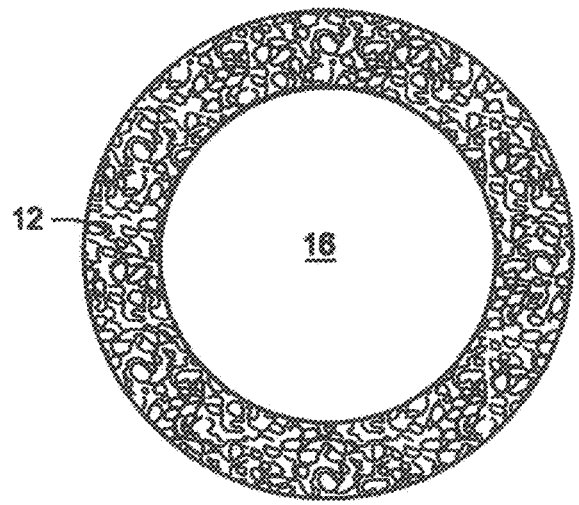
Figure 3D:
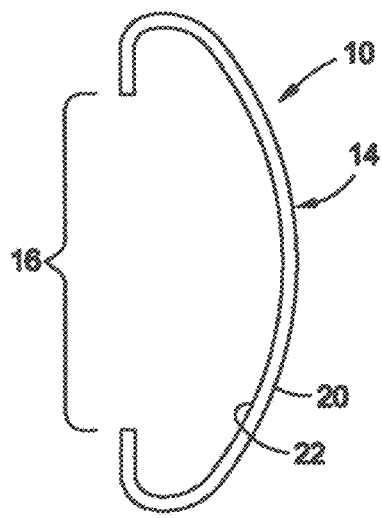

To remove a porogen scaffold from the cured elastomer, the cured elastomer/porogen scaffold is immersed in methylene chloride. After 30 minutes, the methylene chloride is removed and fresh methylene chloride is added. After 30 minutes, the methylene chloride is removed and the resulting 30 cm×30 cm×1.5 mm sheet of porous material is air dried at an ambient temperature of about 18° C. to about 22° C. This process results in a porous material shell 10 as disclosed herein (FIG. 3). FIG. 3A is a top view of a material shell 10. FIG. 2B is a side view of a material shell 10 to show a bottom 12 of the material shell 10 and a top 14 of the material shell 10. FIG. 3C is a bottom view of a material shell 10 to show a hole 16 from which a biocompatible implantable device may be subsequently inserted through. FIG. 3D illustrate the cross-sectional view of the material shell 10 to show the hole 16, an internal surface 20 of the material shell 10 and an external surface 22 of the material shell 10.

A sample from the sheet of porous material can be characterized by microCT analysis and/or scanning electron microscopy (SEM).

Example 4

A Method of Making a Biocompatible Implantable Device Comprising a Porous Material This example illustrates how to make a biocompatible implantable device comprising a porous material disclosed herein.

A porous material shell comprising an elastomer matrix defining an interconnected array of pores is obtained as described in Example 3.

Figure 4A:
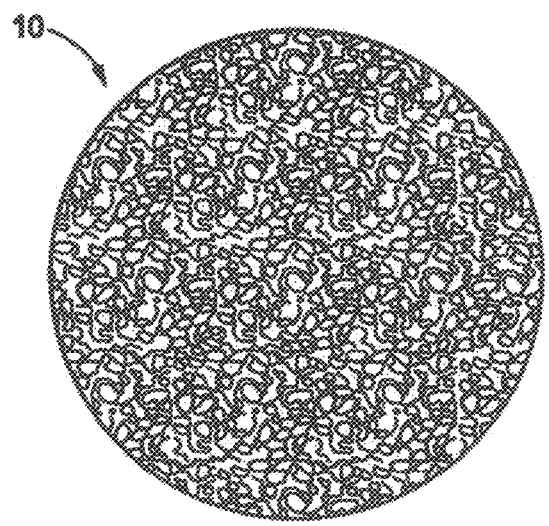
FIGS. 4A-4D illustrate a representative biocompatible implantable device covered with a porous material of the present specification.
Figure 4B:
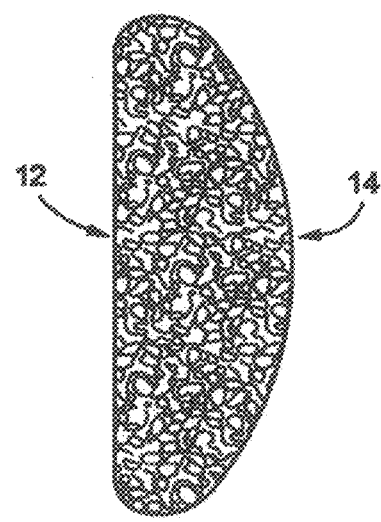
Figure 4C:
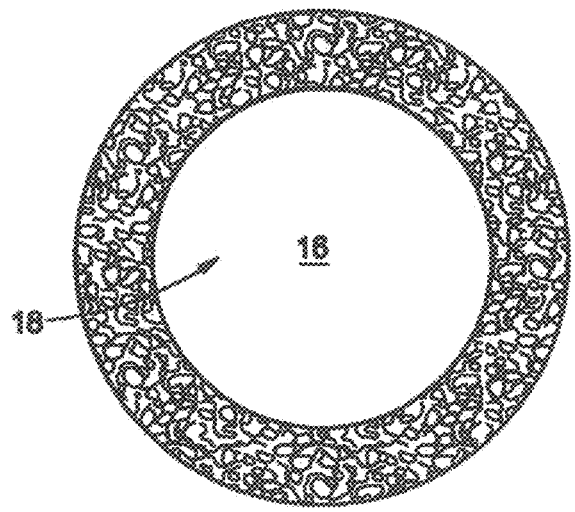
Figure 4D:
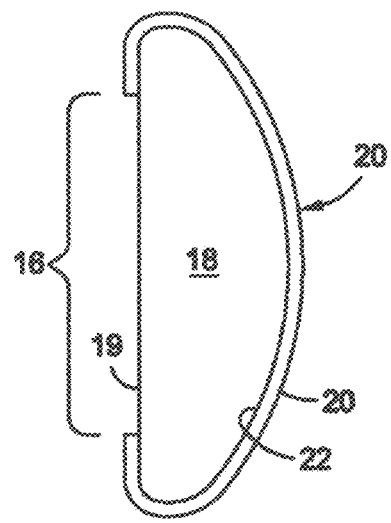

To attach the porous material shell to a biocompatible implantable device, the surface of the device is coated with a thin layer of silicone. The material shell is then placed over the adhesive coated device in a manner that ensures no wrinkles in the material form. The silicone adhesive is allowed to cure by placing the covered device into an oven and heating at a temperature of 126° C. for 75 minutes. After curing, excess material is trimmed off creating a uniform seam around the biocompatible implantable device. This process results in a biocompatible implantable device comprising a porous material 10 as disclosed herein (FIG. 4). FIG. 4A is a top view of an implantable device covered with a porous material 10. FIG. 4B is a side view of an implantable device covered with a porous material 10 to show a bottom 12 of the implantable device 10 and a top 14 of the implantable device 10. FIG. 4C is a bottom view of a biocompatible implantable device covered with a porous material 10 to show a hole 16 and an implantable device 18. FIG. 4D illustrates the cross-sectional view of the biocompatible implantable device covered with a porous material 10 to show an implantable device 18, a porous material layer 20 including an internal surface 22 and an external surface 24, where the internal surface 22 is attached to implantable device surface 19. Due to the presence of the porous material on the device surface of the biocompatible implantable device there will be a reduction or prevention of the formation of fibrous capsules that can result in capsular contracture or scarring.

Example 5

A Method of Making an Implant Comprising a Porous Material

This example illustrates how to make an implant comprising a porous material disclosed herein of about 0.5 mm to about 1.5 mm in thickness.

To prepare the surface of a device to receive a porous material, a base layer of 35% (w/w) silicon in xylene (MED4810; NuSil Technology LLC, Carpinteria, Calif.) was coated on a mandrel (LR-10), placed into an oven, and cured at a temperature of 126° C. for 75 minutes. Alternatively, a previously made biocompatible implantable device, such as, e.g., a base shell disclosed herein, can be attached to a mandrel and then processed beginning with the next step.

To coat the base layer with a mixture comprising a non-degradable biocompatible elastomer and porogens, the cured base layer was dipped first in 35% (w/w) silicon in xylene (MED4810; NuSil Technology LLC, Carpinteria, Calif.) and then air dried for about 3 minutes to allow the xylene to evaporate. After xylene evaporation, the Mandrel with the uncured silicone was dipped in PLGA porogens until the maximum amount of porogens were absorbed into the uncured silicone. The mandrel with the uncured silicon/PGLA PLGA coating was air dried for about 60 minutes to allow the xylene to evaporate.

To treat an elastomer coated porogen mixture to allow fusing of the porogens to form a porogen scaffold and curing of the non-degradable biocompatible elastomer, the Mandrel coated with the uncured silicone/PLGA mixture was placed into an oven and cured at a temperature of 75° C. for 30 min, and then 126° C. for 75 minutes.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 0.5 mm to about 1.5 mm was air dried at an ambient temperature of about 18° C. to about 22° C. This process results in a biocompatible implantable device comprising a porous material as disclosed herein. See, e.g., FIG. 2 and FIG. 4.

A sample from the implant was characterized by SEM. This analysis revealed that the porous material was about 1.4 mm to about 1.6 mm in thickness.

To increase the thickness of the porous material covering the base layer, multiple dippings were performed to produce a mandrel coated with multiple layers of an uncured silicone/porogen mixture. Dippings were repeated until the desired thickness is achieved. Examples 6-8 below describe specific examples of this multiple dipping technique.

Example 6

A Method of Making an Implant Comprising a Porous Material

This example illustrates how to make an implant comprising a porous material disclosed herein of about 1 mm to about 2.5 mm in thickness.

A mandrel comprising a base layer of elastomer was prepared as described in Example 3 or a previously made biocompatible implantable device, such as, e.g., a base shell disclosed herein, can be attached to the mandrel as described in Example 3 and then processed beginning with the next step.

To coat the base layer with a mixture comprising a non-degradable biocompatible elastomer and porogens, the cured base layer was dipped first in 35% (w/w) silicon in xylene (MED4810; NuSil Technology LLC, Carpinteria, Calif.) and then air dried for about 3 minutes to allow the xylene to evaporate. After xylene evaporation, the mandrel with the uncured silicone was dipped in PLGA porogens until the maximum amount of porogens were absorbed into the uncured silicone. The mandrel with the uncured silicon/PLGA coating was air dried for about 60 minutes to allow the xylene to evaporate. After xylene evaporation, the mandrel coated with the uncured silicone/PLGA porogen mixture was dipped first in 35% (w/w) silicon in xylene, air dried to allow xylene evaporation (about 3 minutes), and then dipped in PLGA porogens until the maximum amount of porogens were absorbed into the uncured silicone. The mandrel with the second coating of uncured silicon/PLGA porogen mixture was air dried for about 60 minutes to allow the xylene to evaporate.

The mandrel comprising the two coats of uncured silicone/PLGA porogen mixture was treated as described in Example 3.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 1 mm to about 2.5 mm was air dried at an ambient temperature of about 18° C. to about 22° C. This process results in a biocompatible implantable device comprising a porous material as disclosed herein. See, e.g., FIG. 2 and FIG. 4.

A sample from the implant was characterized by SEM and microCT analysis. This analysis revealed that the porous material was about 2 mm to about 2.5 mm in thickness with a porosity of about 88%.

Porous materials of a similar characteristic were also produced using PCL porogens instead of PLGA porogens.

Example 7

A Method of Making an Implant Comprising a Porous Material

This example illustrates how to make an implant comprising a porous material disclosed herein of about 2.5 mm to about 4.5 mm in thickness.

A mandrel comprising a base layer of elastomer was prepared as described in Example 3 or a previously made biocompatible implantable device, such as, e.g., a base shell disclosed herein, can be attached to the mandrel as described in Example 3 and then processed beginning with the next step.

To coat the base layer with a mixture comprising a non-degradable biocompatible elastomer and porogens, the cured base layer was dipped first in 35% (w/w) silicon in xylene (MED4810; NuSil Technology LLC, Carpinteria, Calif.) and then air dried for about 3 minutes to allow the xylene to evaporate. After xylene evaporation, the mandrel with the uncured silicone was dipped in PLGA porogens until the maximum amount of porogens were absorbed into the uncured silicone. The mandrel with the uncured silicon/PLGA coating was air dried for about 60 minutes to allow the xylene to evaporate. After xylene evaporation, the mandrel coated with the uncured silicone/PLGA porogen mixture was dipped first in 35% (w/w) silicon in xylene, air dried to allow xylene evaporation (about 3 minutes), and then dipped in PLGA porogens until the maximum amount of porogens were absorbed into the uncured silicone. The mandrel with the second coating of uncured silicon/PLGA was air dried for about 60 minutes to allow the xylene to evaporate. After xylene evaporation, the mandrel coated with the two layers of the uncured silicone/PLGA porogen mixture was dipped first in 32% (w/w) silicon in xylene, air dried to allow xylene evaporation (about 3 minutes), and then dipped in PLGA porogens until the maximum amount of porogens were absorbed into the uncured silicone. The mandrel with the third coating of uncured silicon/PLGA porogen mixture was air dried for about 60 minutes to allow the xylene to evaporate.

The mandrel comprising the two coats of uncured silicone/PLGA porogens was treated as described in Example 3.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 2.5 mm to about 4.5 mm was air dried at an ambient temperature of about 18° C. to about 22° C. This process results in a biocompatible implantable device comprising a porous material as disclosed herein. See, e.g., FIG. 2 and FIG. 4.

A sample from the implant was characterized by SEM and microCT analysis. This analysis revealed that the porous material was about 3.5 mm to about 4.5 mm in thickness.

Example 8

A Method of Making an Implant Comprising a Porous Material

This example illustrates how to make an implant comprising a porous material disclosed herein of about 3.5 mm to about 5.5 mm in thickness.

A mandrel comprising a base layer of elastomer was prepared as described in Example 3 or a previously made biocompatible implantable device, such as, e.g., a base shell disclosed herein, can be attached to the mandrel as described in Example 3 and then processed beginning with the next step.

To coat the base layer with a mixture comprising a non-degradable biocompatible elastomer and porogens, the cured base layer was dipped first in 35% (w/w) silicon in xylene (MED4810; NuSil Technology LLC, Carpinteria, Calif.) and then air dried for about 3 minutes to allow the xylene to evaporate. After xylene evaporation, the Mandrel with the uncured silicone was dipped in PLGA porogens until the maximum amount of porogens were absorbed into the uncured silicone. The mandrel with the uncured silicon/PLGA coating was air dried for about 60 minutes to allow the xylene to evaporate. After xylene evaporation, the mandrel coated with the uncured silicone/PLGA porogen mixture was dipped first in 35% (w/w) silicon in xylene, air dried to allow xylene evaporation (about 3 minutes), and then dipped in PLGA porogens until the maximum amount of porogens were absorbed into the uncured silicone. The mandrel with the second coating of uncured silicon/PLGA was air dried for about 60 minutes to allow the xylene to evaporate. After xylene evaporation, the mandrel coated with the two layers of the uncured silicone/PLGA porogen mixture was dipped first in 32% (w/w) silicon in xylene, air dried to allow xylene evaporation (about 3 minutes), and then dipped in PLGA porogens until the maximum amount of porogens were absorbed into the uncured silicone. The mandrel with the third coating of uncured silicon/PLGA porogen mixture was air dried for about 60 minutes to allow the xylene to evaporate. After xylene evaporation, the mandrel coated with the three layers of the uncured silicone/PLGA porogen mixture was dipped first in 28% (w/w) silicon in xylene, air dried to allow xylene evaporation (about 3 minutes), and then dipped in PLGA porogens until the maximum amount of porogens were absorbed into the uncured silicone. The mandrel with the fourth coating of uncured silicon/PLGA porogen mixture was air dried for about 60 minutes to allow the xylene to evaporate.

The mandrel comprising the two coats of uncured silicone/PLGA porogens was treating as described in Example 3.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 3.5 mm to about 5.5 mm was air dried at an ambient temperature of about 18° C. to about 22° C. This process results in a biocompatible implantable device comprising a porous material as disclosed herein. See, e.g., FIG. 2 and FIG. 4.

A sample from the implant was characterized by microCT analysis. This analysis revealed that the porous material was about 4.5 mm to about 5.5 mm in thickness.

Example 9

A Method of Making an Implant Comprising a Porous Material

This example illustrates how to make a biocompatible implantable device (an implant) comprising a porous material layer as disclosed herein, wherein the porous material layer is about 2.5 mm to about 4.5 mm in thickness. Except as otherwise indicated, all steps in this Example were conducted at 25° C.

An elastomer coated porogen mixture was created, the elastomer in this Example being silicone. To prepare a surface to act as the base for the elastomer coated porogen mixture, a base layer of 35% (w/w) silicone in xylene (PN-3206-1; NuSil Technology LLC, Carpinteria, Calif.) was coated on a mandrel (LR-10), placed into an oven, and cured at a temperature of 126° C. for 75 minutes. Alternatively, a previously made biocompatible implantable device, such as, e.g., a base shell disclosed herein, can be attached to a mandrel and then processed beginning with the next step.

The cured base layer was then dipped in about 35% (w/w) silicone in xylene (PN-3206-1; NuSil Technology LLC, Carpinteria, Calif.) and air dried for about 18 minutes to about 22 minutes to allow the xylene to evaporate (devolatilization), thus creating a tacky pore coat.

The mandrel with the base layer covered by the tacky pore coat was then dipped in a composition of PLGA (50/50) porogens (550 µm mean diameter) until the maximum amount of porogens were absorbed into the uncured silicone, to create a texture bead coat. The texture bead coat (uncured silicone/porogen coating) was then air dried for about 4.5 minutes to about 5.5 minutes to allow for continued devolatilization.

The texture bead coat was then dipped again in silicone as described above to add additional pore coat, and permitted to devolatilize for about 4 minutes to about 5 minutes. The pore coat was then dipped again in porogens as described above to create another layer of texture bead coat, and permitted to devolatilize for about 25 minutes to about 35 minutes. The texture bead coat was then dipped a third time in silicone as described above to create another layer of pore coat, and permitted to devolatilize for about 4 minutes to about 5 minutes. Then the pore coat was dipped in porogens a final time as described above, and permitted to devolatilize for at least 45 minutes. The process resulted in an elastomer coated porogen mixture having three layers of texture bead (porogen) coat.

To treat the elastomer coated porogen mixture to allow fusing of the porogens to form a porogen scaffold and to stabilize the elastomer, the elastomer coated porogen mixture was placed into an oven at a temperature of about 126° C. for about 85 minutes. After curing, the shell mold is dismantled and the cured elastomer coated porogen scaffold is removed.

To remove the porogen scaffold, the cured silicone/porogen scaffold was then subjected to more than one repetition of soaking in hot water followed by rinsing in water until all scaffold was dissolved and removed from the elastomer. In this Example, the elastomer coated porogen mixture was immersed in hot water (about 60° C.) for about 8 minutes to about 10 minutes, followed by rinsing in water (less than 45° C.). The mixture was then immersed again in hot water (about 60° C.) for about 20 minutes to about 30 minutes, and rinsed again. Finally the elastomer was immersed one more time in hot water (about 60° C.) for about 20 minutes to about 30 minutes, followed by rinsing in water while massaging (squeezing) the submerged substance about 10 to about 15 times to remove the now dissolved porogen scaffold material.

This process resulted in a biocompatible implantable device comprising an outer porous material layer (or shell) comprising a layer of interconnected pores, as disclosed herein. See, e.g., FIGS. 2 and 4. Because the diameter of the porogens was about 550 µm, the average pore size of the porous material was likewise about 550 µm. A sample from the porous material was characterized by microCT analysis. This analysis revealed that the porous material was about 0.8 mm to about 3.0 mm in thickness, with a porosity of about 85% or more, with a surface openness (pore area/total area) of about 60-75%. The porous material has an elongation at break of 450%. Scanning electron microscopy (SEM) analysis of the porous material is shown in FIG. 1.

As an alternative example of creating a biocompatible implantable device comprising a porous material layer, the porous material layer is created separately and then attached to the device. In such example, a first porous material layer is created as described above, and is coated with a thin layer of adhesive, for example silicone, and then placed in the bottom cavity of a mold, adhesive side up. A biocompatible implantable device is then placed on top of the porous material surface coated with the adhesive. A second porous material layer is then coated with a thin layer of adhesive such as silicone and applied to the uncovered surface of the biocompatible implantable device. The top piece of the mold cavity is then fixed in place, pressing the two porous material sheets together to create a uniform interface. The silicone adhesive is allowed to cure by placing the covered device into an oven and heated at a temperature of 126° C. for 75 minutes. After curing, excess material is trimmed off creating a uniform seam around the biocompatible implantable device. This process results in a biocompatible implantable device comprising a porous material as disclosed herein.

Alternatively, the porous material created as described above can be laminated onto a biocompatible implantable device while the device is still on a mandrel. In this process, a first porous material layer is coated with a thin layer of silicone and then draped over the device on the mandrel in such a way that there are no wrinkles on the surface. After curing the silicone adhesive, as described above, another coating of silicone is applied to the uncovered surface of the biocompatible implantable device and a second porous material layer is stretched up to cover the back of the device. After curing the silicone adhesive, as described above, the biocompatible implantable device is then taken off the mandrel and the excess porous material is trimmed to create a uniform seam around the device. This process results in a biocompatible implantable device comprising a porous material as disclosed herein. See, e.g., FIGS. 2 and 4.

Example 10

Capsule Thickness and Disorganization

In order to measure the thickness and disorganization of capsules formed, disks (1 cm in diameter) of various porous biomaterials were implanted subcutaneously in Sprague-Dawley rats using standard procedures. The biomaterials tested were taken from commercially available implants or experimentally produced as follows: Smooth 1, a biomaterial having a smooth surface (NATRELLE®, Allergan, Inc., Irvine, Calif.); Smooth 2, a biomaterial having a smooth surface (MEMORYGEL®, Mentor, Inc., Santa Barbara, Calif.); Textured 1, a biomaterial having a closed-cell textured surface produced from a lost-salt method (BIOCELL®, Allergan, Inc., Irvine, Calif.); Textured 2, a biomaterial having a closed-cell textured surface produced from an imprinting method (SILTEX®, Mentor, Inc., Santa Barbara, Calif.); Textured 3, a biomaterial having a closed-cell textured surface produced from either an imprinting or gas foam method (SILIMED®, Sientra, Inc., Santa Barbara, Calif.); Textured 4, a biomaterial having a closed-cell textured surface produced from an imprinting method (Perouse Plastie, Mentor, Inc., Santa Barbara, Calif.); Textured 5, a biomaterial having an open-cell polyurethane surface; Textured 6, a biomaterial having an open-cell textured surface produced according to the methods disclosed herein. Samples were harvested at 6 weeks, fixed in formalin, and processed to produce paraffin blocks. The paraffin blocks were sectioned using a microtome at 2 µm thickness and stained with hematoxylin and eosin (H&E).

Capsules were characterized by measuring the thickness and disorganization of the capsule formed over the porous biomaterial. Capsule thickness was measured by acquiring 2 representative 20× images of the H&E stained biomaterials and measuring the thickness of the capsule at 3 points in the image. Capsule disorganization was evaluated by acquiring 3 representative 20× images of the H&E stained biomaterials, and then drawing a reference vector tangent to the implant surface, as well as, drawing vectors along collagen fibers within the capsule. The angle of each vector relative to the reference vector was then measured, and the standard deviation of the angles was calculated, where greater standard deviations reflected a higher degree of disorganization. All image analysis calculations were performed on the Nikon Elements Advanced Research software.

All thickness and disorganization measurements were acquired blinded and each measurement was normalized to the data obtained from Textured 1 biomaterial. For the thickness data collected, a one-way ANOVA was run to determine significant effects ($p<0.05$). If there were any statistically significant effects from the ANOVA analysis, the Tukey's post-hoc test was run for multiple comparisons at $\alpha=0.05$. For the disorganization data collected, a Levene's Test for Equal Variance was used to determine whether there was a statistically significant difference in disorganization between experimental groups ($p<0.05$). Between individual groups, the criteria for non-significance were overlap of confidence intervals (95%), adjusted for the number of groups.

Figure 5A:
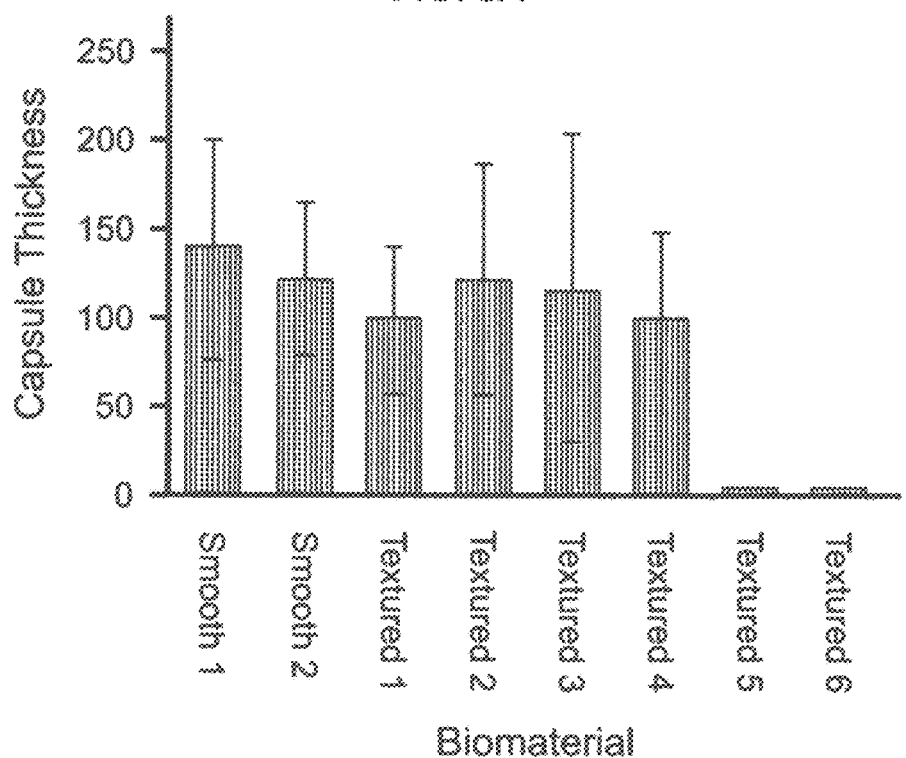
FIGS. 5A and 5B are bar graphs showing data of thickness and disorganization of capsules from various biomaterials, normalized to Textured 1 biomaterial.
Figure 5B:
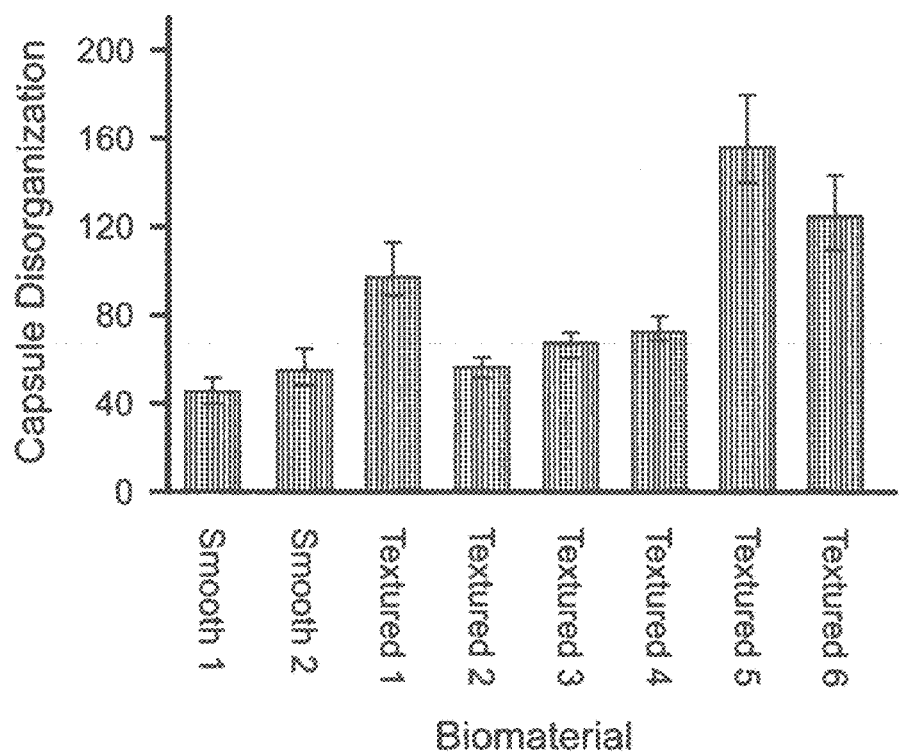

The capsule thicknesses and disorganization, normalized to the Texture 1 biomaterial within each respective study, are shown in FIG. 5. Smooth Texture 1 and 2 biomaterials, and Textures 1-4 biomaterials (having closed-cell texture) exhibited pronounced capsule formation, and the capsules formed were of equivalent thicknesses of about 100 µm to about 140 µm (FIG. 5A). Texture 5-6 biomaterials exhibited minimal capsule formation with capsules formed having a thickness of less than 10 µm (FIG. 5A). With respect to capsule organization, it was found that Texture 1 biomaterial resulted in a capsule that was more disorganized than Smooth 1 and 2 and Texture 2-4 biomaterials (FIG. 5B). Texture 5 and 6 biomaterials demonstrated extensive ingrowth (about 200 µm) that was interconnected and significantly more disorganized 50% of fibers were not parallel to implant surface) than Smooth 1 and 2 and Texture 1-4 biomaterials (FIG. 5B). These findings show that Smooth 1 and 2 biomaterials (smooth surface) and Textures 1-4 biomaterials (closed-cell textured surfaces) resulted in a capsule with predominantly organized collagen. Textures 5-6 biomaterials (open-cell textured surfaces), in contrast, induce significant ingrowth that can eliminate capsule and disorganize the tissue at the material-tissue interface.

Example 11

Capsule Collagen

In order to measure the collagen content of capsules formed, disks (1 cm in diameter) of various porous biomaterials were implanted subcutaneously in Sprague-Dawley rats using standard procedures. The biomaterials tested were taken from commercially available implants or experimentally produced as follows: Smooth 1, a biomaterial having a smooth surface (NATRELLE®, Allergan, Inc., Irvine, Calif.); Smooth 2, a biomaterial having a smooth surface (MEMORYGEL®, Mentor, Inc., Santa Barbara, Calif.); Textured 1, a biomaterial having a closed-cell textured surface produced from a lost-salt method (BIOCELL®, Allergan, Inc., Irvine, Calif.); Textured 2, a biomaterial having a closed-cell textured surface produced from an imprinting method (SILTEX®, Mentor, Inc., Santa Barbara, Calif.); Textured 3, a biomaterial having a closed-cell textured surface produced from an imprinting method (Perouse Plastie, Mentor, Inc., Santa Barbara, Calif.); Textured 4, a biomaterial having a closed-cell textured surface produced from either an imprinting or gas foam method (SILIMED®, Sientra, Inc., Santa Barbara, Calif.); Textured 5, a biomaterial having an inverse foam polyurethane-polyethylene glycol surface; Textured 6, a biomaterial having an inverse foam polyurethane-polyethylene glycol surface; Textured 7, a biomaterial having an open-cell polyurethane surface; Textured 8, a biomaterial having a non-woven felt surface. Samples were harvested at 6 weeks, fixed in formalin, and processed to produce paraffin blocks. The paraffin blocks were sectioned using a microtome at 2 µm thickness and stained with aniline blue.

Capsules were characterized by measuring staining darkness of the capsule formed over the implanted porous biomaterials. The darkness of the capsule was measured from 5 representative 20× images, with overall intensity averaged over the capsules to reflect the depth of staining. To account for variations in parameters, such as section thickness and precise staining times, all measurements were normalized to the intensity measured within the dermis of the same section, which was utilized as a standard due to the consistent staining that was observed in this region. A one-way ANOVA was run to determine significant effects ($p<0.05$). If there were any statistically significant effects from the ANOVA analysis, the Tukey's post-hoc test was run for multiple comparisons at $\alpha=0.05$.

Figure 6:
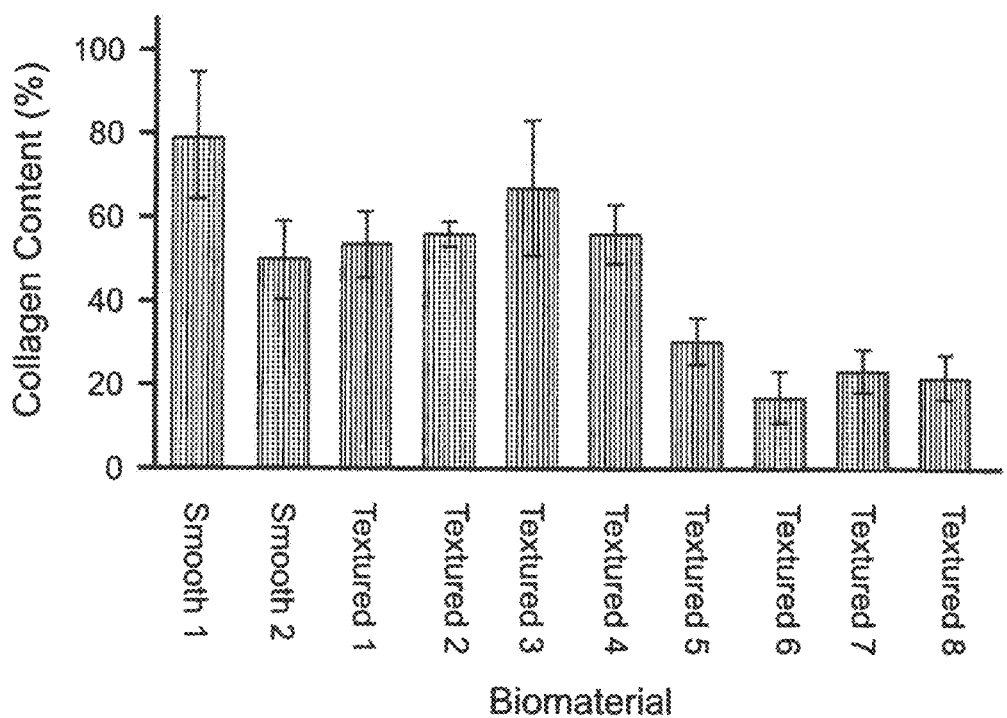
FIG. 6 is bar graph showing data of collagen content of capsules formed over various biomaterials (n=6). Results are shown as mean±standard deviation. Asterisks (*) indicates a statistically significant from Texture 1 biomaterial.

FIG. 6 shows the mean collagen density of capsules and ingrowth formed over smooth and textured porous biomaterials. It was found that the capsules formed over Smooth 1 and 2 biomaterials and Textured 1-4 biomaterials (closed-cell textured surfaces) showed a statistically significant increase in collagen density over the Texture 5 and 6 biomaterials (inverse foam textured surface), Textured 7 biomaterial (open-cell textured surface), and Textured 8 biomaterial (non-woven felt textured surface). As such, the prevention of capsule formation was shown to be linked to significant ingrowth into an open, interconnected texture, where the ingrowth has a low collagen density.

Example 12

Tissue Adhesion

In order to evaluate the effect of texture on tissue adhesion to a porous biomaterial, strips of various biomaterial were implanted subcutaneously in a Sprague-Dawley rat using standard procedures. The biomaterials tested were taken from commercially available implants or experimentally produced as follows: Smooth 1, n=38, a biomaterial having a smooth surface (NATRELLE®, Allergan, Inc., Irvine, Calif.); Textured 1, n=64, a biomaterial having a closed-cell textured surface produced from a lost-salt method (BIOCELL®, Allergan, Inc., Irvine, Calif.); Textured 2, n=6, a biomaterial having a closed-cell textured surface produced from an imprinting method (SILTEX®, Mentor, Inc., Santa Barbara, Calif.); Textured 3, n=6, a biomaterial having an inverse foam polyurethane-polyethylene glycol surface; Textured 4, n=45, a biomaterial having an inverse foam polyurethane-polyethylene glycol surface; Textured 5, n=45, a biomaterial having an open-cell polyurethane surface; Textured 6, n=6, a biomaterial having an open-cell polyurethane surface; Textured 7, n=6, a biomaterial having an open-cell textured surface of 0.8 mm produced according to the methods disclosed herein; Textured 8, n=6, a biomaterial having an open-cell textured surface of 1.5 mm produced according to the methods disclosed herein. Samples were harvested at 4 weeks, and tissue was pulled from the test strip on a mechanical tester with a pullout speed of 2 mm/second. Adhesion strength was measured as the peak force required to separate the implant from the surrounding tissue. A one-way ANOVA was run to determine significant effects ($p<0.05$). If there were any statistically significant effects from the ANOVA analysis, the Tukey's post-hoc test was run for multiple comparisons at $\alpha=0.05$.

Figure 7:
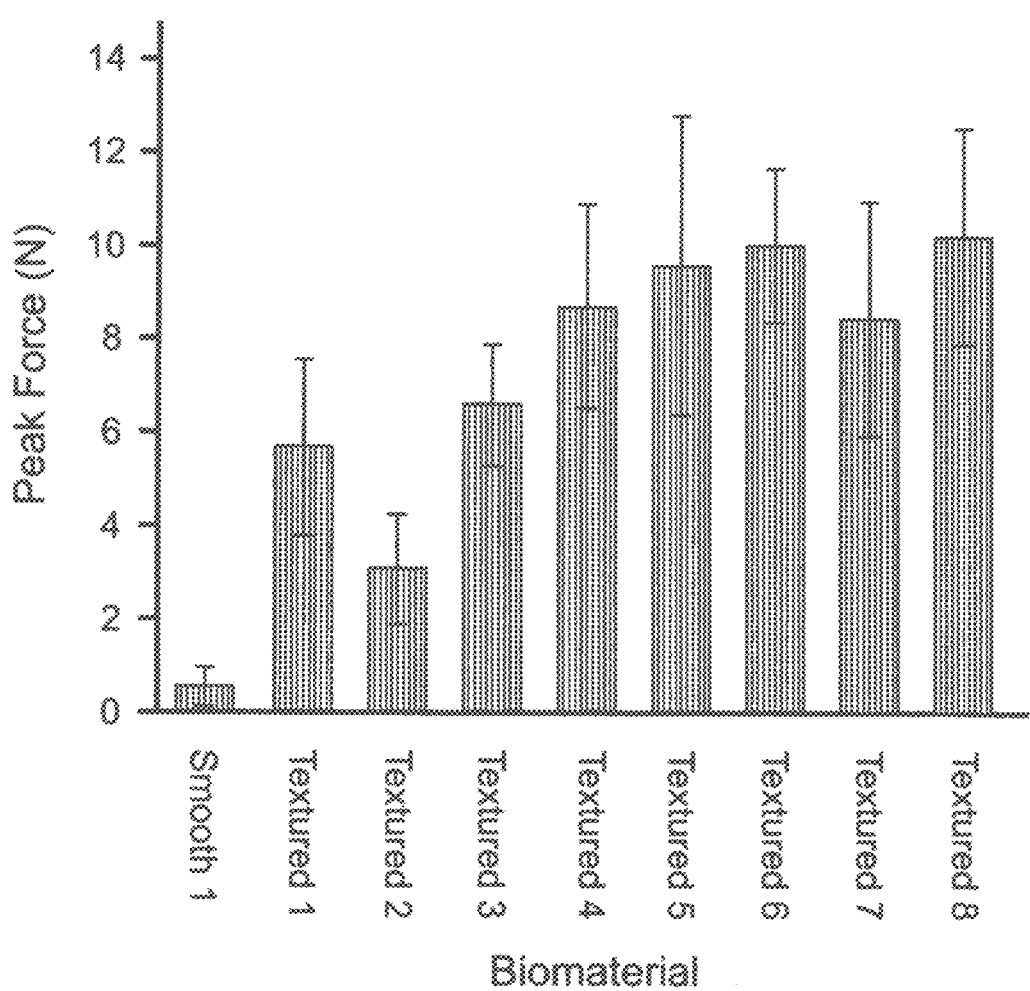
FIG. 7 is a bar graph showing data from a tissue adhesion test of various biomaterials. Results are shown as mean±standard deviation.

Smooth 1 biomaterial showed little adhesion, as there were no significant protrusions above a micro-scale and had minimal drag on the surrounding tissue (FIG. 7). Textured 1 and 2 biomaterials (closed-cell textured surfaces) exhibited limited amount of tissue interaction and showed greater adhesion than Smooth 1 (FIG. 7). Textured 3 and 4 biomaterials (inverse Foam textured surface) and Textures 5-8 biomaterials (open-cell textured surfaces) showed the highest degree of tissue adhesion (FIG. 7). As such, Textured 5-8 biomaterials promoted significant tissue infiltration/ingrowth because of the highly porous and interconnected textures.

Example 13

Capsule Stiffness

In order to evaluate stiffness of capsules/ingrowth formed over a porous biomaterial, 7 mL mini-expanders comprising silicone biomaterial of various textures were implanted subcutaneously in a Sprague-Dawley rat using standard procedures. The biomaterials tested were taken from commercially available implants or experimentally produced as follows: Smooth 1, a biomaterial having a smooth surface (NATRELLE®, Allergan, Inc., Irvine, Calif.); Textured 1, a biomaterial having a closed-cell textured surface produced from a lost-salt method (BIOCELL®, Allergan, Inc., Irvine, Calif.); Textured 2, a biomaterial having an open-cell textured surface of 0.8 mm produced according to the methods disclosed herein; Textured 3, a biomaterial having an open-cell textured surface of 1.5 mm produced according to the methods disclosed herein. At time 0 (immediately post-implantation) and at 6 weeks, saline was incrementally added to each expander, and the resulting pressure exerted on and by the expander at each step was measured with a digital manometer. Stiffness was calculated by fitting a trend-line to the linear region of the pressure-volume curve and measuring the slope of the line. Increases in the stiffness of the capsule/ingrowth were reflected by increases in the slope. To account for expander-to-expander variability, each stiffness measurement was normalized to the stiffness of the expander itself. A one-way ANOVA was run to determine significant effects ($p<0.05$). If there were any statistically significant effects from the ANOVA analysis, the Tukey's post-hoc test was run for multiple comparisons at $\alpha=0.05$.

Figure 8:
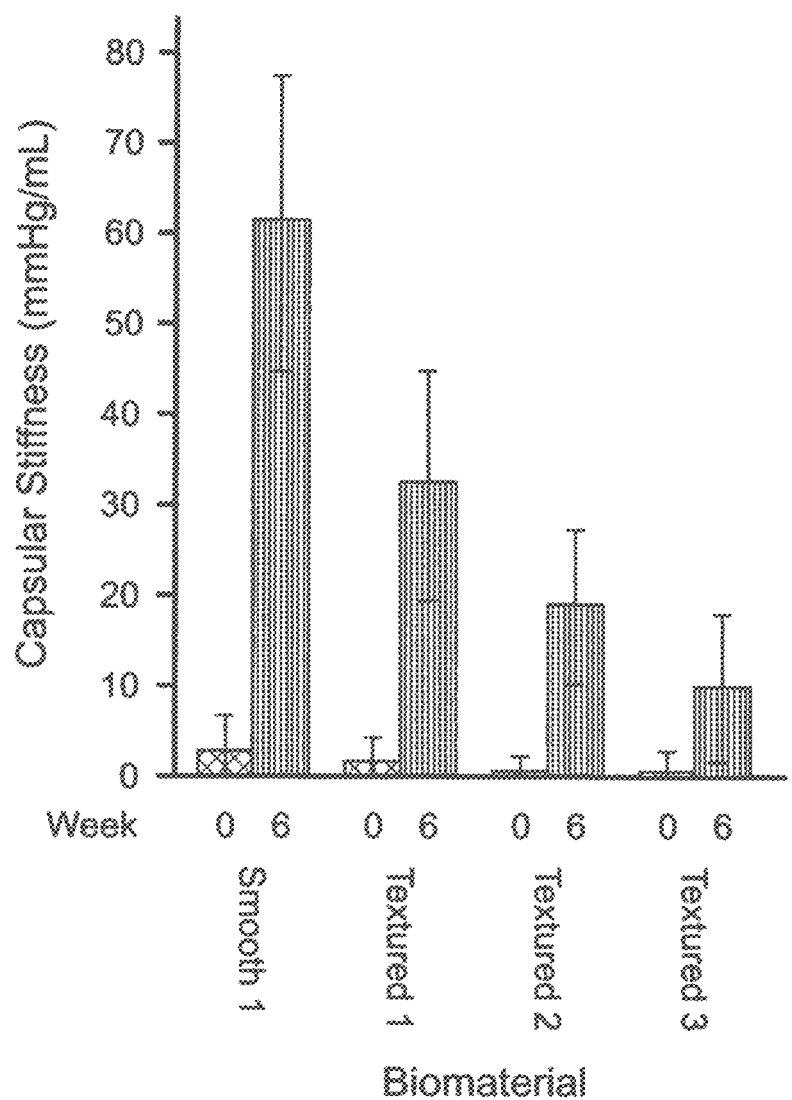
FIG. 8 is bar graph showing data of stiffness of capsule/ingrowth formed over various tissue expanders at time 0 and at 6 weeks (n=8). Results are shown as mean±standard deviation.

Capsules formed over Smooth 1 biomaterial expander showed the greatest stiffness after 6 weeks (FIG. 8). Textured 1 biomaterial expander (closed-cell textured surface) showed lower stiffness than Smooth 1 biomaterial expander but greater stiffness than the Textured 2 and 3 biomaterial expanders (open-cell textured surface) (FIG. 8). This data demonstrates that closed-cell biomaterials result in capsules that are stiffer than those that result from open-cell biomaterials that support ingrowth and prevent capsule formation.

Example 14

Capsule Response

In order to identify critical morphological and physical characteristics of the porous biomaterials disclosed herein, disks (1 cm in diameter) of various biomaterials were implanted subcutaneously in a Sprague-Dawley rat using standard procedures and the response to such implantation in terms of capsule formation was determined. The morphological and physical characteristics tested for each biomaterial are given in Tables 1 and 2.

TABLE 1

Morphological Characteristics of Biomaterials

| Biomaterial | Mean thickness (mm) | Mean porosity (%) | Mean pore size (μm) | Mean interconnections/ pore | Mean interconnection size (μm) |
|---|---|---|---|---|---|
| Polyurethane 1 | 2.40 ± 0.10 | 98.0 ± 0.4 | 522 ± 87 | 14.2 ± 3.2 | 166 ± 48 |
| Polyurethane 2 | 2.90 ± 0.01 | 98.0 ± 0.0 | 488 ± 119 | 14.2 ± 1.4 | 230 ± 69 |
| Mesh 1 | 0.89 ± 0.06 | 72.2 ± 1.5 | 522 ± 137 | N/A | N/A |
| Mesh 2 | 1.38 ± 0.10 | 70.9 ± 2.9 | 560 ± 134 | N/A | N/A |
| Fused Porogen 1 | 0.56 ± 0.38 | 55.6 ± 0.5 | 530 ± 150 | 7.0 ± 3.1 | 325 ± 242 |
| Fused Porogen 2 | 0.79 ± 0.06 | 72.6 ± 5.4 | 458 ± 48 | 7.8 ± 1.5 | 151 ± 59 |
| Fused Porogen 3 | 1.10 ± 0.00 | 77.6 ± 1.0 | 596 ± 150 | 4.6 ± 1.9 | 106 ± 42 |
| Fused Porogen 4 | 1.14 ± 0.09 | 66.4 ± 3.2 | 424 ± 68 | 8.0 ± 1.1 | 111 ± 49 |
| Fused Porogen 5 | 1.32 ± 0.02 | 77.9 ± 0.9 | 408 ± 64 | 7.6 ± 2.0 | 118 ± 44 |
| Fused Porogen 6 | 1.60 ± 0.10 | 77.8 ± 1.2 | N/D | N/D | N/D |
| Fused Porogen 7 | 1.60 ± 0.10 | 81.2 ± 1.3 | 608 ± 268 | 4.9 ± 1.9 | 130 ± 85 |

TABLE 1-continued

Morphological Characteristics of Biomaterials

| Biomaterial | Mean thickness (mm) | Mean porosity (%) | Mean pore size (μm) | Mean interconnections/ pore | Mean interconnection size (μm) |
|---|---|---|---|---|---|
| Fused Porogen 8 | 1.60 ± 0.00 | 85.3 ± 1.4 | 421 ± 48 | 8.2 ± 2.1 | 128 ± 38 |
| Fused Porogen 9 | 1.61 ± 0.03 | 80.3 ± 1.0 | 456 ± 81 | 7.4 ± 1.6 | 154 ± 50 |
| Fused Porogen 10 | 1.80 ± 1.20 | 80.6 ± 0.4 | 634 ± 124 | 7.5 ± 2.6 | 95 ± 33 |
| Fused Porogen 11 | 1.93 ± 0.78 | 82.8 ± 0.5 | 456 ± 65 | 7.1 ± 2.2 | 133 ± 46 |
| Fused Porogen 12 | 1.95 ± 0.19 | 76.5 ± 2.0 | 431 ± 57 | 7.0 ± 1.2 | 114 ± 58 |
| Fused Porogen 13 | 2.34 ± 0.06 | 74.0 ± 0.5 | 478 ± 112 | 7.1 ± 2.0 | 141 ± 47 |
| Fused Porogen 14 | 2.36 ± 0.12 | 81.1 ± 0.5 | 399 ± 93 | 7.4 ± 0.8 | 126 ± 64 |

TABLE 2

Physical Characteristics of Biomaterials

| Biomaterial | Compressive Response (kPa) at 5% strain | at 10% strain | at 20% strain | Elongation at Break (%) |
|---|---|---|---|---|
| Polyurethane 1 | 1.74 ± 0.40 | 2.60 ± 0.53 | 3.38 ± 0.52 | N/D |
| Polyurethane 2 | 1.41 ± 0.13 | 2.63 ± 0.03 | 2.89 ± 0.20 | 454 ± 7 |
| Mesh 1 | 0.07 ± 0.01 | 0.20 ± 0.02 | 0.74 ± 0.08 | 336 ± 39 |
| Mesh 2 | 0.09 ± 0.04 | 0.22 ± 0.09 | 0.74 ± 0.39 | 439 ± 56 |
| Fused Porogen 1 | 0.05 ± 0.00 | 0.18 ± 0.01 | 1.01 ± 0.14 | N/D |
| Fused Porogen 2 | 0.05 ± 0.03 | 0.23 ± 0.10 | 1.59 ± 0.46 | N/D |
| Fused Porogen 3 | 0.04 ± 0.01 | 0.14 ± 0.06 | 0.86 ± 0.36 | N/D |
| Fused Porogen 4 | 0.55 ± 0.21 | 1.55 ± 0.50 | 5.21 ± 1.18 | 287 ± 78 |
| Fused Porogen 5 | 0.13 ± 0.02 | 0.59 ± 0.14 | 3.26 ± 0.64 | N/D |
| Fused Porogen 6 | 0.10 ± 0.02 | 0.38 ± 0.11 | 2.24 ± 0.92 | N/D |
| Fused Porogen 7 | 0.094 ± 0.00 | 0.35 ± 0.06 | 1.86 ± 0.36 | N/D |
| Fused Porogen 8 | 0.04 ± 0.01 | 0.15 ± 0.04 | 0.61 ± 0.13 | 222 ± 33 |
| Fused Porogen 9 | 0.11 ± 0.03 | 0.46 ± 0.12 | 2.00 ± 0.26 | N/D |
| Fused Porogen 10 | 0.14 ± 0.01 | 0.43 ± 0.03 | 1.48 ± 0.01 | N/D |
| Fused Porogen 11 | 0.17 ± 0.00 | 0.64 ± 0.01 | 2.15 ± 0.03 | N/D |
| Fused Porogen 12 | 0.42 ± 0.14 | 1.07 ± 0.29 | 3.17 ± 0.61 | 384 ± 20 |
| Fused Porogen 13 | 0.19 ± 0.04 | 0.84 ± 0.16 | 3.48 ± 0.39 | N/D |
| Fused Porogen 14 | 0.06 ± 0.02 | 0.16 ± 0.06 | 0.61 ± 0.10 | 335 ± 11 |

Implanted porous biomaterials were harvested, fixed in formalin, and processed to produce paraffin blocks. The paraffin blocks were sectioned using a microtome at 2 μm thickness and stained with hematoxylin and eosin (H&E). Depending on the morphological characteristic being assessed, capsule response was measured by acquiring at least 3 representative 1×, 4×, 20×, or 50× images of sectioned biomaterial, digitally capturing the images, and measuring the characteristic at 3 or more point in each captured image. All image analysis calculations were performed on the Nikon Elements Advanced Research software. Physical characteristics of the materials were measured using routine methods. See, e.g., Winnie, Softness Measurements for Open-Cell Foam Materials and Human Soft Tissue, Measurement Science and Technology (2006).

The summary of the results obtained from this analysis are given in Table 3. The results indicate that in terms of capsule formation, increased porosity resulted in decreased capsule formation. More strikingly, increasing the number of interconnections per pore decreased capsule formation seen in the animals in response to the implanted porous biomaterials (Table 3). Lastly, a fine balance in the stiffness of a porous biomaterial, as measured by compressive forces, was needed to provide the optimal in vivo responses. Decreased stiffness resulted in decease capsule formation (Table 3).

| Characteristic | Capsule Response No Capsule | Capsule |
|---|---|---|
| Mean thickness (mm) | 0.8-2.9 | 0.6-2.9 |
| Mean porosity (%) | 72-98 | 56-81 |
| Mean pore size (μm) | 456-641 | 408-634 |
| Mean interconnections/pore | 7.1-14 | 4.6-9.5 |
| Mean interconnection size (μm) | 456-641 | 408-634 |
| Compressive at 5% strain (kPa) | 0.05-1.70 | 0.00-2.57 |
| Compressive at 10% strain (kPa) | 0.22-4.17 | 0.10-8.00 |
| Compressive at 20% strain (kPa) | 1.10-7.60 | 0.90-16.0 |

Analyzing all the data obtained from these experiments revealed optimal morphological and physical characteristics for a porous material produced from the porogen method disclosed herein, was as follows: having a porosity of about 80% to about 88%, having an interconnection size of about 110 μm to about 140 μm, having about 7 to about 11 interconnections per pore, having a compressive force of about 0.50 kPa to about 0.70 kPa at 5% strain, having a compressive force of about 1.0 kPa to about 2.0 kPa at 10% strain, and having a compressive force of about 3.5 kPa to about 5.5 kPa at 20% strain. In an aspect of this embodiment, optimal morphological and physical characteristics for a porous material produced from the porogen method disclosed herein, was as follows: having a porosity of about 83% to about 85%, having an interconnection size of about 120 μm to about 130 μm, having about 8 to about 10 interconnections per pore, having a compressive force of about 0.55 kPa to about 0.65 kPa at 5% strain, having a compressive force of about 1.3 kPa to about 1.7 kPa at 10% strain, and having a compressive force of about 4.0 kPa to about 5.0 kPa at 20% strain.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for forming a textured implant shell, the method comprising:
    coating a base shell with a first layer of an elastomer, the elastomer comprising a silicone base and a solvent;
    applying porogens to the first layer of elastomer to form a first porogen-coated elastomer layer;
    applying a second layer of the elastomer to the first porogen-coated elastomer layer;
    applying porogens to the second layer of elastomer to form a second porogen-coated elastomer layer;
    applying a third layer of the elastomer to the second porogen-coated elastomer layer to thereby form a multilayered porogen/elastomer coating on the base shell;
    treating the multilayered porogen/elastomer coating on the base shell such that during the treatment the porogens become fused to one another while the uncured elastomer layers become cured, thereby forming a fused porogen scaffold surrounded by cured elastomer; and removing the porogen scaffold from the cured elastomer, wherein the removing the porogen scaffold results in an interconnected open-cell textured implant shell;

wherein the porogens comprise poly(ethylene) glycol.

2. The method of claim 1, wherein the poly(ethylene) glycol has a glass transition temperature (Tg) from about 30° C. to about 100° C.

3. The method of claim 1, wherein the step of treating the multilayered porogen/elastomer coating by subjecting the multilayered porogen/elastomer coating to heat in the range of about 110° C. to about 135° C. for about 60 minutes to about 90 minutes.

4. The method of claim 1, wherein the porogens have a mean particle diameter of between about 300 μm to about 600 μm.

5. The method of claim 1, wherein the porogens have a mean particle diameter of about 400 μm to about 500 μm.

6. The method of claim 1, wherein the porogens further comprise a sugar.

7. The method of claim 1, wherein the porogens further comprise a salt.

8. A method for making a breast implant having a textured surface, the method comprising:
   (a) coating a breast implant shell with an uncured elastomer base to form an elastomer coated breast implant shell wherein the uncured elastomer base comprises a silicon-based elastomer and a solvent;
   (b) devolitalizing the solvent;
   (c) coating the elastomer coated breast implant shell with porogens to form an elastomer coated porogen mixture;
   (d) devolitalizing the solvent;
   (e) repeating step (a);
   (f) devolitalizing the solvent;
   (g) repeating step (c);
   (h) devolitalizing the solvent;
   (i) repeating step (a);
   (j) devolitalizing the solvent;
   (k) repeating step (c);
   (l) devolitalizing the solvent;
   (m) treating the elastomer coated porogen mixture such that the porogens are fused to form a porogen scaffold and the uncured elastomer base is cured; and
   (n) removing the porogen scaffold, wherein the removing the porogen scaffold results in the breast implant with porous material;

wherein the porogens comprise poly(ethylene) glycol.

9. The method of claim 8, wherein steps (a)-(l) are conducted at about 20° C. to about 25° C., and step (m) is conducted in the range of about 110° C. to about 135° C. for about 60 minutes to about 90 minutes.

10. The method of claim 8, wherein step (m) is conducted at 126° C. for 85 minutes.

11. The method of claim 8, wherein step (b) is for about 18 minutes to about 22 minutes.

12. The method of claim 8, wherein step (d), step (f) and/or step (j) is for about 3 minutes to about 6 minutes.

13. The method of claim 8, wherein step (h) is for about 25 minutes to about 35 minutes.

14. The method of claim 8, wherein step (l) is for at least 45 minutes.

15. The method of claim 8, wherein the porogens further comprise a sugar.

16. The method of claim 8, wherein the porogens further comprise a salt.

* * * * *